United States Patent
Brüstle et al.

(10) Patent No.: US 9,844,572 B2
(45) Date of Patent: Dec. 19, 2017

(54) PROMOTION OF NEURONAL INTEGRATION IN NEURAL STEM CELL GRAFTS

(75) Inventors: Oliver Brüstle, Bonn (DE); Philipp Koch, Bonn (DE); Julia Ladewig, Bonn (DE)

(73) Assignee: Life & Brain GmbH, Bonn (DE)

( * ) Notice: Subject to any disclaimer, the term of this patent is extended or adjusted under 35 U.S.C. 154(b) by 120 days.

(21) Appl. No.: 13/258,714

(22) PCT Filed: Mar. 24, 2010

(86) PCT No.: PCT/EP2010/001841
§ 371 (c)(1),
(2), (4) Date: Dec. 12, 2011

(87) PCT Pub. No.: WO2010/108665
PCT Pub. Date: Sep. 30, 2010

(65) Prior Publication Data
US 2012/0093832 A1    Apr. 19, 2012

(30) Foreign Application Priority Data

Mar. 24, 2009  (WO) ................ PCT/EP2009/002149

(51) Int. Cl.
*A61K 39/395* (2006.01)
*A61K 35/30* (2015.01)
*A61P 25/28* (2006.01)
*A61P 31/00* (2006.01)
*C07K 16/28* (2006.01)

(52) U.S. Cl.
CPC .......... *A61K 35/30* (2013.01); *C07K 16/2863* (2013.01); *C07K 2317/76* (2013.01)

(58) Field of Classification Search
CPC .. A61K 35/30; A61K 39/395; C07K 2317/76; C07K 14/50; C07K 16/2863
See application file for complete search history.

(56) References Cited

U.S. PATENT DOCUMENTS

2004/0259071 A1* 12/2004 Sortwell et al. ............... 435/1.1
2007/0265203 A1* 11/2007 Eriksson et al. ............... 514/12

FOREIGN PATENT DOCUMENTS

WO    WO 0037502 A2 * 6/2000

OTHER PUBLICATIONS

PCT International Preliminary Report on Patentability, including (1) Notification Concerning Transmittal of International Preliminary Report on Patentability and (2) Written Opinion of the International Searching Authority, for PCT/EP2010/001841, dated Oct. 6, 2011 (6 pages).
PCT International Search Report for PCT/EP2010/001841, dated Jun. 5, 2010 (3 pages).
Boecker-Meffert, Simone et al. Erythropoietin and VEGF Promote Neural Outgrowth from Retinal Explants in Postnatal Rats. IOVS vol. 43, No. 6, Jun. 2002, pp. 2021-2026.
Elkabetz, Yechiel et al. Human ES cell-derived neural rosettes reveal a functionally distinct early neural stem cell age. Genes & Development vol. 22, No. 2, Jan. 2008, pp. 152-165.
Jiao, Shujie et al. Effect of VEGF on Neural Differentiation of Human Embryonic Stem Cells in vitro. Journal of Huazhong University of Science and Technology; Medical Sciences vol. 29, No. 5, Oct. 2009, pp. 563-566.
Koch, Philipp et al. A rosette-type, self-renewing human ES cell-derived neural stem cell with potential for in vitro instruction and synaptic integration. Proceedings of the National Academy of Sciences of the USA vol. 106, No. 9, Mar. 2009, pp. 3225-3230.
Ladewig, Julia et al. Lineage Selection of Functional and Cryopreservable Human Embryonic Stem Cell-Derived Neurons. Stem Cells (Miamisburg) vol. 26, No. 7, 2008, pp. 1705-1712.
Rueschenschmidt, Christiane et al. Functional Properties of ES Cell-Derived Neurons Engrafted into the Hippocampus of Adult Normal and Chronically Epileptic Rats. Epilepsia vol. 46, No. Suppl. 5, 2005, pp. 174-183.

\* cited by examiner

*Primary Examiner* — Gregory S Emch
(74) *Attorney, Agent, or Firm* — Melissa Huntor-Ensor; Leslie Serunian; Greenberg Traurig, LLP

(57) ABSTRACT

The invention relates to the treatment of diseases or disorders of the nervous system. In particular, the invention relates to the treatment of diseases or disorders of the nervous system by stem cell therapy, in particular therapy with neural precursor cells. In preferred aspects of the invention, inhibitors of chemoattraction are administered prior to, concomitantly with, or subsequently to the administration of neural precursor cells.

13 Claims, 10 Drawing Sheets

A

B

A

B g

| Experiment | Control | BIBF1120 |
|---|---|---|
| 1 | 49,66±8,02 | 104,33+8,33 |
| 2 | 49,67+8,02 | 86±7,93 |
| 3 | 64±5,57 | 142,33+7,37 |

PROMOTION OF NEURONAL INTEGRATION IN NEURAL STEM CELL GRAFTS

FIELD OF THE INVENTION

The invention relates to the field of the treatment of diseases or disorders of the nervous system. In particular, the invention relates to the treatment of diseases or disorders of the nervous system by stem cell therapy, in particular therapy with neural precursor cells. In preferred aspects of the invention, inhibitors of chemoattraction are administered prior to, concomitantly with, or subsequently to the administration of neural precursor cells.

BACKGROUND OF THE INVENTION AND STATE OF THE ART

Transplantation of Neural Stem Cells

The CNS has a very limited regenerative capacity. Thus it is of major interest to investigate the ability of human neural stem cells (NSCs) engrafted into the brain to survive, migrate and integrate in a functional and meaningful manner.

Studies have shown that stem cells derived from the embryonic or fetal human brain can be successfully grafted into the developing rodent CNS. Once transplanted, these cells survive, migrate and integrate into the host tissue, giving rise to cells from the three fundamental neuronal lineages i.e. neurons, astrocytes and oligodendrocytes (Brustle et al., 1998; Flax et al., 1998; Uchida et al., 2000; Englund et al., 2002b; Peng et al., 2002; Honda et al., 2007).

However, transplantation studies in the adult CNS are more challenging. As the tissue is fully established, developmental cues are limited and space is more constricted (Svendsen & Caldwell, 2000) leading to restricted migration and integration of the transplanted cells. Engraftment of fetal or ES cell derived neural progenitors in the adult CNS could show that transplanted cells survive but form a graft core meaning that the majority of the transplanted cells remain mainly situated at the grafted site (Guzman et al., 2008). Restricted migration of the transplanted cells could be observed 10 to 15 weeks following engraftment (Fricker et al., 1999; Aleksandrova et al., 2002; Englund et al., 2002a; Tabar et al., 2005; Roy et al., 2006; Guzman et al., 2008). It was suggested that physical or molecular barriers caused by glial scarring at the transplantation site are the reason for the restricted outgrowth of transplanted cells (Reier et al., 1983; Rudge & Silver, 1990). Such effect might be solved by microtransplants, which minimize scarring at the grafted site (Nikkhah et al., 1995; Davies et al., 1997).

Nevertheless, cell replacement therapies for diseases of the adult brain have attracted attention since the first reports of successful transplantation of embryonic dopaminergic cells to patients with Parkinson's disease (Lindvall & Hagell, 2001). Parkinson's disease is characterized by a loss of dopamine-producing midbrain neurons with cell bodies in the substantia nigra. These neurons project to the striatum and are essential for motor function. Parkinson's patients suffer from various symptoms including resting tremor, difficulty in walking, and loss of facial expression. The disease is typically progressive due to ongoing loss of neurons. The first transplantation studies with fetal tissue in animal models of Parkinson's disease have shown that grafted dopaminergic cells are able to release dopamine at near normal levels and that the animals show significant behavioural recovery (Annett et al., 1994; Herman & Abrous, 1994; Lindvall et al., 1994). Positive effects have also been observed in clinical trails with human patients (Olanow et al.; Lindvall, 1999). Major improvements, however, were only seen in patients aged 60 years or younger (Freed et al.). Moreover, some patients receiving transplants developed dyskinesias, movement disorders associated with excessive dopamine levels in the brain. Further success of these transplantation approaches has been constrained by limited availability of fetal tissue, limited migration of grafted cells, and poor differentiation and survival of the grafted neurons (Richardson et al., 2004). In addition to these problems, fresh fetal tissue cannot be standardized and raises ethical questions that have been debated intensely (Bjorklund & Lindvall, 2000).

Many of these issues can be better addressed by working towards an in vitro culture system. The knowledge about hES cells, including techniques of producing stable well-characterised NSCs from hES cells has provided prospects to generate large numbers of donor cells for neural repair (Koch et al., 2009). Many studies already show that neural progenitors derived from ES cells can give rise to dopaminergic neurons. This is mainly achieved by the combined use of FGF8 and Shh, which effectively induce dopaminergic neurons from ES cell-derived neural progenitors (Lee et al., 2000; Yan et al., 2005). Addition of ascorbic acid, brain-derived neurotrophic factor (BDNF), glial-derived neurotrophic factor (GDNF), dibutyryl cyclic-AMP, and transforming growth factor-beta 3 (TGF-$\beta$3) yields cultures containing 30% to 50% neurons expressing beta-III tubulin, of which 65% to 80% express tyrosine hydroxylase required for dopamine synthesis. These neurons release dopamine upon depolarization, and form at least rudimentary synapses in vitro with transmitter re-uptake abilities (Kim et al., 2007; Joannides et al., 2007). Following transplantation these cells survive, maintain their dopaminergic phenotype and functionally engraft in the brain (Sanchez-Pernaute et al., 2005; Yang et al., 2008). Using cultured ES cell-derived neural precursors as a source for transplantation therapies may, on the one hand, obviate some of the technical limitations associated with the use of fresh fetal tissue (Ostenfeld & Svendsen, 2003), but may also on the other hand, bear the risk of teratoma formation. Currently, the only way to ensure that teratomas do not form is to differentiate the ES cells in advance, enrich for the desired cell type and screen for the presence of undifferentiated cells. In addition, hES cell-derived neural precursor transplants have been found to give rise to proliferating neural clusters rather than individually incorporating neurons (Roy et al., 2006) indicating that even committed progenitors can proliferate excessively after transplantation. This problem might be solved by using more restricted precursor cells or by the purification of desired postmitotic subtypes of neurons or glia.

Compared to cell replacement therapy for Parkinson's disease, in which one specific type of neurons has to be replaced by a direct local cell transplantation, cell therapy for stroke or spinal cord injury is a major challenge as transplanted NSCs need to replace a range of neuronal types, remyelinate axons and repair complex neural circuitries. In addition, it is required that transplanted cells reach the lesion site by following a gradient of inflammatory cues such as cytokines and chemokines (Ransohoff, 2002). As a preliminary step towards this goal, it was shown that human NSCs transplanted into the brains of rodents after stroke survived, migrated, and differentiated into various types of neurons (Aoki et al., 1993; Ben-Hur et al., 2003; Imitola et al., 2004; Kelly et al., 2004). Other degenerative diseases of the adult CNS such as Alzheimer's disease and amyotrophic lateral sclerosis would also require the migration of transplanted cells towards specific sites within the CNS. Many neurodegenerative diseases are associated with a non-permissive environment, which can inhibit regenerative processes. These circumstances create an even bigger challenge for cell replacement therapy.

Thus, the major difficulties yet to be solved are how to direct and control the differentiation of specific phenotypes required for replacement and repair in each disease, how to purify lineage specific subtypes and how to improve cell migration and integration into the affected site of the CNS.

Several previous studies analysed the migration and integration potential of hES cell-derived neurons in vivo. Former studies, in which hES cell-derived neural cells were transplanted into rat brains, described clusters of donor cells at the site of engraftment one week after transplantation, the so called transplantation cores (Reubinoff et al., 2001). Tabar (Tabar et al., 2005) and co-workers investigated in vivo migration of hES cell-derived neural precursors transplanted into the rostral migratory stream of adult rats and found that about one fourth of the transplanted cells migrated out of the transplantation core within 11 weeks.

In comparison, the inventors observed when transplanting pure populations of immature human neurons into the striatum of adult rats, a large amount of the cells migrated out of the transplantation core within 8 days. Similar results have been achieved following transplantation into the rostral migratory stream, where transplanted neurons morphologically orientated to and migrated towards the olfactory bulb within 8 days. In contrast, the corresponding immature neurons within a cell mixture with neural stem/progenitor cells did not show such a strong migratory behaviour although they should in principle have the same migration potential as the pure neurons. It was observed that the cells of mixed neural/neuronal transplants formed densely packed clusters at the transplantation site with only restricted migration of neurons out of the transplantation core.

Cluster formation and limited migration and integration have been topics in neurobiological research for many years. A major challenge in therapeutic transplantation of donor cells for neural damage repair is to achieve functional integration of the donor cells into the host tissue. Limited integration due to restricted emigration of the transplanted cells, which mainly remain located at the grafted site (Guzman et al., 2008) is a widely discussed issue and described in many different studies using primary cells or ES cell derived neural progeny (Fricker et al., 1999; Tabar et al., 2005; Roy et al., 2006). It is argued that this core formation of neural transplants is due to physical or molecular barriers caused by glial scarring at the lesion site following transplantation (Reier et al., 1983; Rudge & Silver, 1990). Successful axonal outgrowth is known to be associated with minimal up-regulation of proteoglycans within the extracellular matrix of reactive glial cells at the transplantation site (Davies et al., 1997). This might also restrict migration of transplanted neuronal progenitors. It was suggested that the up-regulation of proteoglycans might be avoided by using microtransplants that minimize scarring by injecting minimal volumes of dissociated cells (Nikkhah et al., 1995; Davies et al., 1997).

Erythropoietin

Erythropoietin (EPO) is a member of the hematopoietic growth factor family and behaves as a hormone. It is responsible for the regulation of red blood cell (erythrocyte) production (erythropoiesis), maintaining the body's red blood cell mass at an optimum level. EPO production is stimulated by reduced oxygen content in the renal arterial circulation, mediated by a transcription factor that is oxygen-sensitive. EPO is a produced primarily by cells of the peritubular capillary endothelium of the kidney. Secreted EPO binds to EPO receptors on the surface of bone marrow erythroid precursors, resulting in their rapid replication and maturation to functional red blood cells. This stimulation results in a rapid rise in erythrocyte counts and a consequent rise in hematocrit (% of red blood cells in blood) (D'Andrea et al Cell 1989 57: 277-285. Lodish et al Cold Spring Harb Symp Quant Biol 1995 60: 93-104).

Human EPO was first cloned and amino acid sequence reported by Lin et al. (Proc. Natl. Acad. Sci. USA 1985 82: 7582-4) and Jacobs K. et al. (Nature 313: 806-810 1985).

Human EPO is an acidic glycoprotein with a molecular weight of approximately 30400 daltons. It is composed of an invariant 165 amino acid single polypeptide chain containing four cysteine residues (at positions 7, 29, 33 and 161), which form the internal disulphide bonds (Lai et al., J. Biol. Chem. 1986, 261: 3116-3121; Recny et al. J. Biol. Chem. 1987 262: 17156-17163). The disulphide bridge between cysteine 7 and 161 is known to be essential for biological activity. The carbohydrate portion of EPO consists of three N-linked sugars chains at Asn 24, 38 and 83, and one O-linked sugar at Ser 126 (Browne J. K. et al. Cold spring Harb. symp. Quant. Biol. 1986, 51: 693-702 Egrie J. C. et al. Immunbiology 1986 172: 213-224.)

The structure of human EPO has been reported (Cheetham et al 1988 Nat. Struct. Biol. 5:861-866; Syed et al. 1998 Nature 395:511-516). Human EPO is a four helix bundle, typical of members of the hematopoietic growth factor family. In contrast to the invariant amino acid sequence, the carbohydrate structures are variable, a feature referred to as micro-heterogeneity. The differences in carbohydrate moieties, in terms of the branching pattern, complexity size and charge have profound effects on the pharmacokinetics and pharmacodynamics of EPO. The effects of different glycosylation patterns have been well studied (Darling et al. 2002 Biochemistry 41: 14524-14531; Storring et al. 1998 Br. J. Haematol. 100: 79-89; Halstenson et al 1991 Clin. Pharmacol. Ther. 50: 702-712; Takeuchi et al. 1990 J. Biol. Chem. 265: 12127-12130).

The following EPOs have the same amino acid sequence as recombinant human EPO (rhEPO) and variations in the methods of production and glycosylation distinguish these products. Epoetin alfa (genomic DNA) and epoetin beta (cDNA) are described in U.S. Pat. Nos. 4,703,008 and 5,955,422. These have the same amino acid sequence as human EPO and are produced in chinese hamster ovary (CHO) cells. Epoetin alfa is available under the trade names procrit (Ortho Biotech), eprex (Johnson & Johnson), epogin (Chugai) or epogen (Amgen). Epoetin beta is available under the trade name neorecormon or recormon (Hoffmann-La Roche). It was developed by the Genetics Institute for the treatment of anaemia associated with renal disease. Epoetin omega described in U.S. Pat. No. 5,688,679 has the same amino acid sequence as human EPO and is produced in baby hamster kidney cells (BHK-21). Epoetin omega is available under the trade names EPOMAX (Elanex).

Darbepoetin alfa (novel erythropoiesis stimulating protein, NESP) was developed by Amgen and is available under the trade name ARANESP (Macdougall I. C., Kidney Int. Suppl. 2002 May; (80):55-61). It was designed to contain five N-linked carbohydrate chains (two more than rhEPO). The amino acid sequence of Aranesp differs from that of rhEPO at five substitutions (Ala30Asn, His32Thr, Pro87Val, Trp88Asn, Pro90Thr), thus allowing for additional oligosaccharide attachment at asparagine residues at position 30 and 88. Due to its increased carbohydrate content, Aranesp differs from rhEPO as a result of a higher molecular weight (37,100 compared to 30,400 Daltons), sialic acid content (22 compared to 14 sialic acid residues) and increased negative charge. The increased carbohydrate content of Aranesp accounts for its distinct biochemical and biological properties, in particular a 3-fold longer circulating half-life than other existing erythropoietins when administered via the intravenous (IV) or subcutaneous (SC) route. However, the relative EPO receptor binding affinity was inversely correlated with the carbohydrate content, with Aranesp displaying a 4.3-fold lower relative affinity for the EPO receptor than that of rhEPO. Following SC administration, the absorption of Aranesp is slow and rate-limiting, serum levels reaching a maximum at a mean of 54 h. The time to maximum concentration is longer than that reported for rhEPO, probably because of the increased molecular size of Aranesp. However currently, the extended circulating half-life gives Aranesp a significant clinical advantage over Procrit due to its less frequent dosing. Opportunities may exist however, to explore possible improvements to the affinity of Aranesp for its receptor or to address the rate of absorption following SC administration.

Transkaryotic Therapies (in conjunction with Aventis Pharma) are developing erythropoietin stimulant Dynepo (epoetin delta). Dynepo is a gene-activated human erythropoietin produced in human cell culture, for the treatment of anemia in patients with renal failure.

Roche is developing R-744, continuous erythropoietin receptor activator (CERA), a second-generation erythropoietin, for the potential treatment of anemia associated with chemotherapy. CERA contains a single methoxypolyethylene glycol polymer of approximately 30 kDa that extends the half life of this agent.

Many EPO individual point mutants have been made to study the EPO structure activity relationship (Elliot et al. 1997 Blood 89: 493-502; Elliot et al. 1996 Blood 87: 2702-2713; Syed et al. 1998 Nature 395: 511-516) or effects of glycosylation (O'Narhi et al. 2001 Protein Engineering 14: 135-140; Bill et al. 1995 Biochimica et Biophysica Acta 1261: 35-43; Yamaguchi et al. 1991 J Biol Chem 266: 20434-20439).

EPO is a major biopharmaceutical product with worldwide sales topping US$ 3 billion. It is used primarily to boost erythrocyte and red blood cell formation in patients to treat anaemia associated with chronic renal failure, cancer chemotherapy, HIV infection, pediatric use, premature infants and to reduce the need for blood transfusions in anaemic patients undergoing elective non-cardiac and non-vascular surgery.

Endostatin

Endostatin is a 20 kDa C-terminal fragment of collagen XVIII, a member of a family of collagen-like proteins called multiplexins (O'Reilly, M. S. et al. Endostatin: An endogenous inhibitor of angiogenesis and tumor growth. *Cell* 1997, 88: 277-285). Collagen XVIII is a component of the basement membrane zones that surround blood vessels (Muragaki, Y. et al. Mouse col18a1 is expressed in a tissue-specific manner as three alternative variants and is localized in basement membrane zones. Proc. Natl. Acad. Sci. USA 1995, 92, 8763-8767). Endostatin is an inhibitor of angiogenesis. It specifically inhibits endothelial cell proliferation, that is, it has no effect on the growth of other cell types. It is produced naturally by a murine hemangioendothelioma, from which it was first purified (O'Reilly, M. S. et al., supra). Recombinant *E. coli*-derived endostatin, when added at a site remote from the primary tumor, has a systemic effect causing even very large tumors (1% of body weight) to regress to dormant microscopic nodules (O'Reilly, M. S. et al., supra). Hence tumors can be forced to regress over 150-fold in size to less than 1 mm$^3$. As long as treatment is continued there is no tumor regrowth, and no toxicity. When treatment is initially stopped tumors regrow, however treatment can be continued and drug-resistance does not develop over multiple treatment cycles (Boehm, T. et al., Antiangiogenic therapy of experimental cancer does not induce acquired drug resistance. Nature 1997, 390: 404-407). Remarkably, repeated cycles of antiangiogenic therapy were followed by self-sustained dormancy that remained for the lifetime of most animals (Boehm et al., supra). The mechanism for the persistence of tumor dormancy after therapy is suspended is unknown, but it is not due to an antitumor immune response, as tumors injected at sites remote from the treated tumor grew unchecked. The dormant tumors which are of a size that can survive without blood vessels display no net gain in size due to a balance between high proliferation of tumor cells, and high apoptosis.

The mechanism of action of endostatin remains unknown. The anti-angiogenic effects of endostatin may be due in part to its ability to block the attachment of endothelial cells to fibronectin via $\alpha 5\beta 1$, and $\alpha V\beta 3$ integrins (Rehn, M. et al., Interaction of endostatin with integrins implicated in angiogenesis. Proc. Natl. Acad. Sci. USA 2001, 98: 1024-1029) and/or $\alpha 2\beta 1$ (Furumatsu, T. et al., Endostatin inhibits adhesion of endothelial cells to collagen I via alpha(2)beta(1) integrin, a possible cause of prevention of chondrosarcoma growth. J. Biochem. 2002, 131: 619-626.).

Angiostatin

Angiostatin is a 38,000-Mr protein comprising the first four of five highly homologous 80-amino acid residue long triple-loop structures termed kringles (O'Reilly M. S. et al., Angiostatin: a novel angiogenesis inhibitor that mediates the suppression of metastases by a Lewis lung carcinoma. Cell. 1994; 79:315-328). It can inhibit the growth of a broad array of murine and human tumors established in mice (O'Reilly M. S. et al., Angiostatin induces and sustains dormancy of human primary tumours in mice. Nat. Med. 1996; 2:689-692), and is non-toxic such that tumors can be subjected to repeated treatment cycles, without exhibiting acquired resistance to therapy (Boehm T et al., supra). Its tumor-suppressor activity may arise from its ability to inhibit the proliferation of endothelial cells by binding to the $\alpha/\beta$-subunits of ATP synthase (Moser T. L. et al., Angiostatin binds ATP synthase on the surface of human endothelial cells. Proc Natl Acad Sci USA 1999; 96:2811-2816), by inducing apoptotic cell death (Holmgren L. et al., Dormancy of micrometastases-balanced proliferation and apoptosis in the presence of angiogenesis suppression. Nat. Med. 1995; 1: 149-153), by subverting adhesion plaque formation and thereby inhibiting the migration and tube formation of endothelial cells (Claesson-Welsh L. et al. Angiostatin induces endothelial cell apoptosis and activation of focal adhesion kinase independently of the integrin-binding motif RGD. Proc Natl Acad Sci USA. 1998; 95:5579-5583), and/or by down-regulating vascular endothelial growth factor (VEGF) expression (Kirsch M. et al. Angiostatin suppresses malignant glioma growth in vivo. Cancer Res. 1998; 58:4654-4659; Joe Y. A. et al. Inhibition of human malignant glioma growth in vivo by human recombinant plasminogen kringles 1-3. Int. J. Cancer 1999; 82:694-699). Angiostatin reduces the phosphorylation of the mitogen-activated protein kinases ERK-1 and ERK-2 in human dermal microvascular cells in response to VEGF (Redlitz A. et al. Angiostatin diminishes activation of the mitogen-activated protein kinase ERK-1 and ERK-2 in human dermal microvascular endothelial cells. J. Vasc. Res. 1999; 36:28-34). Endothelial progenitor cells are exquisitely sensitive to the effects of angiostatin, and may be the most important target of angiostatin (Ito H. et al. Endothelial progenitor cells as putative targets for angiostatin. Cancer Res. 1999; 59:5875-5877). Gene transfer of angiostatin into small solid EL-4 lymphomas established in mice led to reduced tumor angiogenesis, and weak inhibition tumor growth (Sun, X. et al. Angiostatin enhances B7.1-mediated cancer immunotherapy independently of effects on vascular endothelial growth factor expression. Cancer Gene Ther. 8: 719-727, 2001). In contrast, when angiostatin gene therapy was preceded by in situ gene transfer of the T cell costimulator B7-1, large tumors were rapidly and completely eradicated; whereas B7-1 and angiostatin monotherapies were ineffective. Gene transfer of AAV-angiostatin via the portal vein led to significant suppression of the growth of both nodular and, metastatic EL-4 lymphoma tumours established in the liver, and prolonged the survival time of the mice (Xu, R. et al. Long-term expression of angiostatin suppresses metastatic liver cancer in mice. Hepatol. 37:1451-60, 2003). Survivin is a recently identified member of the inhibitor of apoptosis (IAP) proteins (Ambrosini, G. et al. 1997. A novel anti-apoptosis gene. Survivin expression in cancer and lymphoma. Nat. Med. 3: 917-921) which are now regarded as important targets in cancer therapy. Antisense complementary DNA (cDNA) and oligonucleotides that reduce the expression of the IAP protein Bcl-2 inhibit the growth of certain tumor cell lines in vitro (Ambrosini et al. 1997, supra; Webb, A. et al. 1997. BCL-2 antisense therapy in patients with non-Hodgkin lymphoma. Lancet 349:1137-1141; Miayake, H. et al. 2000. Chemosensitization and delayed androgen-independent recurrence of prostate cancer with the use of antisense Bcl-2 oligodeoxynucleotides. J. Natl. Cancer Inst. 92: 34-41). Similarly, antisense oligonucleotides that reduce survivin expression in tumors cells induce apoptosis and polyploidy, decrease colony formation in soft agar, and sensitize tumor cells to chemotherapy in vitro (Baba, M. et al., 2000. In vivo electroporetic transfer of Bcl-2 antisense oligonucleotide inhibits the development of hepatocellular carcinoma in rats. Int. J. Cancer 85: 260-266; Li, F. Z. et al. 1999. Pleiotropic cell-division defects and apoptosis induced by interference with survivin function. Nat. Cell Biol. 1: 461-466; Chen, J. et al. 2000. Down-regulation of survivin by antisense oligonucleotides increases apoptosis, inhibits cytokinesis and anchorage-independent growth. Neoplasia 2:235-241; Grossman, D. et al. 1999. Expression and targeting of the apoptosis inhibitor, survivin, in human melanoma. J. Invest. Dermatol. 113:1076-1081). Intratumoral injection of plasmids that block survivin expression were found to inhibit tumor growth, particularly the growth of large tumors (Kanwar, J. R. et al. 2001. Effect of survivin antagonists on the growth of established tumors and B7.1 immunogene therapy. J. Natl. Cancer Inst. 93:1541-1552.).

Vascular Endothelial Growth Factor (VEGF) and their Receptors

VEGF was identified as a protein that induces proliferation and migration of endothelial cells in vitro, and blood vessel permeabilization and angiogenesis in vivo. It regulates both vascular proliferation and permeability. Also known as vascular permeability factor (VPF), it is unique among pro-angiogenic factors because of its specificity for vascular endothelium and potency. It also functions as an anti-apoptotic factor for endothelial cells in newly formed vessels. VEGF is expressed in tumor cells, macrophages, T cells, smooth muscle cells, kidney cells, mesangial cells, keratinocytes, astrocytes, and osteoblasts.

The VEGF family comprises seven members, including VEGF-A, VEGF-B, VEGF-C, VEGF-D, VEGF-E, VEGF-F, and placental growth factor (PlGF). All of them have a common structure of eight cysteine residues in a VEGF homology domain. In addition, in relation to VEGF-A, there are six different isoforms, and VEGF-A165 is the main isoform. All these isoforms have distinct and overlapping functions in angiogenesis. The VEGF gene is located on chromosome 6p. 21. The different members of VEGF family have different physical and biological properties and they act through specific tyrosine kinase receptors (VEGFR-1 (also termed Flt-1), VEGFR-2 (also termed Flk-1/KDR), and VEGFR-3 (also termed (Flt-4)). The VEGFR-3 receptor and its ligands, VEGF-C and VEGF-D, are associated with lymphangiogenesis, while PlGF is linked to arteriogenesis.

A synthetic peptide, ATWLPPR has been shown to abolish VEGF binding to cell-displayed KDR, and abolished VEGF-induced angiogenesis in a rabbit corneal model (Binetruy-Tornaire, R. et al., Identification of a peptide blocking vascular endothelial growth factor (VEGF)-mediated angiogenesis. EMBO J. 2000, 19:1525-1533).

Platelet-Derived Growth Factors (PDGF) and their Receptors

The PDGF family comprises PDGF-A, -B, -C and -D, which form either homo- or heterodimers (PDGF-AA, -AB, -BB, -CC, -DD. The four PDGFs are inactive in their monomeric forms. The PDGFs bind to the protein tyrosine kinase receptors PDGF receptor-α and -β. These two receptor isoforms dimerize upon binding the PDGF dimer, leading to three possible receptor combinations, namely -αα, -ββ and -αβ. The extracellular region of the receptor consists of five immunoglobulin-like domains while the intracellular part is a tyrosine kinase domain. The ligand-binding sites of the receptors are located to the three first immunoglobulin-like domains. PDGF-CC specifically interacts with PDGFR-αα and -αβ, but not with -ββ, and thereby resembles PDGF-AB. PDGF-DD binds to PDGFR-ββ with high affinity, and to PDGFR-αβ to a markedly lower extent and is therefore regarded as PDGFR-ββ specific. PDGF-AA binds only to PDGFR-αα, while PDGF-BB is the only PDGF that can bind all three receptor combinations with high affinity.

Dimerization is a prerequisite for the activation of the kinase. Kinase activation is visualized as tyrosine phosphorylation of the receptor molecules, which occurs between the dimerized receptor molecules (transphosphorylation). In conjunction with dimerization and kinase activation, the receptor molecules undergo conformational changes, which allow a basal kinase activity to phosphorylate a critical tyrosine residue, thereby "unlocking" the kinase, leading to full enzymatic activity directed toward other tyrosine residues in the receptor molecules as well as other substrates for the kinase. Expression of both receptors and each of the four PDGFs is under independent control, giving the PDGF/PDGFR system a high flexibility. Different cell types vary greatly in the ratio of PDGF isoforms and PDGFRs expressed. Different external stimuli such as inflammation, embryonic development or differentiation modulate cellular receptor expression allowing binding of some PDGFs but not others. Additionally, some cells display only one of the PDGFR isoforms while other cells express both isoforms, simultaneously or separately.

FGF2

FGFs are a family of polypeptides synthesized by a large number of cells during embryonic development and by cells of adult tissues under various pathological conditions.

FGF2 (or b-FGF) is the first and the most well-characterized of these growth factors. FGF2 is an 18 kDa protein which induces proliferation, migration and protease production by endothelial cells in culture and neovascularization in vivo. FGF2 interacts with endothelial cells by means of two classes of receptors, high-affinity receptor tyrosine kinases (FGFRs) and low-affinity heparan sulphate proteoglycan (HSPG) type receptors located at the cell surface and in extracellular matrices. Thus, FGF2 and its receptors represent very relevant targets for therapies aimed at activating or inhibiting angiogenic processes.

BIBF1120

Small-molecule tyrosine kinase inhibitors (RTKIs) represent a new class of targeted drugs in oncology. The RTKI BIBF1120 is a novel indolinone derivative that simultaneously and potently inhibits VEGF receptors 1 to 3 (VEGFR), PDGFR α and β as well as FGFR 1 to 3 tyrosine kinases with low cross-reactivity against a panel of other kinases (Kulimova et al.; Hilberg et al., 2008; Roth et al., 2009). BIBF1120 is thought to bind to the ATP binding pocket of the kinase domain, thereby interfering with the cross-autophosphorylation of the receptor homodimers. Its function was studied in three cell types contributing to angiogenesis: endothelial cells, pericytes and smooth muscle cells. In these cells BIBF1120 was shown to inhibit the mitogen-activated protein kinase (MAPK) and Akt signalling pathways, resulting in the inhibition of cell proliferation and apoptosis (Kulimova et al., 2006). A distinct pharmacodynamic feature of BIBF1120 in cell culture is the sustained pathway inhibition (up to 32 hours after 1-hour treatment), suggesting slow receptor off-kinetics. In all tumor models tested so far, BIBF1120 is highly active at well-tolerated doses. Although BIBF1120 is rapidly metabolized in vivo by methylester cleavage, resulting in a short mean residence time, once daily oral dosing is fully efficacious in xenograft models (Chaudhary et al., 2007; Hilberg et al., 2008). After passing phase I and II clinical studies in patients with advanced solid tumors (du Bois et al.; Mross K B, 2005; Von Pawel & Gatzemeier, 2007; Roth et al., 2009), BIBF1120 is now in phase III clinical trials.

Technical Problems Underlying the Present Invention

Recent advances in the generation of stable neural stem cells (NSC) from human embryonic stem cells (hESC) have provided prospects to generate donor cells for neural repair in high purity. Combined with genetic lineage selection strategies, these approaches enable the in vitro production of purified neuronal progenitors. Yet, neuronal replacement remains a challenge. In particular, transplants of hESC-derived neural precursors have been found to give rise to proliferating neural clusters rather than individually incorporating neurons.

Thus, there was a need in the prior art for promoting emigration of donor neurons from NSC grafts so that individual neurons are incorporated into the nervous system of the recipient.

Quite surprisingly, the present invention fulfils this and other needs. For example, the inventors found out in the experiments underlying the present invention that the restricted emigration of donor neurons is largely due to chemoattractive interactions between NSC-derived neurons and still undifferentiated NSCs. The inventors further found out that this autoattraction can be overcome by specific blockade of the underlying chemoattractive mechanisms, thereby reducing cluster formation and promoting widespread integration of stem cell-derived neurons into the host tissue.

The above overview does not necessarily describe all problems solved by the present invention.

SUMMARY OF THE INVENTION

In a first aspect the present invention relates to a method of treating a patient suffering from a disease or disorder of the nervous system, said method comprising administering an effective amount of neural precursor cells in combination with an effective amount of at least one inhibitor of chemoattraction.

In a second aspect the present invention relates to a method of enhancing the effectiveness of therapy with neural precursor cells, said method comprising administering an effective amount of an inhibitor of chemoattraction to a patient undergoing said therapy with neural precursor cells.

In a third aspect the present invention relates to a use of at least one inhibitor of chemoattraction in combination with neural precursor cells for the preparation of a pharmaceutical composition for the treatment of a disease or disorder of the nervous system.

In a fourth aspect the present invention relates to a use of an inhibitor of chemoattraction for the preparation of a pharmaceutical composition for enhancing the effectiveness of a therapy with neural precursor cells.

In a fifth aspect the present invention relates to a pharmaceutical composition comprising neural precursor cells and at least one inhibitor of chemoattraction.

This summary of the invention does not necessarily describe all features of the invention.

BRIEF DESCRIPTION OF THE DRAWINGS

FIG. 1A General procedure for studying cell migration by using a chemotaxis chamber. Cells are plated on the membrane of the upper well. Chemoattractants can be added to the lower well. Migration of cells from the upper well through the membrane can be measured by scraping off the remaining cells from the upper side of the membrane and counting the cells that reached the bottom side. Adopted from Erlandsson (Erlandsson, 2003).

FIG. 1B Migration of human Neurons monitored after 20 hours in culture towards either medium or plated neural stem cells derived from human embryonic stem cells (lt-hESNSC) or agarose beads pre-soaked with BDNF, EGF, SDF1, SCF, PDGF, FGF2 or VEGF. Bars represent percentage of migrated neurons (*P<0.03; Statistical significance was determined in relation to medium control).

FIG. 6A The proliferative effect was measured in a BrdU proliferation assay of lt-hESNSC in the presence of endostatin or erythropoietin. Bars represent the percentage of BrdU positive cells, cultured for 20 hours in NSC-medium, in NSC-medium with endostatin (2 µg/ml) or in NSC-medium with erythropoietin (12 IE/ml) and treated for 4.30 h with BrdU. (*P≤0.05; statistical significance was determined in relation to the control).

FIG. 6B The neurogenitic effect of endostatin or erythropoietin on lt-hESNSC was studied. Bars represent the percentage of neurons in lt-hESNSC cultured for 10 days in neuronal generation medium, in neuronal generation medium with endostatin (2 µg/ml) or in neuronal generation medium with erythropoietin (12 IE/ml). (*P≤0.05; statistical significance was determined in relation to the control).

DETAILED DESCRIPTION OF THE INVENTION

Definitions

Figure 1:
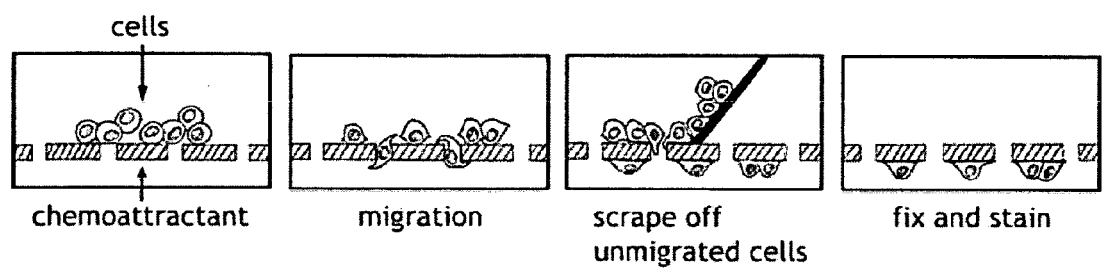
FIG. 1 Mini-chamber migration assay.
Figure 1:
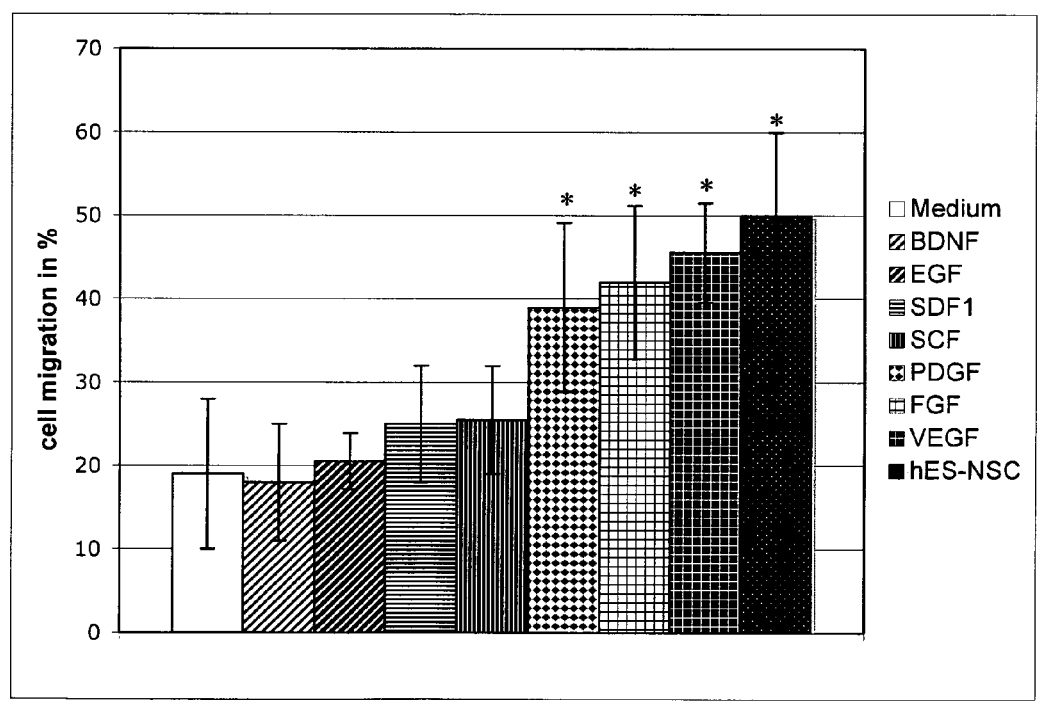

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety.

Nothing herein is to be construed as an admission that the invention is not entitled to antedate such disclosure by virtue of prior invention.

Stem Cells: In contrast to primary cells, stem cells can serve as a potentially unlimited source for the isolation of differentiated specific cell types (Poulsom R. et al., 2002; Gepstein L. 2002). Stem cells in the context of this invention refer to cells having the ability to both regenerate, i.e. being able to proliferate while still maintaining their stem cell characteristics, and to develop via a process known as "differentiation" to one or more specialized cell types, for example, cardiac muscle cells, endothelial cells, cartilage cells, bone cells, fat cells, neuronal cells, hepatocytes or insulin producing cells (Wobus A M. Mol Aspects Med. 2001 June; 22(3): 149-64).

Other examples of stem cells include, but are not limited to, stem cells derived from blood present in an umbilical cord (Sanchez-Ramos J. R., 2002), neuronal stem cells (Hitoshi S. et al., 2002; Okano H., 2002), mesenchymal stem cells originating from the bone marrow or the peripheral blood (Jiang Y. et al., 2002; Schwartz et al., 2002) in addition to stem cells derived from the skin (Toma et al., 2001), the pancreas (Means A L., 2001), the liver (Suzuki A. et al., 2001), the gut (Brittan M., 2002) or from fat tissue (Cannon B. et al., 2001). Other important sources of stem cells include embryonic germ cells (Schamblott M. I. et al., 2001), embryonic carcinoma cells (Friedrich T. D. et al., 1983; Andrews P. W. 1988), and "embryonic stem cells" (herein "ES" cells or "ESC"), which can be isolated from the inner cell mass of a blastocyst (Smith, 2001).

Thus, there are several ways to generate pluripotent stem cells useful in the present invention. For example, for the generation of ES cells through therapeutic cloning, the nucleus of a somatic stem cell is transferred into an enucleated oocyte (Wilmut et al., 1997). By isolating the inner cell mass of the developing blastocyst, ES cells with the same nuclear genome as the donor cell can be obtained. Recent studies also showed the generation of induced pluripotent stem (iPS) cells, which is a type of pluripotent stem cell artificially derived from a non-pluripotent cell such as neonatal or adult human fibroblasts, by transcription factor-based reprogramming (Takahashi & Yamanaka, 2006; Okita et al., 2007; Wernig et al., 2007). The reprogramming is typically achieved via virus-mediated gene transfer of master transcription regulators such as Oct-3/4, Sox2, Klf4, c-myc, Nanog and Lin28 (Nakagawa et al., 2008). After 3-4 weeks, small numbers of transfected cells start to become morphologically and biochemical similar to pluripotent stem cells. They can be isolated by virtue of their morphology, doubling time or a reporter gene expression. Ongoing studies are comparing iPS cells to ES cells, for identifying similarities and differences between these pluripotent stem cells. The expression of certain stem cell genes, DNA methylation patterns, doubling time, teratoma and chimera formation, and their differentiation potential are currently under investigation (Maherali et al., 2007; Wernig et al., 2007). Pluripotent stem cells generated by therapeutic cloning or by transcription factor-based reprogramming may offer major advantages for cell replacement strategies. Patient-specific pluripotent stem cell lines could be generated to prevent rejection of transplanted cells. However, there are still concerns with respect to potential therapeutic applications of such pluripotent stem cells. The current need of viral transfection of potentially oncogenic factors includes the risk of insertion mutagenesis. This can lead to the creation of cells, which might undergo uncontrolled proliferation and tumorigenesis. Even though iPS cells can be generated from mouse and human fibroblasts without the oncogenic c-myc retrovirus, the reprogramming efficiencies are thereby decreasing strongly (Marson et al., 2008; Nakagawa et al., 2008). Because of that, the method of cre-mediated excision of the integrated c-myc carrying viral genome from the iPS cells might be a useful tool for the eventual application of iPS cells in human therapies (Hanna et al., 2007). Efforts are also focusing on identifying alternatives to the viral delivery system such as using small molecules (Huangfu et al., 2008), protein transduction of reprogramming factors (Bosnali, 2008) or a plasmid-mediated system (Okita et al., 2008) to generate iPS cells.

Embryonic stem cell (ESC) lines have been established from a variety of species, including mouse (Evans M. J. & Kaufman M. H. 1981) and human (Thomson J. A. et al., 1998). ESCs are typically pluripotent stem cells, meaning they can differentiate into a variety of specific cell types (Wobus A. M., 2001; Amit M. & Itskovitz-Eldor J., 2002). Both human and murine ESC have been effectively shown to differentiate into a variety of cell-types, including cardiac muscle cells (Klug et al., 1996; Mummary C. et al., 2002; Xu C. et al., 2002), insulin-producing cells (Assady et al., 2001; Soria B., 2001; Lumelsky M. et al., 2001), neural precursor cells and neural cells (Schuldiner M. et al., 2001; Brüstle, O. et al., 1999; Okabe S. et al., 1996; Zhang S. C. et al., 2001), endothelial cells (Levenberg S., 2002) and hematopoietic cells (Kaufmann D. S., 2001). Stem cell lines refer to stem cells that are propagated in cell culture.

As used herein, the term "embryonic stem (ES) cell" refers to an undifferentiated embryonic cell having pluripotency and the ability to self-replicate. Embryonic stem cells can be established from embryonic cells isolated from embryos at the blastocyst-stage of development. Embryonic stem cells are well known to a person of ordinary skill in the art. See, e.g., WO 97/37009, entitled "Cultured Inner Cell Mass Cell-Lines Derived from Ungulate Embryos," Stice and Golueke, published Oct. 9, 1997; and Yang & Anderson, 1992. The generation of embryonic stem cells does not necessarily involve the destruction of a human embryo, since methods are known in the art, which allow the isolation of embryonic stem cells without harming the embryo which will continue to grow. In practicing the present invention it is preferable to use embryonic stem cells (e.g. for producing neural precursor cells) that have been obtained without destroying an embryo. Embryonic stem cells may be cultured with or without feeder cells. The embryonic stem cells express on their cell surface certain types of markers characteristic of the embryonic stem cells. A non-limiting example of markers for human embryonic stem cells includes but is not limited to, alkaline phosphatase, Oct4, SSEA-3, SSEA-4, TRA-1-60, TRA-1-81. In addition, a non-limiting example of markers for mouse embryonic stem cells includes but is not limited to, alkaline phosphatase, Oct4 and SSEA-1.

"Feeder cells" refer to cells of a first type that are required for cultivating cells of a second type. In the context of cultivating ES-cells, feeder cells have the function of securing the survival, proliferation, and maintenance of ES-cell pluripotency. ES-cell pluripotency can be achieved by directly co-cultivating the cells of the first with cells having the second type or, alternatively, by cultivating the cells of the first type in a medium for a certain period of time and then subsequently providing these cells to cells of the second type. Prior to transferring the medium comprising cells of the first type to the cells of the second type, all cells of the first type are preferably removed from the medium. The feeder cells can be irradiated prior to the beginning of cultivation, or undergo treatment with Mitomycin C in order to prevent any further growth of these cells. In a preferred embodiment, the feeder cells are irradiated with gamma irradiation.

As used herein, the term "neural precursor cell" refers to a cell, such as a neural stem cell or a neural progenitor cell, which has become committed to neural cell lineage, but which is not yet terminally differentiated. Thus, the "neural precursor cell" can generate progeny that are either neuronal cells (such as neuronal precursors or mature neurons) or glial cells (such as glial precursors, mature astrocytes, or mature oligodendrocytes). "Neural precursor cells" (neural stem/progenitor cells) that may be used when practicing the present invention can be generated from any type of pluripotent stem cell as described above, including without limitation ES cells, iPS cells, and spermatogenic stem cells. A "neural precursor cell" expresses characteristic markers. Such markers are expressed on the surface or informally by neural precursor cells, and include but are not limited to, polysialyated NCAM, the intermediate filament protein nestin, Vimentin, Musashi-1 and the transcription factor Pax-6. When a neural precursor cell differentiates into mature glia and neurons, nestin is gradually replaced by cell type-specific markers such as GFAP (for astrocytes) or neurofilament (for neurons). Thus, by assessing a combination of neural precursor markers such as nestin with other cell type-specific markers, one of ordinary skill in the art is able to stage the individual neural cell differentiation. Since neural stem cells can be cultured from brain tissues from mammals of any age, including adults, it is preferable for practicing the present invention to grow neural stem cells using a mammal's own tissue for autologous transplantation. Allogeneic and xenogeneic transplantations are also possible in practicing the present invention, particularly when the transplantation site is in the brain, where immunologic rejection is less severe due to the blood-brain barrier.

As used herein the term "neural cell" includes both nerve cells (i.e., neurons, e.g., uni-, bi-, or multipolar neurons) and neural cell precursors and glial cells (e.g., macroglia such as oligodendrocytes, Schwann cells, and astrocytes) and glial cell precursors. In a preferred embodiment, the neural cells for use in the invention are mammalian, e.g., human cells, murine cells, porcine cells, bovine cells, etc. obtained from embryonic stem cells.

As used herein, "a neuron" is a type of cell that carries signals between the brain and the rest of the body or within the brain. Each neuron has a cell body, an axon, and dendrites. The tip of an axon is the growth cone and is responsible for navigation. Neurons can make multiple contacts with one or more neurons. The organization of the contacts determines the overall function of the nervous system. The axons are surrounded by an insulating layer or myelin sheath formed by the Schwann cells or by oligodendrocytes.

As used herein, the term "glial cells" refers to all types of central nerve system (CNS) cells that cannot receive or transmit nerve signals. Generally, "glial cells" include astrocytes, oligodendrocytes, ependymal cells and their precursors. These glial cells perform various activities that can be regarded as performing supporting, housekeeping, and "nursing" functions within the CNS. Neuroglia have high-affinity transmitter uptake systems, voltage-dependent and transmitter-gated ion channels, and can release transmitters. Glia cell-specific markers have been identified. The markers for glia cells include but are not limited to intermediate filament typical for astrocytes (GFAP), calcium-binding protein typical for astrocytes (S100 beta), proteoglycan-component typical for glial precursors (NG2), surface antigen typical for glial precursors (A2B5), RIP for oligodendrotytes, RC2 for radial glia, 04GALC and 01GALC for oligodendrocytes, CNP, PLP, MBP (myelin components generated by oligodendrocytes).

The abbreviation lt-hESNSCs denotes long-term self-renewing rosette-type human embryonic stem cell-derived neural stem cells.

As used herein, the term "somatic cells" refers to cells that are able to undergo maturation or have already matured to one or more tissue-specific cell types. Somatic cells have the capacity to develop into numerous types of tissues, for example, bone, dental bone, cartilage, tendons, bone marrow stroma, neural tissue, skin, pancreas, liver, fat tissue, and muscle.

As used herein, the term "variant" is to be understood as a polypeptide which differs in comparison to the polypeptide from which it is derived by one or more changes in the amino acid sequence. The polypeptide from which a variant is derived is also known as the parent polypeptide. Typically a variant is constructed artificially, preferably by gene-technological means. Typically, the polypeptide from which the variant is derived is a wild-type protein or wild-type protein domain. However, the variants usable in the present invention may also be derived from homologs, orthologs, or paralogs of the parent polypeptide or from artificially constructed variants, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. The amino acid exchanges may be conservative or non-conservative. In preferred embodiments, a variant usable in the present invention differs from the protein or domain from which it is derived at least by 1, 2, 3, 4, 5, 6, 7, 8, 9, 10, 15, 20, 25, 30, 35, 40, 45, 50, 55, 60, 65, 70, 75, 80, 85, 90, 95, 100 or more amino acid exchanges, preferably conservative amino acid changes. Variants may additionally or alternatively comprise deletions of amino acids, which may be N-terminal truncations, C-terminal truncations or internal deletions or any combination of these. Such a deletion variant may be naturally occurring (e.g. splice variants) or it may be constructed artificially, preferably by gene-technological means. Typically, the protein or protein domain from which the deletion variant is derived is a wild-type protein. However, the variants of the present invention carrying deletions may also be derived from homologs, orthologs, or paralogs of the parent polypeptide or from artificially constructed variants, provided that the deletion variants exhibit at least one biological activity of the parent polypeptide. Preferably a variant has a deletion of 1, 2, 3, 4, 5, 6, 7, 8, 9, 10, 15, 20, 25, 30, 35, 40, 45, 50, 55, 60, 65, 70, 75, 80, 85, 90, 95, 100 or more amino acids at its N-terminus and/or at its C-terminus and/or internally.

A "variant" as used herein, can alternatively or additionally be characterised by a certain degree of sequence identity to the parent polypeptide from which it is derived. More precisely, a variant in the context of the present invention exhibits at least 30% sequence identity, preferably at least 40% sequence identity, preferably at least 50% sequence identity, more preferably at least 60% sequence identity, more preferably at least 70% sequence identity, more preferably at least 80% sequence identity, even more preferably at least 90% sequence identity, and most preferably at least 95% sequence identity to its parent polypeptide. Preferably, the variants of the present invention exhibit the indicated sequence identity, and preferably the sequence identity is over a continuous stretch of 20, 30, 40, 45, 50, 60, 70, 80, 90, 100 or more amino acids. The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) *Proc. Natl. Acad. Sci. USA* 90: 5873-5877), with hmmalign (HMMER package, http://lunmer.wustl.edu/) or with the CLUSTAL algorithm (Thompson, J. D., Higgins, D. G. & Gibson, T. J. (1994) *Nucleic Acids Res.* 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). Preferably, sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

"Non-conservative substitutions" or "non-conservative amino acid exchanges" are defined as exchanges of an amino acid by another amino acid listed in a different group of the six standard amino acid groups shown below:

(1) hydrophobic: Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

"Conservative substitutions" are defined as exchanges of an amino acid by another amino acid listed within the same group of the six standard amino acid groups shown above.

As used herein, the term "derivative" of a polypeptide refers to a polypeptide that has been chemically modified so that it comprises other chemical groups than the 20 naturally occurring amino acids. The polypeptide from which the derivative derives is also known as the parent polypeptide. This parent polypeptide can be a naturally occurring protein but can also be a protein variant as defined above. Chemical modifications of a polypeptide may provide advantageous properties as compared to the parent polypeptide, e.g. enhanced stability, increased biological half-life, increased water solubility. Chemical modifications applicable to the derivatives usable in the present invention include without limitation: PEGylation, glycosylation of non-glycosylated parent polypeptides, or the modification of the glycosylation pattern present in the parent polypeptide.

A "biological activity" as used herein, refers to any activity a polypeptide may exhibit, including without limitation: enzymatic activity; binding activity to another compound (e.g. binding to another polypeptide, in particular binding to a receptor); inhibitory activity (e.g. enzyme inhibitory activity); activating activity (e.g. enzyme-activating activity); or toxic effects. It is not required that the variant or derivative exhibits such an activity to the same extent as the parent polypeptide. A variant is regarded as a variant within the context of the present application, if it exhibits the relevant activity to a degree of at least 1% of the activity of the parent polypeptide. Likewise, a derivative is regarded as a derivative within the context of the present application, if it exhibits the relevant activity to a degree of at least 1% of the activity of the parent polypeptide. In preferred embodiments of the present invention, the "biological activity" is inhibition of chemoattraction. The variant or the derivative exhibits preferably at least 1%, more preferably at least 5%, more preferably at least 10%, more preferably at least 20%, more preferably at least 30%, more preferably at least 40%, more preferably at least 50%, more preferably at least 60%, more preferably at least 70%, more preferably at least 80%, more preferably at least 90% of the chemoattraction inhibitory activity of the parent polypeptide. The variant or derivative may also exhibit a higher chemoattraction inhibitory activity than the parent polypeptide, i.e. more than 100% activity. The inhibitory activity of chemoattraction can be determined by several assays known in the art, e.g. by the mini-chamber migration assay as described in Example 1.1 and illustrated in FIG. 1A or by studying migration in hippocampal rat slice cultures as described in Example 1.2.

The term "antibody", as used herein, refers to immunoglobulin molecules and immunologically active portions of immunoglobulin molecules, i.e. molecules that contain an antigen binding site that immunospecifically binds an antigen. Also comprised are immunoglobulin-like proteins that are selected through techniques including, for example, phage display to specifically bind to a target molecule. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, F(ab')₂ fragments, fragments produced by a Fab expression library, diabodies or tetrabodies (Holliger P. et al., 1993), nanobodies, anti-idiotypic (anti-Id) antibodies (including, e.g., anti-Id antibodies to antibodies of the invention), and epitope-binding fragments of any of the above.

In some embodiments "antibodies" are human antigen-binding antibody fragments and include, but are not limited to, Fab, Fab' and F(ab')₂, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also suitable for use in the present invention are antigen-binding fragments comprising any combination of variable domain(s) with a hinge region, CL, CH1, CH2, and CH3 domains.

Antibodies usable in the invention may be from any animal origin including birds and mammals. Preferably, the antibodies are human, rodent (e.g. mouse and rat), donkey, sheep rabbit, goat, guinea pig, camel, horse, or chicken. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

As used herein, a first compound (e.g. an antibody) is considered to "specifically bind" to a second compound (e.g. an antigen, such as a target protein), if it has a dissociation constant $K_D$ to said second compound of 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

As used herein, a "patient" means any mammal or bird who may benefit from a treatment with the inhibitors of chemoattraction and/or neural precursor cells described herein. Preferably, a "patient" is selected from the group consisting of laboratory animals (e.g. mouse or rat), domestic animals (including e.g. guinea pig, rabbit, donkey, sheep, goat, chicken, camel, horse, cat, or dog), or primates including human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (Hu et al., Curr. Opin., Biotechnol. 8: 148, 1997); "Serum free Media" (K. Kitano, Biotechnol. 17:73, 1991); and "Suspension Culture of Mammalian Cells" (Birch et al. Bioprocess Technol. 19: 251, 1990).

Methods directed to stem cells are described in "Teratocarcinoma and embryonic stem cells: A practical approach" (E. J. Robertson, ed., Press Ltd, 1987); "Guide to Techniques in Mouse Development" (P. M. Wassermann et al. eds., Academic Press, 1993); "Embryonic Stem Cell Differentiation in Vitro" (M. V. Wiles, Meth. Enzymol. 225: 900, 1993); "Properties and uses of Embryonic Stem Cells: Prospects for Application to Human Biology and Gene Therapy" (P. D. Rathjen et al., 1993); "Embryonic Stem Cells, Methods and Protocols" (K. Turksen ed., Humana Press, 2002) and "Human Embryonic Stem Cells" (A. Chiu und M. S. Rao, Humana Press, 2003). An overview of stem cell differentiation is provided by Robertson, Meth. Cell Biol. 75: 173, 1997 and Pedersen, Reprod. Fertil. Dev. 10: 31, 1998.

Methods relating to biological engineering techniques are described in "Bioprozesstechnik" (H. Chmiel Hrsg., Gustav Fischer Verlag 1991); "Bioreaktoren und periphere Einrichtungen. Ein Leitfaden für die Hochschulausbildung, far Hersteller und Anwender" (Winfried Storhas, Springer Verlag 1994); "Bioprocess Engineering Principles" (Pauline M. Doran, Academic Press 1997) and "Bioprocess Engineering: Basic Concepts" (Michael L-Shuler, Prentice Hall 2000). Reagents, media and kits described herein can be obtained from any known commercial provider, such as Sigma, BioRad, Stratagene, and Roche.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In the context of the present invention the term "inhibitor of chemoattraction" refers to compounds that inhibit the function of chemoattractants on neural precursor cells. Preferably the chemoattractants are VEGF, FGF2 or PDGF. To exert such an inhibitory activity the compounds may interact with VEGF, FGF2 or PDGF directly in a way, which inhibits their effects, e.g. the binding of VEGF, FGF2 and PDGF, respectively, to its receptors VEGF-receptor (VEGFR), FGF2-receptor (FGF2R) or PDGF-receptor (PDGFR); VEGF, FGF2 or PDGF secretion or the VEGF, FGF2 or PDGF pathway. Alternatively, the compound may interact with the receptor directly in a way, which inhibits the effects otherwise elicited by binding of VEGF, FGF2 or PDGF. Preferably, the compound interacts with either VEGF, FGF2, PDGF, VEGFR, FGF2R or PDGFR in a way which inhibits the binding of the chemoattractant to its respective receptor. Thus, preferably the "inhibitor of chemoattraction" is selected from a VEGF, FGF2, PDGF, VEGFR, FGF2R or PDGFR inhibitor. Such compounds are known from the prior art VEGF or VEGFR inhibitors that can be used in the context of the present invention are described in particular in US 2003/0125339; U.S. Pat. No. 6,995,162; EP 0 694 042 A1; EP 1 581 528 A1; WO 2005/027972 A2; WO 2006/086544 A2; WO 2007004749 A1, WO 2007/022101 A2; WO 2008/061647 A1; a substituted alkylamine derivative described in US2003/0125339, US2003/0225106, U.S. Pat. No. 6,995,162 or U.S. Pat. No. 6,878,714, a substituted omega-carboxyaryl diphenyl urea or derivative thereof as described in WO 00/42012, WO00/41698, US2005/0038080A1, US2003/0125359A1, US2002/0165394A1, US2001/003447A1, US2001/0016659A1, and US2002/013774A1; a pyrrole substituted 2-indolinone derivative, e.g. as described in WO 01/60814; an anilinophthalazine or derivative thereof that binds to and inhibits the activity of multiple receptor tyrosine kinases including binding to the protein kinase domain and inhibition of VEGFR, preferably as described in WO98/35958; a quinazoline derivative, e.g. as described in WO 01/32651; quinoline derivatives and quinazoline derivatives, e.g. as described in WO 00/43366; and nitrogen-containing aromatic ring derivatives, e.g. as described in WO 02/32872, all of which are herein incorporated by reference in its entirety, particularly those parts disclosing VEGF inhibitors and their structures.

Potent antagonists of the binding of FGFs to their receptor tyrosine kinases (FGFRs), such as indolizine derivatives, are described in international Patent Applications WO 2003/084956 and WO 2005/028476, and imidazo[1,5-a]pyridine derivatives in international Patent Application WO 2006/097625, all of which are herein incorporated by reference in its entirety, particularly those parts disclosing FGF antagonists and their structures.

PDGF or PDGFR inhibitors that can be used in the context of the present invention are described in particular in U.S. Pat. No. 5,238,950 A; WO 2002/067941 A2; tyrphostins; a PDGFR inhibitory compound of the 2-phenylaminopyrimidine class, preferably (N-{5-[4-(4-methyl-piperazino-methyl)-benzoylamido]-2-methylphenyl}-4-(3-pyridyl)-2-pyrimidine-amine, especially in the form of the methane sulfonate (monomesylate) salt; a PDGFR inhibitory compound of the 2-thiophen-quinoxaline class, prefer- ably 6,7-dimethoxy-2-thiophen-3-yl-quinoxaline, especially in the form of the hydrochloride salt all of which are herein incorporated by reference in its entirety, particularly those parts disclosing PDGF inhibitors and their structures.

Preferably, the "inhibitor of chemoattraction" is selected without limitation from: endostatin, angiostatin, or variants or derivatives thereof; an antibody specifically binding to VEGF (Vascular Endothelial Growth Factor); an antibody specifically binding to VEGF receptor, e.g. as described in WO 2009/120922 A2; an antibody specifically binding to FGF2 (fibroblast growth factor 2); an antibody specifically binding to FGF2 receptor; an antibody specifically binding to PDGF (platelet-derived growth factor); an antibody specifically binding to PDGF receptor, e.g. as described in WO 2009/120922 A2; or erythropoietin (EPO), or variants or derivatives thereof.

Particular preferred inhibitors of VEGFR and PDGFR are indolinones of the general formula (I):

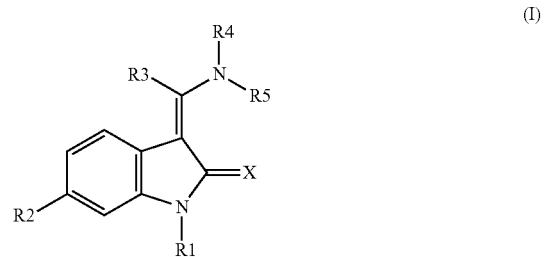

wherein

X denotes an oxygen or sulphur atom, $R_1$ denotes a hydrogen atom or a prodrug group such as a $C_{1-4}$-alkoxycarbonyl or $C_{2-4}$-alkanoyl group, $R_2$ denotes a carboxy group, a straight-chain or branched $C_{1-6}$-alkoxy-carbonyl group, a $C_{4-7}$-cycloalkoxycarbonyl or an aryloxycarbonyl group, a straight-chain or branched $C_{1-6}$-alkoxy-carbonyl group, which is terminally substituted in the alkyl moiety by a phenyl, heteroaryl, carboxy, $C_{1-3}$-alkoxy-carbonyl, aminocarbonyl, $C_{1-3}$-alkylamino-carbonyl or di-($C_{1-3}$-alkyl)-aminocarbonyl group, a straight-chain or branched $C_{2-6}$-alkoxy-carbonyl group, which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, an aminocarbonyl or methyl-aminocarbonyl group, an ethylaminocarbonyl group optionally substituted in the 2 position of the ethyl group by a hydroxy or $C_{1-3}$-alkoxy group or, if $R_4$, does not denote an aminosulphonyl-phenyl or N—($C_{3-5}$-alkyl)-$C_{1-3}$-alkylaminocarbonyl-phenyl group, it may also denote a di-($C_{1-2}$-alkyl)-aminocarbonyl group, $R_3$ denotes a hydrogen atom, a $C_{1-6}$-alkyl, $C_{3-7}$-cycloalkyl, trifluoromethyl or heteroaryl group, a phenyl or naphthyl group, a phenyl or naphthyl group mono- or disubstituted by a fluorine, chlorine, bromine or iodine atom, by a trifluoromethyl, $C_{1-3}$-alkyl or $C_{1-3}$-alkoxy group, whilst in the event of disubstitution the substituents may be identical or different and wherein the abovementioned unsubstituted as well as the mono- and disubstituted phenyl and naphthyl groups may additionally be substituted by a hydroxy, hydroxy-$C_{1-3}$-alkyl or $C_{1-3}$-alkoxy-$C_{1-3}$-alkyl group, by a cyano, carboxy, carboxy-$C_{1-3}$-alkyl, $C_{1-3}$-alkoxycarbonyl, aminocarbonyl, $C_{1-3}$-alkylaminocarbonyl or di-($C_{1-3}$-alkyl)-aminocarbonyl group, by a nitro group, by an amino, $C_{1-3}$-alkylamino, di-($C_{1-3}$-alkyl)-amino or amino-$C_{1-3}$-alkyl group, by a $C_{1-3}$-alkylcarbonylamino, N—($C_{1-3}$-alkyl)-$C_{1-3}$-alkyl-carbonylamino, $C_{1-3}$-alkylcarbonylamino-$C_{1-3}$-alkyl, N—($C_{1-3}$-alkyl)-$C_{1-3}$-alkylcarbonylamino-$C_{1-3}$-alkyl, $C_{1-3}$-alkylsulphonylamino, $C_{1-3}$-alkylsulphonylamino-$C_{1-3}$-alkyl, N—($C_{1-3}$-alkyl)-$C_{1-3}$-alkylsulphonylamino-$C_{1-3}$-alkyl or aryl-$C_{1-3}$-alkylsulphonylamino group, by a cycloalkylamino, cycloalkyleneimino, cycloalkyleneiminocarbonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group having 4 to 7 ring members in each case, whilst in each case the methylene group in position 4 of a 6- or 7-membered cycloalkyleneimino group may be replaced by an oxygen or sulphur atom, by a sulphinyl, sulphonyl, —NH or —N($C_{1-3}$-alkyl) group, or by a heteroaryl or heteroaryl-$C_{1-3}$-alkyl group, $R_4$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkylsulphonylamino, aminocarbonyl, $C_{1-3}$-alkylaminocarbonyl, di-($C_{1-3}$-alkyl)-aminocarbonyl, amino sulphonyl, $C_{1-3}$-alkyl-aminosulphonyl, di-($C_{1-3}$-alkyl)-aminosulphonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula (II)

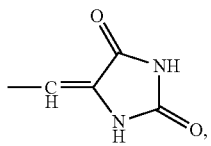

(II)

wherein the hydrogen atoms bound to a nitrogen atom may in each case be replaced independently of one another by a $C_{1-3}$-alkyl group, a $C_{1-3}$-alkoxy group, a $C_{1-3}$-alkoxy-$C_{1-3}$-alkoxy, phenyl-$C_{1-3}$-alkoxy, amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, $C_{5-7}$-cycloalkyleneimino-$C_{2-3}$-alkoxy or $C_{1-3}$-alkylmercapto group a carboxy, $C_{1-4}$-alkoxycarbonyl, aminocarbonyl, $C_{1-3}$-alkylamino-carbonyl, N—($C_{1-5}$-alkyl)-$C_{1-3}$-alkylaminocarbonyl, phenyl-$C_{1-3}$-alkylamino-carbonyl, N—($C_{1-3}$-alkyl)-phenyl-$C_{1-3}$-alkylaminocarbonyl, piperazinocarbonyl or N—($C_{1-3}$-alkyl)-piperazinocarbonyl group, a $C_{1-3}$-alkylaminocarbonyl or N—($C_{1-5}$-alkyl)-$C_{1-3}$-alkylaminocarbonyl group wherein an alkyl moiety is substituted by a carboxy or $C_{1-3}$-alkoxycarbonyl group or in the 2 or 3 position by a di-($C_{1-3}$-alkyl)amino, piperazino, N—($C_{1-3}$-alkyl)-piperazino or a 4- to 7-membered cycloalkyleneimino group, a $C_{3-7}$-cycloalkyl-carbonyl group, wherein the methylene group in the 4 position of the 6- or 7-membered cycloalkyl moiety may be substituted by an amino, $C_{1-3}$-alkylamino or di-($C_{1-3}$-alkyl)-amino group or replaced by an —NH or —N—($C_{1-3}$-alkyl) group, a 4- to 7-membered cycloalkyleneimino group wherein a methylene group linked to the imino group may be replaced by a carbonyl or sulphonyl group or the cycloalkylene moiety may be fused to a phenyl ring or one or two hydrogen atoms may each be replaced by a $C_{1-3}$-alkyl group and/or in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group substituted by the group $R_7$, wherein $R_7$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group or in a 5- to 7-membered cycloalkyl group a +$CH_2)_2$ group may be replaced by a —CO—NH group, a —$(CH_2)_3$ group may be replaced by a NH—CO—NH or —CO—NH—CO group or a —$(CH_2)_4$ group may be replaced by a —NH—CO—NH—CO group, whilst in each case a hydrogen atom bound to a nitrogen atom may be replaced by a $C_{1-3}$-alkyl group, an aryl or heteroaryl group, a hydroxy or $C_{1-3}$-alkoxy group, an amino, $C_{1-7}$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, an ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)-$C_{2-3}$-alkyl)-amino or N-(dioxolan-2-yl)-$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonyl-amino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein one or two hydrogen atoms may each be replaced by a $C_{1-3}$-alkyl group, a group of formula (III)

$$—N(R_8)—CO—(CH_2)_n—R_9 \qquad (III),$$

wherein
R$_8$ denotes a hydrogen atom or a C$_{1-3}$-alkyl group,
n denotes one of the numbers 0, 1, 2 or 3 and
R$_9$ denotes an amino, C$_{1-4}$-alkylamino, di-(C$_{1-4}$-alkyl)-amino, phenylamino, N—(C$_{1-4}$-alkyl)-phenylamino, benzylamino, N—(C$_{1-4}$-alkyl)-benzylamino or C$_{1-4}$-alkoxy group, a 4- to 7-membered cycloalkyleneimino group, whilst in each case the methylene group in the 4 position of a 6- or 7-membered cycloalkyleneimino group may be replaced by an oxygen or sulphur atom, by a sulphinyl, sulphonyl, —NH, —N(C$_{1-3}$-alkyl), —N(phenyl), —N(C$_{1-3}$-alkyl-carbonyl) or —N(benzoyl) group, or, if n denotes one of the numbers 1, 2 or 3, it may also denote a hydrogen atom, a group of formula (IV)

$$—N(R_{10})—(CH_2)_m—(CO)_o—R_{11} \qquad (IV),$$

wherein
R$_{10}$ denotes a hydrogen atom, a C$_{1-3}$-alkyl group, a C$_{1-3}$-alkylcarbonyl, arylcarbonyl, phenyl-C$_{1-3}$-alkyl-carbonyl, C$_{1-3}$-alkylsulphonyl, arylsulphonyl or phenyl-C$_{1-3}$ alkylsulphonyl group,
m denotes one of the numbers 1, 2, 3 or 4,
o denotes the number 1 or, if m denotes one of the numbers 2, 3 or 4, o may also denote the number 0 and
R$_{11}$ denotes an amino, C$_{1-4}$-alkylamino, di-(C$_{1-4}$-alkyl)-amino, phenylamino, N—(C$_{1-4}$-alkyl)-phenylamino, benzylamino, N—(C$_{1-4}$-alkyl)-benzylamino, C$_{1-4}$-alkoxy or C$_{1-3}$ alkoxy-C$_{1-3}$-alkoxy group, a di-(C$_{1-4}$-alkyl)-amino-C$_{1-4}$-alkyl amino group optionally substituted in the 1 position by a C$_{1-3}$-alkyl group or a 4- to 7-membered cycloalkyleneimino group, wherein the cycloalkylene moiety may be fused to a phenyl ring or in each case the methylene group in the 4 position of a 6- or 7-membered cycloalkylene-imino group may be replaced by an oxygen or sulphur atom, by a sulphinyl, sulphonyl, —NH, —N(C$_{1-3}$-alkyl), —N(phenyl), carbonyl) or —N(benzoyl) group, a C$_{4-7}$-cycloalkylamino, C$_{4-7}$-cycloalkyl-C$_{1-3}$-alkylamino or C$_{4-7}$-cycloalkenylamino group wherein position 1 of the ring is not involved in the double bond and wherein the abovementioned groups may each additionally be substituted at the amino-nitrogen atom by a C$_{5-7}$-cycloalkyl, C$_{2-4}$-alkenyl or C$_{1-4}$-alkyl group, a 4- to 7-membered cycloalkyleneimino group, wherein the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, C$_{1-3}$-alkyl, C$_{1-3}$-alkoxy or amino group, and/or one or two hydrogen atoms may each be replaced by a C$_{1-3}$-alkyl, C$_{5-7}$-cycloalkyl or phenyl group and/or the methylene group in the 3 position of a 5-membered cycloalkyleneimino group may be substituted by a hydroxy, hydroxy-C$_{1-3}$-alkyl, C$_{1-3}$-alkoxy or C$_{1-3}$-alkoxy-C$_{1-3}$-alkyl group, the methylene group in the 3 or 4 position of a 6- or 7-membered cycloalkyleneimino group may in each case be substituted by a hydroxy, hydroxy-C$_{1-3}$-alkyl, C$_{1-3}$-alkoxy, C$_{1-3}$-alkoxy-C$_{1-3}$-alkyl, carboxy, C$_{1-4}$-alkoxycarbonyl, aminocarbonyl, C$_{1-3}$-alkylaminocarbonyl, di-(C$_{1-3}$-alkyl)-aminocarbonyl, phenyl-C$_{1-3}$-alkylamino or N—(C$_{1-3}$-alkyl)-phenyl-C$_{1-3}$-alkylamino group or may be replaced by an oxygen or sulphur atom, by a sulphinyl, sulphonyl, —NH, —N(C$_{1-3}$-alkyl, —N(phenyl), —N(C$_{1-3}$-alkyl-carbonyl)-, —N(C$_{1-4}$-hydroxy-carbonyl), —N(C$_{1-4}$-alkoxy-carbonyl)-, —N (benzoyl)- or —N(phenyl-C$_{1-3}$-alkyl-carbonyl group,
wherein a methylene group linked to an iminonitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the iminonitrogen atom may each be replaced by a carbonyl group or R$_6$ denotes a C$_{1-4}$-alkyl group which is substituted by a carboxy, C$_{1-3}$-alkoxycarbonyl, aminocarbonyl, C$_{1-3}$-alkylaminocarbonyl or di-(C$_{1-3}$-alkyl)-aminocarbonyl group or by a 4- to 7-membered cycloalkyleneiminocarbonyl group, an N—(C$_{1-3}$-alkyl)-C$_{2-4}$-alkanoylamino group which is additionally substituted in the alkyl moiety by a carboxy or C$_{1-3}$-alkoxycarbonyl group, a group formula (V)

$$—N(R_{12})—CO—(CH_2)_p—R_{13} \qquad (V),$$

wherein
R$_{12}$ denotes a hydrogen atom, a C$_{1-6}$-alkyl or C$_{3-7}$-cycloalkyl group or a C$_{1-3}$-alkyl group terminally substituted by a phenyl, heteroaryl, trifluoromethyl, hydroxy, C$_{1-3}$-alkoxy, aminocarbonyl, C$_{1-4}$-alkylamino-carbonyl, di-(C$_{1-4}$-alkyl)-amino-carbonyl, C$_{1-3}$-alkyl-carbonyl, C$_{1-3}$-alkylsulphonylamino, N—(C$_{1-3}$-alkyl)-C$_{1-3}$-alkyl-sulphonylamino, C$_{1-3}$-alkyl-aminosulphonyl or di-(C$_{1-3}$-alkyl)aminosulphonyl group and
p denotes one of the numbers 0, 1, 2 or 3 and
R$_{13}$ assumes the meanings of the abovementioned group R$_7$ or, if p denotes one of the numbers 1, 2 or 3, it may also denote a hydrogen atom, a group of formula (VI)

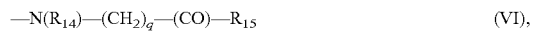

$$—N(R_{14})—(CH_2)_q—(CO)—R_{15} \qquad (VI),$$

wherein
R$_{14}$ denotes a hydrogen atom, a C$_{1-4}$-alkyl group, a C$_{1-3}$-alkylcarbonyl, arylcarbonyl, phenyl-C$_{1-3}$-alkyl carbonyl, heteroarylcarbonyl, heteroaryl-C$_{1-3}$-alkylcarbonyl, C$_{1-3}$-alkylsulphonyl, arylsulphonyl, phenyl-C$_{1-3}$-alkylsulphonyl, heteroarylsulphonyl or heteroaryl-C$_{1-3}$-alkyl-sulphonyl group,
q denotes one of the numbers 1, 2, 3 or 4,
r denotes the number 1 or, if q is one of the numbers 2, 3 or 4, it may also denote the number 0 and
R$_{15}$ assumes the meanings of the abovementioned group R$_7$ a group of formula (VII)

$$—N(R_{16})—SO_2-R17 \qquad (VII),$$

wherein
R$_{16}$ denotes a hydrogen atom or a C$_{1-8}$-alkyl group optionally terminally substituted by a cyano, trifluoromethyl-carbonylamino or N—(C,-,-alkyl)-trifluoromethyl-carbonylamino group and
R$_{17}$ denotes a C$_{1-3}$-alkyl group, an amino group substituted by a di-(C$_{1-3}$-alkyl)-amino-C$_{1-3}$-alkyl-carbonyl or di-(C$_{1-3}$-alkyl)-amino-C$_{1-3}$-alkyl-sulphonyl group and a di-(C$_{1-3}$-alkyl)-aminocarbonyl-C$_{1-3}$-alkyl group, or an N—($C_{1-3}$-alkyl)-$C_{1-5}$-alkylsulphonyl amino or N—($C_{1-3}$-alkyl)-phenylsulphonylamino group wherein the alkyl moiety is additionally substituted by a cyano or carboxy group wherein all the single-bonded or fused phenyl groups contained in the groups mentioned under R, may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by an aryl group is meant a phenyl or naphthyl group optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and by a heteroaryl group is meant a monocyclic 5- or 6-membered heteroaryl group optionally substituted by a $C_{1-3}$-alkyl group in the carbon skeleton, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl orphenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused phenyl ring, some or all of the hydrogen atoms in the abovementioned alkyl and alkoxy groups or in the alkyl moieties contained in the above-defined groups of formula I optionally being replaced by fluorine atoms, the saturated alkyl and alkoxy moieties with more than 2 carbon atoms which are present in the groups defined hereinbefore also include the branched isomers thereof, such as for example the isopropyl, tert-butyl, isobutyl group, unless otherwise stated, and additionally the hydrogen atom of any carboxy group present or a hydrogen atom bound to a nitrogen atom, e.g. a hydrogen atom of an amino, alkylamino or imino group or a saturated N-heterocycle such as the piperidinyl group, may each be replaced by a group which can be cleaved in vivo.

By a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl; $C_{1-3}$-alkoxy-$C_{2-4}$-alkoxy-$C_{2-4}$-alkoxycarbonoyl or $R_eCO$—O—($R_fCR^g$)—O—CO group wherein $R_e$ denotes a $C_{1-3}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_eCO$—O—($R_fCR_g$)—O group wherein $R_e$ to $R_g$ are as hereinbefore defined, wherein additionally the amino group may be a phthalimido group, whilst the abovementioned ester groups may also be used as a group which can be converted in vivo into a carboxy group.

With respect to the particularly preferred VEGFR and PDGFR inhibitors of formula (I) and their production specific reference is made to the compounds and preferred compounds and the methods of their production indicated in WO 01/27081 A1, which are usable in the context of the present invention and which are specifically incorporated herein by reference. Particularly preferred compounds are the following:

(1) 3-Z-(1-anilino-1-phenyl-methylene)-6-ethoxycarbony 2-indolinone (2) 3-Z-[1-(4-nitro-anilino)-1-phenyl-methylene]-6-ethoxycarbonyl-2-indolinone (2) 3-Z-[1-(4-fluoro-anilino)-1-phenyl-methylene]-6-ethoxycarbonyl-2-indolinone (4) 3-Z-[1-(4-chloro-anilino)-1-phenyl-methylene]-6-ethoxycarbonyl-2-indolinone (5) 3-Z-[1-(4-iodo-anilino)-1-phenyl-methylene]-6-ethoxycarbonyl-2-indolinone (6) 3-Z-[1-(4-cyano-anilino)-1-phenyl-methylene]-6-ethoxycarbonyl-2-indolinone (7) 3-Z-[1-(4-methoxy-anilino)-1-phenyl-methylene]-6-ethoxycarbonyl-2-indolinone (8) 3-Z-[1-(4-ethoxy-anilino)-1-phenyl-methylene]-6-ethoxycarbonyl-2-indolinone (9) 3-Z-[1-(4-trifluoromethyl-anilino)-1-phenyl-methylene]-6-ethoxycarbonyl-2-indolinone

(11) 3-Z-[1-(4-methylmercapto-anilino)-1-phenyl-methylene]-6-ethoxycarbonyl-2-indolinone

(12) 3-Z-[1-(4-aminomethyl-anilino)-1-phenyl-methylene]-6-ethoxycarbonyl-2-indolinone

(13) 3-2-[1-(4-(isopropylaminomethyl)-anilino)-1-phenyl-methylene]-6-ethoxycarbonyl-2-indolinone

(14) 3-Z-[1-(4-(anilinomethyl)-anilino)-1-phenyl-methylene]-6-ethoxycarbonyl-2-indolinone

(15) 3-Z-[1-(4-(propylaminomethyl)-anilino)-1-phenylmethylene]-6-ethoxycarbonyl-2-indolinone

(16) 3-Z-[1-(4-(butylaminomethyl)-anilino)-1-phenylmethylene]-6-ethoxycarbonyl-2-indolinone

(17) 3-Z-[1-(4-(isobutylaminomethyl)-anilino)-1-phenylmethylene]-6-ethoxycarbonyl-2-indolinone

(18) 3-Z-[1-(4-(cyclohexylaminomethyl)-anilino)-1-phenyl-methylene]-6-ethoxycarbonyl-2-indolinone

(19) 3-Z-[1-(4-(benzylaminomethyl)-anilino)-1-phenylmethylene]-6-ethoxycarbonyl-2-indolinone

(20) 3-Z-[1-(4-((N-ethyl-N-methyl-amino)-methyl)-anilino)-1-phenyl-methylene]-6-ethoxycarbonyl-2-indolinone

(21) 3-Z-[1-(4-((N-methyl-N-propyl-amino)-methyl)-anilino)-1-phenyl-methylene]-6-ethoxycarbonyl-2-indolinone

(22) 3-Z-[1-(4-((N-isopropyl-N-methyl-amino)-methyl)-anilino)-1-phenyl-methylene]-6-ethoxy-carbonyl-2-indolinone
(23) 3-Z-[1-(4-((N-ethyl-N-propyl-amino)-methyl)-anilino)-1-phenyl-methylene]-6-ethoxycarbonyl-2-indolinone
(24) 3-Z-[1-(4-((N-ethyl-N-isopropyl-amino)-methyl)-anilino)-1-phenyl-methylene]-6-ethoxycarbonyl-2-indolinone
(25) 3-Z-[1-(4-(dipropylaminomethyl)-anilino)-1-phenylmethylene]-6-ethoxycarbonyl-2-indolinone
(26) 3-Z-[1-(4-(diisopropylaminomethyl)-anilino)-1-phenylmethylene]-6-ethoxycarbonyl-2-indolinone
(27) 3-Z-[1-(4-((N-benzyl-N-ethyl-amino)-methyl)-anilino)-1-phenyl-methylene]-6-ethoxycarbonyl-2-indolinone
(28) 3-Z-[1-(4-(dibenzylaminomethyl)-anilino)-1-phenyl-methylene]-6-ethoxycarbonyl-2-indolinon
(29) 3-Z-[1-(4-(3,6-dihydro-2H-pyridin-1-yl-methyl)-anilino)-1-phenyl-methylene]-6-ethoxy-carbonyl-2-indolinone
(30) 3-Z-[1-(4-(3,5-dimethyl-piperidin-1-y-methyl)-anilino)-1-phenyl-methylene]-6-ethoxycarbonyl-2-indolinone
(31) 3-Z-[1-(4-(azepan-1-yl-methyl)-anilino)-1-phenymethylene]-6-ethoxycarbonyl-2-indolinone
(32) 3-Z-[1-(4-(piperazin-1-yl-methyl)-anilino)-1-phenyl-methylene]-6-ethoxycarbonyl-2-indolinone
(33) 3-Z-[1-(4-(morpholin-4-yl-methyl)-anilino)-1-phenyl-methylene]-6-ethoxycarbonyl-2-indolinone
(34) 3-Z-[1-(4-(thiomorpholin-4-yl-methyl)-anilino)-1-phenyl-methylene]-6-ethoxycarbonyl-2-indolinone
(35) 3-Z-[1-(4-(1-oxo-thiomorpholin-4-yl-methyl)-anilino)-1-phenyl-methylene]-6-ethoxycarbonyl-2-indolinone
(36) 3-Z-[1-(4-(1,1-dioxo-thiomorpholin-4-yl-methyl)-anilino)-1-phenyl-methylene]-6-ethoxy carbonyl-2-indolinone
(37) 3-2-[1-(4-(acetylamino-methyl)-anilino)-1-phenylmethylene]-6-ethoxycarbonyl-2-indolinone
(38) 3-Z-[1-(4-(2-amino-ethyl)-anilino)-1-phenyl-methylene]-6-ethoxycarbonyl-2-indolinone
(39) 3-Z-[1-(4-(2-methyl-amino-ethyl)-anilino)-1-phenyl-methylene]-6-ethoxycarbonyl-2-indolinone
(40) 3-Z-[1-(4-(2-ethylamino-ethyl)-anilino)-1-phenyl-methylene]-6-ethoxycarbonyl-2-indolinone
(41) 3-Z-[1-(4-(2-diethylamino-ethyl)-anilino)-1-phenyl-methylene]-6-ethoxycarbonyl-2-indolinone
(42) 3-Z-[1-(4-(2-piperidin-1-yl-ethyl)-anilino)-1-phenyl-methylene]-6-ethoxycarbonyl-2-indolinone
(43) 3-Z-[1-(4-(2-acetylamino-ethyl)-anilino)-1-phenyl-methylene]-6-ethoxycarbonyl-2-indolinone
(44) 3-Z-[1-(4-(3-amino-propyl)-anilino)-1-phenyl-methylene]-6-ethoxycarbonyl-2-indolinone
(45) 3-Z-[1-(4-(3-dimethyl-amino-propyl)-anilino)-1-phenyl-methylene]-6-ethoxycarbonyl-2-indolinone
(46) 3-Z-[1-(4-(N-aminomethylcarbonyl-N-methyl-amino)-anilino)-1-phenyl-methylene]-6-ethoxy carbonyl-2-indolinone
(47) 3-Z-[1-(4-(N-methyl-aminomethylcarbonyl-N-methyl-amino)-anilino)-1-phenyl-methylene]-6-ethoxycarbonyl-2-indolinone
(48) 3-Z-[1-(4-(N-ethylaminomethylcarbonyl-N-methyl-amino)-anilino)-1-phenyl-methylene]-6-ethoxycarbonyl-2-indolinone
(49) 3-Z-[1-(4-(N-diethylaminomethylcarbonyl-N-methyl-amino)-anilino)-1-phenyl-methylene]-6-ethoxycarbonyl-2-indolinone
(50) 3-Z-[1-(4-(N-(piperidin-1-yl-methylcarbonyl)-N-methyl-amino)-anilino)-1-phenyl-methylene]-6-ethoxy-carbonyl-2-indolinone
(51) 3-Z-[1-(4-(N-(morpholin-4-yl-methylcarbonyl)-methyl-lamino)-anilino)-1-phenyl-methylene]-6-ethoxy-carbonyl-2-indolinone
(52) 3-Z-[1-(4-(N-(piperazin-1-yl-methylcarbonyl)-N-methyl-aminol-anilino)-1-phenyl-methylene]-6-ethoxy-carbonyl-2-indolinone
(53) 3-Z-[1-(4-(N-(2-amino-ethyl carbonyl)-N-methyl-amino)-anilino)-1-phenyl-methylene]-6-ethoxycarbonyl-2-indolinone
(54) 3-Z-[1-(4-(N-(2-methyl-amino-ethylcarbonyl)-N-methyl-amino)-anilino)-1-phenyl-methylene]-6-ethoxy-carbonyl-2-indolinone
(55) 3-Z-1 1-(4-(N-(2-diethyl amino-ethylcarbonyl)-N-methyl-amino)-anilino)-1-phenyl-methylene]-6-ethoxy-carbonyl-2-indolinone
(56) 3-Z-[1-(4-(N-acetyl-N-(2-aminoethyl)-amino)-anilino)-1-phenyl-methylene]-6-ethoxycarbonyl-2-indolinone
(57) 3-Z-[1-(4-(N-acetyl-N-(2-methyl-amino-ethyl)-amino)-anilino)-1-phenyl-methylene]-6-ethoxy carbonyl-2-indolinone
(58) 3-Z-[1-(4-(N-acetyl-N-(2-methyl-amino-propyl)-amino)-anilino)-1-phenyl-methylene]-6-ethoxy carbonyl-2-indolinone
(59) 3-Z-[1-(4-(N-acetyl-N-(2-piperidin-1-yl-ethyl)-amino)-anilino)-1-phenyl-methylene]-6-ethoxy carbonyl-2-indolinone
(60) 3-Z-[1-(4-(N-acetyl-N-(aminocarbonylmethyl)-amino)-anilino)-1-phenyl-methylene]-6-ethoxy carbonyl-2-indolinone
(61) 3-Z-[1-(4-(N-acetyl-N-(dimethyl-aminocarbonylmethyl)-amino)-anilino)-1-phenyl-methylene]-6-ethoxy-carbonyl-2-indolinone
(62) 3-Z-[1-(4-(N-acetyl-N-(piperidin-1-yl-carbonylmethyl)-amino)-anilino)-1-phenyl-methylene]-6-ethoxy-carbonyl-2-indolinone
(63) 3-Z-[1-(4-(N-methyl-N-(aminocarbonyl)-amino)-anilino)-1-phenyl-methylene]-6-ethoxy carbonyl-2-indolinone
(64) 3-Z-[1-(4-(N-methyl-N-(methyl-aminocarbonyl)-amino)-anilino)-1-phenyl-methylene]-6-ethoxy carbonyl-2-indolinone
(65) 3-Z-[1-(4-(N-methyl-N-(dimethyl-aminocarbonyl)-amino)-anilino)-1-phenyl-methylene]-6-ethoxy carbonyl-2-indolinone
(66) 3-z-[1-(4-(N-methyl-N-(piperidin-1-yl-carbonyl)-amino)-anilino)-1-phenyl-methylene]-6-ethoxy carbonyl-2-indolinone
(67) 3-Z-[1-(4-(N-(2-aminoethyl)-N-methyl sulphonyl-amino)-anilino)-1-phenyl-methylene]-6-ethoxy carbonyl-2-indolinone
(68) 3-2-[1-(4-(N-(2-methyl-amino-ethyl)-N-methyl sulphonyl-amino)-anilino)-1-phenyl-methylene]-6-ethoxy-carbonyl-2-indolinone
(69) 3-2-[1-(4-(N-(2-ethylamino-ethyl)-N-methyl sulphonyl-amino)-anilino)-1-phenyl-methylene]-6-ethoxycarbonyl-2-indolinone
(70) 3-2-[1-(4-(N-(2-diethylamino-ethyl)-N-methyl sulphonyl-amino)-anilino)-1-phenyl-methylene]-6-ethoxycarbonyl-2-indolinone
(71) 3-2-[1-(4-(N-(2-pyrrolidin-1-yl-ethyl)-N-methylsulphonyl amino)-anilino)-1-phenyl-methylene]-6-ethoxycarbonyl-2-indolinone

(72) 3-Z-[1-(4-(N-(2-piperidin-1-yl-ethyl)-N-methyl sulphonylamino)-anilino)-1-phenyl-methylene]-6-ethoxycarbonyl-2-indolinone
(73) 3-2-[1-(4-(N-(2-piperazin-1-yl-ethyl)-N-methyl sulphonylamino)-anilino)-1-phenyl-methylene]-6-ethoxycarbonyl-2-indolinone
(74) 3-Z-[1-(4-(N-(2-(morpholin-4-yl)-ethyl)-N-methyl sulphonyl-amino)-anilino)-1-phenyl-methylene]-6-ethoxycarbonyl-2-indolinone
(75) 3-Z-[1-(4-(N-(aminocarbonylmethyl)-N-methyl sulphonylamino)-anilino)-1-phenyl-methylene]-6-ethoxycarbonyl-2-indolinone
(76) 3-Z-[1-(4-(N-(methyl-aminocarbonylmethyl)-N-methyl sulphonyl-amino)-anilino)-1-phenyl-methylene]-6-ethoxycarbonyl-2-indolinone
(77) 3-Z-[1-(4-(N-(ethylaminocarbonylmethyl)-N-methyl sulphonyl-amino)-anilino)-1-phenyl-methylene]-6-ethoxycarbonyl-2-indolinone
(78) 3-Z-[1-(4-(N—(N-(2-dimethyl-amino-ethyl)-N-methyl-amino-carbonylmethyl)-N-methyl sulphonyl-amino)-anilino)-1-phenylmethylene]-6-ethoxycarbonyl-2-indolinone
(79) 3-Z-[1-(4-(N-(diethylaminocarbonylmethyl)-N-methyl sulphonyl-amino)-anilino)-1-phenyl-methylene]-6-ethoxycarbonyl-2-indolinone
(80) 3-Z-[1-(4-(N-(pyrrodin-1-yl-carbonylmethyl)-N-methyl sulphonyl-amino)-anilino)-1-phenyl-methylene]-6-ethoxycarbonyl-2-indolinone
(81) 3-Z-[1-(4-(N-(piperidin-1-yl-carbonylmethyl)-N-methylsulphonyl-amino)-anilino)-1-phenyl-methylene]-6-ethoxycarbonyl-2-indolinone
(82) 3-Z-[1-(4-(N-(piperazin-1-yl-carbonylmethyl)-N-methyl sulphonyl-amino)-anilino)-1-phenyl-methylene]-6-ethoxycarbonyl-2-indolinone
(83) 3-Z-[1-(4-(N-((morpholin-4-yl)-carbonylmethyl)-N-methyl sulphonyl-amino)-anilino)-1-phenyl-methylene]-6-ethoxycarbonyl-2-indolinone
(84) 3-Z-[1-(4-(2-dimethyl-amino-ethoxy)-anilino)-1-phenyl-methylene]-6-ethoxycarbonyl-2-indolinone
(85) 3-Z-[1-(4-(3-dimethyl-amino-propoxy)-anilino)-1-phenyl-methylene]-6-ethoxycarbonyl-2-indolinone
(86) 3-Z-[1-(4-(aminocarbonylmethyl)-anilino)-1-phenyl-methylene]-6-ethoxycarbonyl-2-indolinone
(87) 3-Z-[1-(4-(2-aminocarbonyl ethyl)-anilino)-1-phenyl-methylene]-6-ethoxycarbonyl-2-indolinone
(88) 3-Z-[1-(4-(pyridine-2-yl)-anilino)-1-phenyl-methylene]-6-ethoxycarbonyl-2-indolinone
(89) 3-Z-[1-(4-(pyridine-3-yl)-anilino)-1-phenyl-methylene]-6-ethoxycarbonyl-2-indolinone
(90) 3-Z-[1-(4-(pyridine-4-yl)-anilino)-1-phenyl-methylene]-6-ethoxycarbonyl-2-indolinone
(91) 3-Z-[1-(4-(N-acetyl-N-methyl-amino)-anilino)-1-phenyl-methylene]-6-ethoxycarbonyl-2-indolinone
(92) 3-Z-[1-(4-(N-ethylcarbonyl-N-(dimethylaminocarbonyl-methyl)-amino)-anilino)-1-phenyl-methylene]-6-ethoxycarbonyl-2-indolinone
(93) 3-Z-[1-(carbamoylmethyl-anilino)-1-phenyl-methylene]-6-ethoxycarbonyl-2-indolinone
(94) 3-Z-[1-(4-dimethyl carbamoylmethyl-anilino)-1-phenyl-methylene]-6-ethoxycarbonyl-2-indolinone
(95) 3-Z-[1-(4-(piperidin-1-yl-methyl)-anilino)-1-phenyl-methylene]-6-ethoxycarbonyl-2-indolinone
(96) 3-Z-[1-(4-(piperidin-1-yl-methyl)-anilino)-propylidene]-6-ethoxycarbonyl-2-indolinone
(97) 3-Z-[1-(4-(piperidin-1-yl-methyl)-anilino)-butylidene]-6-ethoxycarbonyl-2-indolinone
(98) 3-Z-[1-(4-(N-(3-dimethyl-amino-propyl)-N-acetyl-amino)-anilino)-methylene]-6-ethoxycarbonyl-2-indolinone
(99) 3-Z-[1-(4-(N-(3-dimethyl-amino-propyl)-N-acetyl-amino)-anilino)-ethylidene]-6-ethoxycarbonyl-2-indolinone
(100) 3-Z-[1-(4-(N-(3-dimethyl-amino-propyl)-N-acetyl-amino)-anilino)-propylidene]-6-ethoxycarbonyl-2-indolinone
(101) 3-Z-[1-(4-(N-(3-dimethyl-amino-propyl)-N-acetyl-amino)-anilino)-butylidene]-6-ethoxycarbonyl-2-indolinone
(102) 3-Z-[1-(4-(N-(2-dimethyl-amino-ethyl)-N-methylsulphonylamino)-anilino)-methylene]-6-ethoxycarbonyl-2-indolinone
(103) 3-Z-[1-(4-(N-(2-dimethyl-amino-ethyl)-N-methylsulphonylamino)-anilino)-propylidene]-6-ethoxycarbonyl-2-indolinone
(104) 3-Z-[1-(4-(N-(2-dimethyl-amino-ethyl)-N-methylsulphonylamino)-anilino)-butylidene]-6-ethoxycarbonyl-2-indolinone
(105) 3-Z-[1-(4-tetrazol-5-yl-anilino)-methylene]-6-ethoxycarbonyl-2-indolinone
(106) 3-Z-[1-(4-tetrazol-5-yl-anilino)-ethylidene]-6-ethoxycarbonyl-2-indolinone
(107) 3-Z-[1-(4-tetrazol-5-yl-anilino)-propylidene]-ethoxycarbonyl-2-indolinone
(108) 3-Z-[1-(4-tetrazol-5-yl-anilino)-butylidene]-6-ethoxycarbonyl-2-indolinone
(109) 3-Z-E1-(4-carboxy-anilino)-methylene]-6-ethoxycarbonyl-2-indolinone
(110) 3-Z-[1-(4-carboxy-anilino)-propylidene]-6-ethoxycarbonyl-2-indolinone
(111) 3-2-[1-(4-carboxy-anilino)-butylidene]-6-ethoxycarbonyl-2-indolinone
(113) 3-Z-[1-(4-(N-(4-dimethyl-amino-butyryl)-N-dimethyl-aminocarbonylmethyl-amino)-anilino)-1-phenylmethylene]-6-ethoxycarbonyl-2-indolinone
(112) 3-Z-[1-(4-(N-(3-dimethyl-amino-propionyl)-N-dimethyl-aminocarbonylmethyl-amino)-anilino)-1-phenyl-methylene]-6-ethoxycarbonyl-2-indolinone
(113) 3-Z-[1-(4-(N-(4-dimethyl-amino-butyryl)-N-dimethyl-aminocarbonylmethyl-amino)-anilino)-1-phenyl-methylene]-6-ethoxycarbonyl-2-indolinone
(114) 3-Z-[1-(4-(N-dimethyl-aminocarbonylmethyl-N-(2-dimethyl-amino-ethylsulphonyl)-amino)-anilino)-1-phenylmethylene]-6-ethoxycarbonyl-2-indolinone
(115) 3-Z-[1-(4-(N-dimethyl-aminocarbonylmethyl-N-(3-dimethyl-amino-propylsulphonyl)-amino)-anilino)-1-phenylmethylene]-6-ethoxycarbonyl-2-indolinone
(116) 3-Z-[1-(4-((2-hydroxy-ethyl)-amino-methyl)-anilino)-1-phenyl-methylene]-6-ethoxycarbonyl-2-indolinone
(117) 3-Z-[1-(4-((2-methoxy-ethyl)-amino-methyl)-anilino)-1-phenyl-methylene]-6-ethoxycarbonyl-2-indolinone
(118) 3-Z-[1-(4-((2-dimethyl-amino-ethyl)-amino-methyl)-anilino)-1-phenyl-methylene]-6-ethoxycarbonyl-2-indolinone
(119) 3-2-[1-(4-((3-dimethyl-amino-propyl)-amino-methyl)-anilino)-1-phenyl-methylene]-6-eth0~ylcarbonyl-2-indolinone
(120) 3-Z-[1-(4-((N-tert.butoxycarbonyl-2-amino-ethyl)-amino-methyl)-anilino)-1-phenyl-methylene]-6-ethoxycarbonyl-2-indolinone
(121) 3-Z-[1-(4-((N-tert.butoxycarbonyl-3-amino-propyl)-amino-methyl)-anilino)-1-phenyl-methylene]-6-ethoxycarbonyl-2-indolinone (122) 3-Z-[1-(4-((2-amino-ethyl)-amino-methyl)-anilino)-1-phenyl-methylene]-6-ethoxycarbonyl-2-indolinone
(123) 3-Z-[1-(4-((2-amino-propyl)-amino-methyl)-anilino)-1-phenyl-methylene]-6-ethoxycarbonyl-2-indolinone
(124) 3-Z-[1-(4-((2-acethylamino-ethyl)-amino-methyl)-anilino)-1-phenyl-methylene]-6-ethoxycarbonyl-2-indolinone
(125) 3-Z-[1-(4-((3-acetylamino-propyl)-amino-methyl)-anilino)-1-phenyl-methylene]-6-ethoxycarbonyl-2-indolinone
(126) 3-Z-[1-(4-((2-methylsulphonylamino-ethyl)-amino-methyl)-anilino)-1-phenyl-methylene]-6-ethoxycarbonyl-2-indolinone
(127) 3-Z-[1-(4-((3-methylsulphonylamino-propyl)-amino-methyl)-anilino)-1-phenyl-methylene]-6-ethoxycarbonyl-2-indolinone
(128) 3-Z-[1-(4-(N—(N-tert-butoxycarbonyl-2-amino-ethyl)-N-methyl-amino-methyl)-anilino)-1-phenyl-methylene]-6-ethoxycarbonyl-2-indolinone
(129) 3-Z-[1-(4-(N-(2-amino-ethyl)-N-methyl-amino-methyl)-anilino)-1-phenyl-methylene]-6-ethoxycarbonyl-2-indolinone
(130) 3-Z-[1-(4-(N-(2-acetylamino-ethyl)-N-methyl-aminomethyl)-anilino)-1-phenyl-methylene]-6-ethoxycarbonyl-2-indolinone
(131) 3-Z-[1-(4-(N-(2-methylsulphonylamino-ethyl)-N-methyl-amino-methyl)-anilino)-1-phenyl-methylene]-6-ethoxycarbonyl-2-indolinone
(132) 3-Z-[1-(4-(carboxymethyl-amino-methyl)-anilino)-1-phenyl-methylene]-6-ethoxycarbonyl-2-indolinone
(133) 3-Z-[1-(4-(ethoxycarbonylmethyl-amino-methyl)-anilino)-1-phenyl-methylene]-6-ethoxycarbonyl-2-indolinone
(134) 3-Z-[1-(4-(carbamoylmethyl-amino-methyl)-anilino)-1-phenyl-methylene]-6-ethoxycarbonyl-2-indolinone
(135) 3-Z-[1-(4-(dimethylcarbamoyl-methyl-amino-methyl)-anilino)-1-phenyl-methylene]-6-ethoxycarbonyl-2-indolinone
(136) 3-Z-[1-(4-(methylcarbamoyl-methyl-amino-methyl)-anilino)-1-phenyl-methylene]-6-ethoxycarbonyl-2-indolinone
(137) 3-Z-[1-(4-(N-dimethyl-aminomethylcarbonyl-N-methyl-amino)-3-amino-anilino)-1-phenyl-methylene]-6-ethoxycarbonyl-2-indolinone
(138) 3-Z-[1-(4-(N-dimethyl-aminomethylcarbonyl-N-methyl-amino)-3-nitro-anilino)-1-phenyl-methylene]-6-ethoxycarbonyl-2-indolinone
(139) 3-Z-[1-(4-(N-dimethyl-aminomethylcarbonyl-N-methyl-amino)-3-acetylamino-anilino)-methylene]-6-ethoxycarbonyl-2-indolinone
(140) 3-Z-[1-(4-(N-dimethyl-aminomethylcarbonyl-N-methyl-amino)-3-methylsulphonylamino-anilino)-1-phenyl-methylene]-6-ethoxycarbonyl-2-indolinone
(141) 3-Z-[1-(4-(N-dimethyl-aminomethylcarbonyl-N-methyl-amino)-3-cyano-anilino)-1-phenyl-methylene]-6-ethoxycarbonyl-2-indolinone
(142) 3-Z-[1-(4-(N-dimethyl-aminomethylcarbonyl-N-methyl-amino)-3-hydroxy-anilino)-1-phenyl-methylene]-6-ethoxycarbonyl-2-indolinone
(143) 3-2-[1-(4-(N-dimethyl-aminomethylcarbonyl-N-methyl-amino)-3-methoxy-anilino)-1-phenyl-methylene]-6-ethoxycarbonyl-2-indolinone
(144) 3-Z-[1-(4-(N-dimethyl-aminomethylcarbonyl-N-methyl-amino)-3-ethoxycarbonylanilino)-1-phenyl-methylene]-6-ethoxycarbonyl-2-indolinone
(145) 3-2-[1-(4-(N-dimethyl-aminomethylcarbonyl-N-methyl-amino)-3-carboxy-anilino)-1-phenyl-methylene]-6-ethoxycarbonyl-2-indolinone
(146) 3-Z-[1-(4-(N-dimethyl-aminomethylcarbonyl-N-methyl-amino)-3-carbamoyl-anilino)-1-phenyl-methylene]-6-ethoxycarbonyl-2-indolinone
(147) 3-Z-[1-(4-(N-dimethyl-aminomethylcarbonyl-N-methyl-amino)-3-chloro-anilino)-1-phenyl-methylene]-6-ethoxycarbonyl-2-indolinone
(148) 3-Z-[1-(4-(N-dimethyl-aminomethyl carbonyl-N-methyl-amino)-3-fluoro-anilino)-1-phenyl-methylene]-6-ethoxycarbonyl-2-indolinone
(149) 3-Z-[1-(4-(N-dimethyl-aminomethylcarbonyl-N-methyl-amino)-3-bromo-anilino)-1-phenyl-methylene]-6-ethoxycarbonyl-2-indolinone
(150) 3-Z-[1-(4-(N-dimethyl-aminomethylcarbonyl-N-methyl-amino)-3-methyl-anilino)-1-phenyl-methylene]-6-ethoxycarbonyl-2-indolinone
(151) 3-Z-[1-(4-(N-dimethyl-aminomethylcarbonyl-N-methyl-amino)-3-trifluoromethyl-anilino)-1-phenyl-methylene]-6-ethoxycarbonyl-2-indolinone
(152) 3-Z-[1-(4-(N-dimethyl-aminomethylcarbonyl-N-methyl-amino)-3,5-dibromo-anilino)-1-phenyl-methylene]-6-ethoxycarbonyl-2-indolinone
(153) 3-Z-[1-(4-(N-dimethyl-aminomethylcarbonyl-N-methyl-amino)-3,5-dichloro-anilino)-1-phenyl-methylene]-6-ethoxycarbonyl-2-indolinone
(154) 3-Z-[1-(4-(dimethyl-aminomethyl)-3-amino-anilino)-1-phenyl-methylene]-6-ethoxycarbonyl-2-indolinone
(155) 3-Z-[1-(4-(dimethyl-aminomethyl)-3-nitro-anilino)-1-phenyl-methylene]-6-ethoxycarbonyl-2-indolinone
(156) 3-Z-[1-(4-(dimethyl-aminomethyl)-3-acetylamino-anilino)-1-phenyl-methylene]-6-ethoxy carbonyl-2-indolinone
(157) 3-Z-[1-(4-(dimethyl-aminomethyl)-3-(methylsulphonylamino)-anilino)-1-phenyl-methylene]-6-ethoxycarbonyl-2-indolinone
(158) 3-2-[1-(4-(dimethyl-aminomethyl)-3-cyano-anilino)-1-phenyl-methylene]-6-ethoxycarbonyl-2-indolinone
(161) 3-2-[1-(4-(dimethyl-aminomethyl)-3-(ethoxycarbonyl)-anilino)-1-phenyl-methylene]-6-ethoxycarbonyl-2-indolinone
(162) 3-Z-[1-(4-(dimethyl-aminomethyl)-3-carboxy-anilino)-1-phenyl-methylene]-6-ethoxycarbonyl-2-indolinone
(163) 3-2-[1-(4-(dimethyl-aminomethyl)-3-carbamoyl-anilino)-1-phenyl-methylene]-6-ethoxycarbonyl-2-indolinone
(164) 3-Z-[1-(4-(dimethyl-aminomethyl)-3-chloro-anilino)-1-phenyl-methylene]-6-ethoxycarbonyl-2-indolinone
(165) 3-Z-[1-(4-(dimethyl-aminomethyl)-3-fluoro-anilino)-1-phenyl-methylene]-6-ethoxycarbonyl-2-indolinone
(166) 3-Z-[1-(4-(dimethyl-aminomethyl)-3-bromo-anilino)-1-phenyl-methylene]-6-ethoxycarbonyl-2-indolinone
(167) 3-Z-[1-(4-(dimethyl-aminomethyl)-3-methyl-anilino)-1-phenyl-methylene]-6-ethoxycarbonyl-2-indolinone
(168) 3-Z-[1-(4-(dimethyl-aminomethyl)-3-trifluoromethyl-anilino)-1-phenyl-methylene]-6-ethoxycarbonyl-2-indolinone
(169) 3-Z-[1-(4-(dimethyl-aminomethyl)-3,5-dibromo-anilino)-1-phenyl-methylene]-6-ethoxycarbonyl-2-indolinone
(170) 3-Z-[1-(4-(dimethyl-aminomethyl)-3,5-dichloro-anilino)-1-phenyl-methylene]-6-ethoxycarbonyl-2-indolinone (171) 3-Z-[1-(4-(N-((4-methyl-piperazin-1-yl)-methylcarbonyl)-N-methyl-amino)-anilino)-1-phenyl-methylene]-6-ethoxycarbonyl-2-indolinone
(172) 3-Z-[1-(4-(N-(imidazo-1-yl-methylcarbonyl)-N-methyl-amino)-anilino)-1-phenyl-methylene]-6-ethoxycarbonyl-2-indolinone
(173) 3-Z-[1-(4-(N-(phthalimido-2-yl-methylcarbonyl)-N-methylindolinone
(174) 3-Z-[1-(4-(N-aminomethylcarbonyl-N-methyl-amino)-anilino)-1-phenyl-methylene]-6-ethoxycarbonyl-2-indolinone
(175) 3-Z-[1-(4-(N-acetylaminomethylcarbonyl-N-methyl-amino)-anilino)-1-phenyl-methylene]-6-ethoxycarbonyl-2-indolinone
(176) 3-Z-[1-(4-(N-methylsulphonylaminomethylcarbonyl-N-methyl-amino)-anilino)-1-phenyl-methylene]-6-ethoxycarbonyl-2-indolinone
(177) 3-Z-[1-(4-(N—((N-(2-methoxyethyl)-N-methyl-amino)-methylcarbonyl)-N-methyl-amino)-anilino)-1-phenyl-methylene]-6-ethoxycarbonyl-2-indolinone
(178) 3-Z-[1-(4-(N—((N-(2-dimethyl-aminoethyl)-N-methyl-amino)-methylcarbonyl)-N-methyl-amino)-anilino)-1-phenyl-methylene]-6-ethoxycarbonyl-2-indolinone
(179) 3-Z-[1-(4-(N-((di-(2-hydroxyethyl))-amino)-methyl-carbonyl)-N-methyl-amino)-anilino) 1-phen-methylene]-6-ethoxycarbonyl-2-indolinone
(180) 3-Z-[1-(4-(N-dimethyl-aminomethylcarbonyl-N-methyl-amino)-anilino)-methylene]-6-ethoxycarbonyl-2-indolinone
(181) 3-Z-[1-(4-(N-dimethyl-aminomethylcarbonyl-N-methyl-amino)-anilino)-ethylidene]-6-ethoxycarbonyl-2-indolinone
(182) 3-Z-[1-(4-(N-dimethyl-aminomethylcarbonyl-N-methyl-amino)-anilino)-propylidene]-6-ethoxycarbonyl-2-indolinone
(183) 3-Z-[1-(4-(N-dimethyl-aminomethylcarbonyl-N methyl-amino)-anilino)-butylidene]-6-ethoxycarbonyl-2-indolinone
(184) 3-Z-[1-(4-(dimethyl-aminomethyl)-anilino)-methylene]-6-ethoxycarbonyl-2-indolinone
(185) 3-Z-[1-(4-(dimethyl-aminomethyl)-anilino)-ethylidene]-6-ethoxycarbonyl-2-indolinone
(186) 3-Z-[1-(4-(dimethyl-aminomethyl)-anilino)-propylidene]-6-ethoxycarbonyl-2-indolinone
(187) 3-Z-[1-(4-(dimethyl-aminomethyl)-anilino)-butylidene]-6-ethoxycarbonyl-2-indolinone
(188) 3-2-[1-(4-(N-dimethyl-aminocarbonylmethyl-amino)-anilino)-1-phenyl-methylene]-6-ethoxy-carbonyl-2-indolinone
(189) 3-Z-[1-(4-(N-(3-dimethyl-amino-propyl)-N-acetyl-amin0)-anilino)-1-phenyl-methylene]-6-ethoxycarbonyl-2-indolinone
(190) 3-Z-[1-(4-((imidazolidin-2,4-dion-5-ylidene)-methyl)-anilino)-1-phenyl-methylene]-6-ethoxycarbonyl-2-indolinone
(191) 3-2-[1-(4-(N-((2-dimethyl-amino-ethyl)-carbonyl)-N-methyl-amino)-anilino)-1-phenyl-methylene]-6-ethoxy-carbonyl-2-indolinone
(192) 3-Z-[1-(4-(N-tert.butoxycarbonyl-amino-methyl)-anilino)-1-phenyl-methylene]-6-ethoxycarbonyl-2-indolinone
(193) 3-Z-[1-(4-(2-oxo-pyrrolidin-1-yl-methyl)-anilino)-phenyl-methylene]-6-ethoxycarbonyl-2-indolinone
(194) 3-Z-[1-(4-(N-aminocarbonylmethyl-N-methyl sulphonyl-amino)-anilino)-1-phenyl-methylene]-6-ethoxycarbonyl-2-indolinone
(195) 3-Z-[1-(4-(N-cyanomethyl-N-methyl sulphonyl-amino)-anilino)-1-phenyl-methylene]-6-ethoxycarbonyl-2-indolinone
(196) 3-Z-[1-(4-(2-(imidazol-4-yl)-ethyl)-anilino)-1-phenyl-methylene]-6-ethoxycarbonyl-2-indolin
(197) 3-Z-[1-(4-((2-(N-benzyl-N-methyl-amino)-ethyl)-N-methyl sulphonyl-amino)-anilino)-1-phenyl-methylene]-6-ethoxycarbonyl-2-indolinone
(198) 3-2-[1-(4-cyclohexylamino-anilino)-1-phenyl-methylene]-6-ethoxycarbonyl-2-indolinone
(199) 3-Z-[1-(4-(imidazol-1-yl-methyl)-anilino)-1-phenyl-methylene]-6-ethoxycarbonyl-2-indolinone
(200) 3-Z-[1-(4-(imidazol-1-yl-methyl)-anilino)-1-phenyl-methylene]-6-ethoxycarbonyl-2-indolinone
(200) 3-Z-[1-(4-(imidazol-1-yl-methyl)-anilino)-1-phenyl-methylene]-6-ethoxycarbonyl-2-indolinone
(201) 3-Z-[1-(N-methyl-piperidine-4-yl-amino)-1-phenyl-methylene]-6-ethoxycarbonyl-2-indolinone
(202) 3-Z-[1-(4-(imidazol-4-yl)-anilino)-1-phenyl-methylene]-6-ethoxycarbonyl-2-indolinone
(203) 3-Z-[1-(4-(4-hydroxy-piperidin-1-yl)-methyl)-anilino)-1-phenyl-methylene]-6-ethoxycarbonyl-2-indolinone
(204) 3-Z-[1-(4-(4-methoxy-piperidin-1-yl)-methyl)-anilino)-1-phenyl-methylene]-6-ethoxycarbonyl-2-indolinone
(205) 3-Z-[1-(4-benzyl-anilino)-1-phenyl-methylene]-6-ethoxycarbonyl-2-indolinone
(206) 3-Z-[1-(4-(N-(3-trifluoroacetylamino-propyl)-N-methylsulphonyl-amino)-anilino)-1-phenyl-methylene]-6-ethoxycarbonyl-2-indolinone
(207) 3-Z-[1-(4-(4-tert.butoxycarbonyl-piperazin-1-yl-methyl)-anilino)-1-phenyl-methylene]-6-ethoxycarbonyl-2-indolinone
(208) 3-Z-[1-(4-(1-methyl-imidazol-2-yl)-anilino)-1-phenylmethylene]-6-ethoxycarbonyl-2-indolinone (210) 3-Z-[1-(4-(N-(2-dimethyl-amino-ethyl)-N-methylsulphonyl-amino)-anilino)-1-phenyl-methylene]-6-ethoxycarbonyl-2-indolinone
(211) 3-Z-[1-(4-((3-(N-benzyl-N-methyl-amino)-propyl)-N-methyl sulphonyl-amino)-anilino)-1-phenyl-methylene]-6-ethoxycarbonyl-2-indolinone
(212) 3-2-[1-(4-(N-(2-dimethyl-amino-ethyl)-N-acetyl-amino)-anilino)-1-phenyl-methylene]-6-ethoxycarbonyl-2-indolinone
(213) 3-Z-[1-(4-(N-(2-dimethyl-amino-ethyl)-N-butyryl-amino)-anilino)-1-phenyl-methylene]-6-ethoxycarbonyl-2-indolinone
(214) 3-Z-[1-(4-(N-(2-dimethyl-amino-ethyl)-N-isobutyryl-amino)-anilino)-1-phenyl-methylene]-6-ethoxycarbonyl-2-indolinone
(215) 3-Z-[1-(4-(N-(2-dimethyl-amino-ethyl)-N-benzoyl-amino)-anilino)-1-phenyl-methylene]-6-ethoxycarbonyl-2-indolinone
(216) 3-Z-[1-(4-(N-(2-dimethyl-amino-ethyl)-N-acetyl-amino)-3-amino-anilino)-1-phenyl-methylene]-6-ethoxy-carbonyl-2-indolinone
(217) 3-Z-[1-(4-(4-hydroxymethyl-piperidin-1-yl-methyl)-anilino)-1-phenyl-methylene]-6-ethoxycarbonyl-2-indolinone
(219) 3-Z-[1-(4-(N-(2-dimethyl-amino-ethyl)-N-propylsulphonylamino)-anilino)-1-phenyl-methylene]-6-ethoxy-carbonyl-2-indolinone
(220) 3-Z-[1-(4-(N-(2-dimethyl-amino-ethyl)-N-butylsulphonylamino)-anilino)-1-phenyl-methylene]-6-ethoxycarbonyl-2-indolinone (221) 3-Z-[1-(4-(N-(2-dimethyl-amino-ethyl)-N-phenylsulphonylamino)-anilino)-1-phenyl-methylene]-6-ethoxycarbonyl-2-indolinone
(222) 3-Z-[1-(4-(N-(2-dimethyl-amino-ethyl)-N-benzylsulphonylamino)-anilino)-1-phenyl-methylene]-6-ethoxycarbonyl-2-indolinone
(223) 3-Z-[1-(4-((imidazolidin-2,4-dion-5-yl)-methyl)-anilino)-1-phenyl-methylene]-6-ethoxycarbonyl-2-indolinone
(224) 3-Z-[1-(4-((3-hydroxy-pyrrolidin-1-yl)-methyl)-anilino)-1-phenyl-methylene]-6-ethoxycarbonyl-2-indolinone
(225) 3-Z-[1-(4-(cyclohexylyl-methyl)-anilino)-1-phenylmethylene]-6-ethoxycarbonyl-2-indolinone
(226) 3-Z-[1-(4-(cyclohexyl-carbonyl)-anilino)-1-phenylmethylene]-6-ethoxycarbonyl-2-indolinone
(227) 3-Z-[1-(4-diethylaminomethyl-anilino)-1-phenylmethylene]-6-ethoxycarbonyl-2-indolinone
(228) 3-Z-[1-(4-(N-(n-hexyl)-N-methyl-aminomethyl)-anilino)-1-phenyl-methylene]-6-ethoxy-carbonyl-2-indolinone
(229) 3-Z-[1-(4-(N-(2-dimethyl-amino-ethyl)-N-(furan-2-carbonyl)-amino)-anilino)-1-phenyl-methylene]-6-ethoxycarbonyl-2-indolinone
(230) 3-Z-[1-(4-(N-(2-dimethyl-amino-ethyl)-N-(2-methoxy-benzoyl)-amino)-anilino)-1-phenyl-methylene]-6-ethoxycarbonyl-2-indolinone
(231) 3-Z-[1-(4-(N-(2-dimethyl-amino-ethyl)-N-(pyridine-3-carbonyl)-amino)-anilino)-1-phenyl-methylene]-6-ethoxycarbonyl-2-indolinone
(232) 3-Z-[1-(4-(N-(2-dimethyl-amino-ethyl)-N-(phenylacetyl)-amino)-anilino)-1-phenyl-methylene]-6-ethoxycarbonyl-2-indolinone
(233) 3-Z-[1-(4-(imidazol-2-yl)-anilino)-1-phenyl-methylene]-6-ethoxycarbonyl-2-indolinone
(234) 3-Z-[1-(4-(1-ethyl-imidazol-2-yl)-anilino)-1-phenyl-methylene]-6-ethoxycarbonyl-2-indolinone
(235) 3-Z-[1-(4-(1-benzyl-imidazol-2-yl)-anilino)-1-phenyl-methylene]-6-ethoxycarbonyl-2-indolinone
(236) 3-Z-[1-(4-(N-(2-dimethyl-amino-ethyl)-N-isopropyl-sulphonyl-amino)-anilino)-1-phenyl-methylene]-6-ethoxycarbonyl-2-indolinone
(237) 3-Z-[1-(4-(N44-benzyl-piperazin-1-yl)-methylcarbonyl)-N-methyl-amino)-anilino)-1-phenyl-methylene]-6-ethoxycarbonyl-2-indolinone
(238) 3-Z-[1-(4-(N-(pyrrolidin-1-yl-methylcarbonyl)-N-methyl-amino)-anilino)-1-phenyl-methylene]-6-ethoxycarbonyl-2-indolinone
(239) 3-2-[1-(4-(N-(2-dimethyl-amino-ethyl)-N-acetylamino)-3-bromo-anilino)-1-phenyl-methylene]-6-ethoxycarbonyl-2-indolinone
(240) 3-Z-[1-(4-(5-methyl-imidazol-4-yl)-anilino)-1-phenyl-methylene]-6-ethoxycarbonyl-2-indolinone
(241) 3-Z-[1-(4-(N-((2-dimethyl-amino-ethyl)-carbonyl)-N-isopropyl-amino)-anilino)-1-phenyl-methylene]-6-ethoxycarbonyl-2-indolinone
(242) 3-Z-[1-(4-(N-((2-dimethyl-amino-ethyl)-carbonyl)-N-benzyl-amino)-anilino)-1-phenyl-methylene]-6-ethoxycarbonyl-2-indolinone
(243) 3-Z-[1-(4-(N-butyl-N-tert-butoxycarbonyl-aminomethyl)-anilino)-1-phenyl-methylene]-6-ethoxycarbonyl-2-indolinone
(244) 3-Z-[1-(4-(N—(N-aminocarbonylmethyl-N-methyl-amino)-methylcarbonyl)-N-methyl-amino)-anilino)-1-phenyl-methylene]-6-ethoxycarbonyl-2-indolinone
(245) 3-Z-[1-(4N—((N-benzyl-N-methyl-amino)-methylcarbonyl)-N-methyl-amino)-anilino)-1-phenyl-methylene]-6-ethoxycarbonyl-2-indolinone
(246) 3-Z-[1-(4-(N-(di-(2-methoxyethly)-amino)-methylcarbonyl)-N-methyl-amino)-anilino)-1-phenyl-methylene]-6-ethoxycarbonyl-2-indolinone
(247) 3-2-[1-(4-(N-((2-(4-tert.butoxycarbonyl-piperazin-1-yl)-ethyl)-carbonyl)-N-methyl-amino)-anilino)-1-phenyl-methylene]-6-ethoxycarbonyl-2-indolinone
(248) 3-2-[1-(4-(N-((2-(piperidin-1-yl)-ethyl)-carbonyl)-N-methyl-amino)-anilino)-1-phenyl-methylene]-6-ethoxycarbonyl-2-indolinone
(249) 3-Z-[1-(4-(N-((2-(N-benzyl-N-methyl-amino)-ethyl)-carbonyl)-N-methyl-amino)-anilino)-1-phenyl-methylene]-6-ethoxycarbonyl-2-indolinone
(250) 3-Z-[1-(4-(N-dimethylaminomethylcarbonyl-N-isopropyl-amino)-anilino)-1-phenyl-methylene]-6-ethoxycarbonyl-2-indolinone
(251) 3-Z-[1-(4-(N-(piperidin-1-yl-methylcarbonyl)-N-isopropyl-amino)-anilino)-1-phenyl-methylene]-6-ethoxycarbonyl-2-indolinone
(252) 3-Z-[1-(4-(N-((4-tert-butoxycarbonyl-piperazin-1-yl)-methylcarbonyl)-N-isopropyl-amino)-anilino)-1-phenyl-methylene]-6-ethoxycarbonyl-2-indolinone
(253) 3-Z-[1-(4-(N—((N-benzyl-N-methyl-amino)-methylcarbonyl)-N-benzyl-amino)-anilino)-1-phenylmethylene]-6-ethoxycarbonyl-2-indolinone
(254) 3-Z-[1-(4-(N-dimethyl-aminomethylcarbonyl-N-benzylamino)-anilino)-1-phenyl-methylene]-6-ethoxycarbonyl-2-indolinone
(255) 3-2-[1-(4-(N-(piperidin-1-yl-methylcarbonye-N-benzylamino)-anilino)-1-phenyl-methylene]-6-ethoxycarbonyl-2-indolinone
(256) 3-Z-[1-(4-(1,2,4-triazol-2-yl-methyl)-anilino)-1-phenyl-methylene]-6-ethoxycarbonyl-2-indolinone
(257) 3-Z-[1-(4-(1,2,3-triazol-2-yl-methyl)-anilino)-1-phenyl-methylene]-6-ethoxycarbonyl-2-indolinone
(258) 3-Z-[1-(4-(1,2,3-triazol-1-yl-methyl)-anilino)-1-phenyl-methylene]-6-ethoxycarbonyl-2-indolinone
(259) 3-Z-[1-(4-((N-aminocarbonylmethyl-N-methyl-amino)-methyl)anilino)-1-phenyl-methylene]-6-ethoxycarbonyl-2-indolinone
(260) 3-Z-[1-(4-((di-(2-methoxy-ethyl)-amino)-methyl)-anilino)-1-phenyl-methylene]-6-ethoxycarbonyl-2-indolinone
(261) 3-Z-[1-(4-((di-(2-hydroxy-ethyl)-amino)-methyl)-anilino)-1-phenyl-methylene]-6-ethoxycarbonyl-2-indolinone
(262) 3-Z-[1-(4-((N-ethoxycarbonylmethyl-N-methyl-amino)-methyl)-anilino)-1-phenyl-1-methylene]-6-ethoxycarbonyl-2-indolinone
(263) 3-Z-[1-(4-(azetidin-1-yl-methyl)-anilino)-1-phenyl-methylene]-6-ethoxycarbonyl-2-indolinone
(264) 3-Z-[1-(4-(N-propyl-N-tert.butoxycarbonyl-aminomethyl)-anilino)-1-phenyl-methylene]-6-ethoxycarbonyl-2-indolinone
(265) 3-2-[1-(4-((N-(2-(2-methoxy-ethoxy)-ethyl)-N-methyl-amino)-methyl)-anilino)-1-phenyl-methylene]-6-ethoxycarbonyl-2-indolinone
(266) 3-Z-[1-(4-((N-(tert.butoxycarbonyl-3-amino-propyl)-N-methyl-amino)-methyl)-anilino)-1-phenyl-methylene]-6-ethoxycarbonyl-2-indolinone
(267) 3-Z-[1-(4-((N-(methylcarbamoyl-methyl)-N-methyl-amino)-methyl)-anilino)-1-phenyl-methylene]-6-ethoxycarbonyl-2-indolinone (268) 3-Z-[1-(4-((N-(dimethyl carbamoyl-methyl)-N-methyl-amino)-methyl)-anilino)-1-phenyl-methylene]-6-ethoxycarbonyl-2-indolinone
(269) 3-Z-[1-(4-((N-propyl-N-methyl-amino)-methyl)-anilino)-1-phenyl-methylene]-6-ethoxycarbonyl-2-indolinon
(270) 3-Z-[1-(4-((N-(2-dimethyl-amino-ethyl)-N-methyl-amino)-methyl)-anilino)-1-phenyl-methylene]-6-ethoxycarbonyl-2-indolinone
(271) 3-Z-[1-(4-((N-(3-dimethyl-amino-propyl)-N-methyl-amino)-methyl)-anilino)-1-phenyl-methylene]-6-ethoxycarbonyl-2-indolinone
(272) 3-Z-[1-(4-((N-(2-methoxy-ethyl)-N-methyl-amino)-methyl)-anilino)-1-phenyl-methylene]-6-ethoxycarbonyl-2-indolinone
(273) 3-Z-[1-(4-((N-(2-hydroxy-ethyl)-N-methyl-amino)-methyl)-anilino)-1-phenyl-methylene]-6-ethoxycarbonyl-2-indolinone
(274) 3-Z-[1-(4-((N-(dioxolan-2-yl-methyl)-N-methyl-amino)-methyl)-anilino)-1-phenyl-methylene]-6-ethoxycarbonyl-2-indolinone
(275) 3-Z-[1-(4-(3-oxo-piperazin-1-yl-methyl)-anilino)-1-phenyl-methylene]-6-ethoxycarbonyl-2-indolinone
(276) 3-Z-[1-(4-(N-(piperazin-1-yl-methylcarbonyl)-N-isopropyl-amino)-anilino)-1-phenyl-methylene]-6-ethoxycarbonyl-2-indolinone
(277) 3-2-[1-(4-(N-((2-(piperazin-1-yl)-ethyl)-carbonyl)-N-methyl-amino)-anilino)-1-phenyl-methylene]-6-ethoxycarbonyl-2-indolinone
(278) 3-2-[1-(4-((N-(3-amino-propyl)-N-methyl-amino)-methyl)-anilino)-1-phenyl-methylene]-6-ethoxycarbonyl-2-indolinone
(279) 3-Z-[1-(4-(N-3-methyl-amino-propyl)-N-methylsulphonylamino)-anilino)-1-phenyl-methylene]-6-ethoxycarbonyl-2-indolinone
(280) 3-Z-[1-(4-Ureidomethyl-anilino)-1-phenyl-methylene]-6-ethoxycarbonyl-2-indolino
(281) 3-Z-[1-(4-guanidinomethyl-anilino)-1-phenyl-methylene]-6-ethoxycarbonyl-2-indolinone
(282) 3-Z-[1-(4-(N-methy1~su1~hon~1-aminomethyl)-anilino)-1-phenyl-methylene]-6-ethoxycarbonyl-2
(283) 3-Z-[1-(4-(4-benzoyl-piperazin-1-yl-methyl)-anilino)-1-phenyl-methylene]-6-ethoxycarbonyl-indolinone
(284) 3-Z-[1-(4-((N-(3-acetylamino-propyl)-N-methyl-amino)-methyl)-anilino)-1-phenyl-methylene]-6-ethoxycarbonyl-2-indolinone
(285) 3-Z-[1-(4-((N-(3-methylsulphonylamino-propyl)-N-methyl-amino)-methyl)-anilino)-1-phenyl-methylene]-6-ethoxycarbonyl-2-indolinone
(286) 3-Z-[1-(4-((N-carboxymethyl-N-methyl-amino)-methyl)-anilino)-1-phenyl-methylene]-6-ethoxycarbonyl2-indolinone
(287) 3-Z-(1-anilino-1-phenyl-methylene)-6-methoxycarbonyl-2-indolinone
(288) 3-Z-[1-(4-nitro-anilino)-1-phenyl-methylene]-6-methoxy carbonyl-2-indolinone
(289) 3-Z-[1-(4-fluoro-anilino)-1-phenyl-methylene]-6-methoxycarbonyl-2-indolinone
(290) 3-Z-[1-(4-chloro-anilino)-1-phenyl-methylene]-6-methoxycarbonyl-2-indolinone
(291) 3-Z-[1-(4-bromo-anilino)-1-phenyl-methylene]-6-methoxycarbonyl-2-indolinone
(292) 3-Z-[1-(4-iodo-anilino)-1-phenyl-methylene]-6-methoxycarbonyl-2-indolinone
(293) 3-Z-[1-(4-cyano-anilino)-1-phenyl-methylene]-6-methoxycarbonyl-2-indolinone
(294) 3-Z-[1-(4-carboxy-anilino)-1-phenyl-methylene]-6-methoxycarbonyl-2-indolinone
(295) 3-Z-[1-(4-methoxy-anilino)-1-phenyl-methylene]-6-methoxycarbonyl-2-indolinone
(296) 3-Z-[1-(4-ethoxy-anilino)-1-phenyl-methylene]-6-methoxycarbonyl-2-indolinone
(297) 3-Z-[1-(4-trifluoromethyl-anilino)-1-phenyl-methylene]-6-methoxycarbonyl-2-indolinone
(298) 3-Z-[1-(4-methylmercapto-anilino)-1-phenyl-methylene]-6-methoxycarbonyl-2-indolinone
(299) 3-2-C1-(4-(isopropylaminomethyl)-anilino)-1-phenylmethylene]-6-methoxycarbonyl-2-indolinone
(300) 3-Z-[1-(4-(anilinomethyl)-anilino)-1-phenyl-methylene]-6-methoxycarbonyl-2-indolinone
(301) 3-Z-[1-(4-(isobutylaminomethyl)-anilino)-1-phenyl-methylene]-6-methoxycarbonyl-2-indolinone
(302) 3-2-[1-(4-(cyclohexylaminomethyl)-anilino)-1phenyl-methylene]-6-methoxycarbonyl-2-indolinone
(303) 3-Z-[1-(4-(benzylaminomethyl)-anilino)-1-phenylmethylene]-6-methoxycarbonyl-2-indolinone
(304) 3-Z-[1-(4-((N-methyl-N-propyl-amino)-methyl)-anilino)-1-phenyl-methylene]-6-methoxy carbonyl-2-indolinone
(305) 3-Z-[1-(4-((N-isopropyl-N-methyl-amino)-methyl)-anilino)-1-phenyl-methylene-6-methoxy carbonyl-2-indolinone
(306) 3-Z-[1-(4-((N-ethyl-N-propyl-amino)-methyl)-anilino)-1-phenyl-methylene]-6-methoxy carbonyl-2-indolinone
(307) 3-Z-[1-(4-((N-ethyl-N-isopropyl-amino)-methyl)-anilino)-1-phenyl-methylene]-6-methoxy carbonyl-2-indolinone
(308) 3-Z-[1-(4-(dipropylaminomethyl)-anilino)-1-phenyl-methylene]-6-methoxycarbonyl-2-indolinone
(309) 3-Z-[1-(4-(diisopropylaminomethyl)-anilino)-1-phenyl-methylene]-6-methoxycarbonyl-2-indolinone
(310) 3-Z-[1-(4-((N-benzyl-N-ethyl-amino)-methyl)-anilino)-1-phenyl-methylene]-6-methoxycarbonyl-2-indolinone
(311) 3-Z-[1-(4-(dibenzylaminomethyl)-anilino)-1-phenyl-methylene]-6-methoxycarbonyl-2-indolinone
(312) 3-Z-[1-(4-(3,6-dihydro-2H-pyridin-1-yl-methyl)-anilino)-1-phenyl-methylene]-6-methoxy carbonyl-2-indolinone
(313) 3-Z-[1-(4-(3,5-dimethyl-piperidin-1-yl-methyl)-anilino)-1-phenyl-methylene]-6-methoxy carbonyl-2-indolinone
(314) 3-Z-[1-(4-(azepan-1-yl-methyl)-anilino)-1-phenyl-methylene]-6-methoxycarbonyl-2-indolinone
(315) 3-Z-[1-(4-(2-amino-ethyl)-anilino)-1-phenyl-methylene]-6-methoxycarbonyl-2-indolinone
(316) 3-Z-[1-(4-(2-methylamino-ethyl)-anilino)-1-phenyl-methylene]-6-methoxycarbonyl-2-indolinone
(317) 3-Z-[1-(4-(2-ethylamino-ethyl)-anilino)-1-phenyl-methylene]-6-methoxycarbonyl-2-indolinone
(318) 3-Z-[1-(4-(2-dimethylamino-ethyl)-anilino)-1-phenyl-methylene]-6-methoxycarbonyl-2-indolinone
(319) 3-Z-[1-(4-(2-diethylamino-ethyl)-anilino)-1-phenyl-methylene]-6-methoxycarbonyl-2-indolinone
(320) 3-Z-[1-(4-(2-piperidin-1-yl-ethyl)-anilino)-1-phenyl-methylene]-6-methoxycarbonyl-2-indolinone
(321) 3-Z-[1-(4-(2-acetylamino-ethyl)-anilino)-1-phenyl-methylene]-6-methoxycarbonyl-2-indolinone
(322) 3-Z-[1-(4-(3-amino-propyl)-anilino)-1-phenyl-methylene]-6-methoxycarbonyl-2-indolinone
(323) 3-Z-[1-(4-(2-dimethylamino-propyl)-anilino)-1-phenyl-methylene]-6-methoxycarbonyl-2-indolinone (324) 3-Z-[1-(4-(N-aminomethylcarbonyl-N-methyl-amino)-anilino)-1-phenyl-methylene]-6-methoxycarb0nyl-2-indolinone
(325) 3-Z-[1-(4-(N-ethylaminomethylcarbonyl-N-methyl-amino)-anilino)-1-phenyl-methylene]-6-methoxycarbonyl-2-indolinone
(326) 3-Z-[1-(4-(N-diethylaminomethylcarbonyl-N-methyl-amino)-anilino)-1-phenyl-methylene]-6-methoxycarbonyl-2-indolinone
(327) 3-Z-[1-(4-(N-dipropylaminomethylcarbonyl-N-methyl-amino)-anilino)-1-phenyl-methylene]-6-methoxycarbonyl-2-indolinone
(328) 3-Z-[1-(4-(N—((N-ethyl-N-methyl-amino)-methylcarbonyl)-N-methyl-amino)-anilino)-1-phenyl-methylene]-6-methoxycarbonyl-2-indolinone
(329) 3-Z-[1-(4-(N—((N-ethyl-N-propyl-amino)-methylcarbonyl)-N-methyl-amino)-anilino)-1-phenyl-methylene]-6-methoxycarbonyl-2-indolinone
(330) 3-Z-[1-(4-(N—((N-methyl-N-propyl-amino)-methylcarbonyl)-N-methyl-amino)-anilino)-1-phenyl-methylene]-6-methoxycarbonyl-2-indolinone
(331) 3-Z-[1-(4-(N-dimethyl-aminomethylcarbonyl-N-ethyl-amino)-anilino)-1-phenyl-methylene]-6-methoxycarbonyl-2-indolinone
(332) 3-Z-[1-(4-(N-dimethyl-aminomethyl carbonyl-N-propylamino)-anilino)-1-phenyl-methylene]-6-methoxycarbonyl-2-indolinone
(333) 3-Z-[1-(4-(N-dimethyl-aminomethylcarbonyl-N-butyl-amino)-anilino)-1-phenyl-methylene]-6-methoxycarbonyl-2-indolinone
(334) 3-Z-[1-(4.-(N-(2-amino-ethyl carbonyl)-N-methyl-amino)-anilino)-1-phenyl-methylene]-6-methoxycarbonyl-2-indolinone
(335) 3-Z-[1-(4-(N-(2-diethylamino-ethylcarbonyl)-N-methyl-amino)-anilino)-1-phenyl-methylene]-6-methoxycarbonyl-2-indolinone
(336) 3-Z-[1-(4-(N-acetyl-N-(2-aminoethyl)-amino)-anilino)-1-phenyl-methylene]-6-methoxycarbonyl-2-indolinone
(337) 3-Z-[1-(4-(N-acetyl-N-(2-methyl-amino-ethyl)-amino)-anilino)-1-phenyl-methylene]-6-methoxycarbonyl-2-indolinone
(338) 3-Z-[1-(4-(N-acetyl-N-(3-methyl-amino-propyl)-amino)-anilino)-1-phenyl-methylene]-6-methoxycarbonyl-2-indolinone
(339) 3-Z-[1-(4-(N-acetyl-N-(2-piperidin-1-yl-ethyl)-amino)-anilino)-1-phenyl-methylene]-6-methoxycarbonyl-2-indolinone
(340) 3-Z-[1-(4-(N-acetyl-N-(aminocarbonylmethyl)-amino)-anilino)-1-phenyl-methylene]-6-methoxycarbonyl-2-indolinone
(341) 3-Z-[1-(4-(N-acetyl-N-(piperidin-1-yl-carbonylmethyl)-amino)-anilino)-1-phenyl-methylene]-6-methoxycarbonyl-2-indolinone
(342) 3-Z-[1-(4-(N-methyl-N-(aminocarbonyl)-amino)-anilino)-1-phenyl-methylene]-6-methoxycarbonyl-2-indolinone
(343) 3-Z-[1-(4-(N-methyl-N-(methyl-aminocarbonyl)-amino)-anilino)-1-phenyl-methylene]-6-methoxycarbonyl-2-indolinone
(344) 3-Z-[1-(4-(N-methyl-N-(dimethyl-aminocarbonyl)-amino)-anilino)-1-phenyl-methylene]-6-methoxycarbonyl-2-indolinone
(345) 3-Z-[1-(4-(N-methyl-N-(piperidin-1-yl-carbonyl)-amino)-anilino)-1-phenyl-methylene]-6-methoxycarbonyl-2-indolinone
(346) 3-Z-[1-(4-(N-(2-ethylamino-ethyl)-N-methylsulphonylamino)-anilino)-1-phenyl-methylene]-6-methoxycarbonyl-2-indolinone
(347) 3-Z-[1-(4-(N-(2-diethylamino-ethyl)-N-methylsulphonyl-amino)-anilino)-1-phenyl-methylene]6-methoxycarbonyl-2-indolinone
(348) 3-Z-[1-(4-(N-(2-pyrrolidin-1-yl-ethyl)-N-methyl sulphonyl-amino)-anilino)-1-phenyl-methylene]-6-methoxycarbonyl-2-indolinone
(349) 3-Z-[1-(4-(N-(2-piperidin-1-yl-ethyl)-N-methyl sulphonylamino)-anilino)-1-phenyl-methylene]-6-methoxycarbonyl-2-indolinone
(350) 3-Z-[1-(4-(N-(2-piperazin-1-yl-ethyl)-N-methyl sulphonylamino)-anilino)-1-phenyl-methylene]-6-methoxycarbonyl-2-indolinone
(351) 3-Z-[1-(4-(N-(2-(4-morpholin-1-yl)-ethyl)-N-methyl sulphonyl-amino)-anilino)-1-phenyl-methylene]-6-methoxycarbonyl-2-indolinone
(352) 3-Z-[1-(4-(N-(ethylaminocarbonylmethyl)-N-methyl sulphonyl-amino)-anilino)-1-phenyl-methylene]-6-methoxycarbonyl-2-indolinone
(353) 3-Z-[1-(4-(N-(diethylaminocarbonylmethyl)-N-methyl sulphonyl-amino)-anilino)-1-phenyl-methylene]-6-methoxycarbonyl-2-indolinone
(354) 3-Z-[1-(4-(N-(pyrrolidin-1-yl-carbonylmethyl)-N-methyl sulphonyl-amino)-anilino)-1-phenyl-methylene]-6-methoxycarbonyl-2-indolinone
(355) 3-Z-[1-(4-(N-(piperidin-1-yl-carbonylmethyl)-N-methylsulphonyl-amino)-anilino)-1-phenyl-methylene]-6-methoxycarbonyl-2-indolinone
(356) 3-Z-[1-(4-(N-(piperazin-1-yl-carbonylmethyl)-N-methyl sulphonyl-amino)-anilino)-1-phenyl-methylene]-6-methoxycarbonyl-2-indolinone
(357) 3-2-11-(4-(N-((morpholin-4-yl)-carbonylmethyl)-N-methylsulphonyl-amino)-anilino)-1-phenyl-methylene-]6-methoxycarbonyl-2-indolinone
(358) 3-Z-[1-(4-(2-dimethylamino-ethoxy)-anilino)-1-phenyl-methylene]-6-methoxycarbonyl-2-indolinone
(359) 3-Z-[1-(4-(3-dimethylamino-propoxy)-anilino)-1-phenyl-methylene]-6-methoxycarbonyl-2-indolinone
(360) 3-Z-[1-(4-(amino carbonylmethyl)-anilino)-1-phenyl-methylene]-6-methoxycarbonyl-2-indolinone
(361) 3-Z-[1-(4-(2-aminocarbonyl-ethyl)-anilin]-phenyl-methylene]-6-methoxycarbonyl-2-indolinone
(362) 3-Z-[1-(4-(pyridin-2y-1)-anilino)-1-phenyl methylene]-6-methoxycarbonyl-2-indolinone
(363) 3-Z-[1-(4-(pyridine-3-yl)-anilino)-1-phenyl-methylene]-6-methoxycarbonyl-2-indolinone
(364) 3-Z-[1-(4((N-~heneth~1-N-meth~1-anilino)-1-phenyl-methylene]-6-methoxycarbonyl-2-indolinone
(365) 3-Z-[1-(4-(N-acetyl-N-methyl-amino)-anilino)-1-phenyl-methylene]-6-methoxycarbonyl-2-indolinone
(366) 3-Z-[1-(4-(N-ethylcarbonyl-N-(dimethyl-aminocarbonylmethyl)-amino)-anilino)-1-phenyl-methylene]-6-methoxycarbonyl-2-indolinone
(367) 3-Z-[1-(4-(N-methyl-N-methyl sulphonyl-amio)-anilino)-1-phenyl-methylene]-6-methoxycarbonyl-2-indolinone
(368) 3-Z-[1-(4-carboxymethyl-anilino)-1-phenyl-methylene]-6-methoxycarbonyl-2-indolinone
(369) 3-Z-[1-(4-carbamoylmethyl-anilino)-1-phenyl-methylene]-6-methoxycarbonyl-2-indolinone
(370) 3-Z-[1-(4-dimethylcarbamoylmethyl-anilino)-phenyl-methylene]-6-methoxycarbonyl-2-indolinone
(371) 3-Z-[1-(4-tetrazol-5-yl-anilino)-1-phenyl-methylene]-6-methoxycarbonyl-2-indolinone (372) 3-Z-[1-(4-(piperidin-1-yl-methyl)-anilino)-methylene]-6-methoxycarbonyl-2-indolinone
(373) 3-Z-[1-(4-(piperidin-1-yl-methyl)-anilino)-ethylidene]-6-methoxycarbonyl-2-indolinone
(374) 3-Z-[1-(4-(piperidin-1-yl-methyl)-anilino)-propylidene]-6-methoxycarbonyl-2-indolinon
(375) 3-Z-[1-(4-(piperidin-1-yl-methyl)-anilino)-butylidene]-6-methoxycarbonyl-2-indolinone
(376) 3-Z-[1-(4-(N-(3-dimethyl-amino-propyl)-N-acetyl-amino)-anilino)-methylene]-6-methoxycarbonyl-2-indolinone
(377) 3-Z-[1-(4-(N-(3-dimethyl-amino-propyl)-N-acetyl-amino)-anilino)-ethylidene]-6-methoxy carbonyl-2-indolinone
(378) 3-Z-[1-(4-(N-(3-dimethyl-amino-propyl)-N-acetyl-amino)-anilino)-propylidene]-6-methoxy carbonyl-2-indolinone
(379) 3-Z-[1-(4-(N-(3-dimethyl-amino-propyl)-N-acetyl-amino)-anilino)-butylidene]-6-methoxy carbonyl-2-indolinone
(380) 3-Z-[1-(4-(N-(2-dimethyl-amino-ethyl)-N-methylsulphonylamino)-anilino)-methylene]-6-methoxycarbonyl-2-indolinone
(381) 3-Z-[1-(4-(N-(2-dimethyl-amino-ethyl)-N-methylsulphonylamino)-anilino)-ethylidene]-6-methoxycarbonyl-2-indolinone
(382) 3-Z-[1-(4-(N-(2-dimethyl-amino-ethyl)-N-methylsulphonylamino)-anilino)-propylidene]-6-methoxycarbonyl-2-indolinone
(383) 3-Z-[1-(4-(N-(2-dimethyl-amino-ethyl)-N-methylsulphonylamino)-anilino)-butylidene]-6-methoxycarbonyl-2-indolinone
(384) 3-Z-[1-(4-tetrazol-5-yl-anilino)-methylene]-6-methoxycarbonyl-2-indolinone
(385) 3-Z-[1-(4-tetrazol-5-yl-anilino)-ethylidene]-6-methoxycarbonyl-2-indolinone
(386) 3-Z-[1-(4-tetrazol-5-yl-anilino)-propylidene]-methoxycarbonyl-2-indolinone
(387) 3-Z-[1-(4-tetrazol-5-yl-anilino)-butylidene]-6-methoxycarbonyl-2-indolinone
(388) 3-Z-[1-(4-carboxy-anilino)-methylene]-6-methoxycarbonyl-2-indolinone
(389) 3-Z-[1-(4-carboxy-anilino)-ethylidene]-6-methoxycarbonyl-2-indolinone
(390) 3-Z-[1-(4-carboxy-anilino)-propylidene]-6-methoxycarbonyl-2-indolinone
(391) 3-Z-[1-(4-carboxy-anilino)-butylidenel-6-methoxycarbonyl-2-indolinone
(392) 3-Z-[1-(4-(N-benzyl-N-methyl-aminomethyl)-anilino)-1-methyl-methylene]-6-methoxycarbonyl-2-indolinone
(393) 3-2-[1-(4-(2,3,4,5-tetrahydrobenzo(d)azepin-3-yl-methyl)-anilino)-1-methyl-methylene]-6-methoxycarbonyl-2-indolinone
(394) 3-2-[1-(4-((benzo(1,3)dioxol-5-yl-methyl)-methyl-aminomethyl)-anilino)-1-methyl-methylene]-6-methoxycarbonyl-2-indolinone
(395) 3-Z-[1-(4-(N-phenethyl-N-methyl-aminomethyl)-anilino)-1-methyl-methylene]-6-methoxycarbonyl-2-indolinone
(396) 3-Z-[1-(4-(N-(3,4-dimethoxy-benzyl)-N-methyl-aminomethyl)-anilino)-1-methyl-methylene]-6-methoxycarbonyl-2-indolinone
(397) 3-Z-[1-(4-(N-(4-Chloro-benzyl)-N-methyl-amino-methyl)-anilino)-1-methyl-methylene]-6-methoxycarbonyl-2-indolinone
(398) 3-Z-[1-(4-(N-(4-methylbenzyl)-N-methyl-aminomethyl)-anilino)-1-methyl-methylene]-6-methoxycarbonyl-2-indolinone
(399) 3-Z-[1-(4-(N-(4-fluoro-benzyl)-N-methyl-aminomethyl)-anilino)-1-methyl-methylene]-6-methoxycarbonyl-2-indolinone
(400) 3-Z-1 1-(4-(N-(4-bromo-benzyl)-N-methyl-aminomethyl)anilino)-1-methyl-methylene]-6-methoxycarbonyl-2-indolinone
(401) 3-Z-[1-(4-(N-(3-dimethyl-amino-propionyl)-N-dimethyl-aminocarbonylmethyl-amino)-anilino)-1-phenylmethylene]-6-methoxycarbonyl-2-indolinone
(402) 3-Z-[1-(4-(N-(4-dimethyl-amino-butyryl)-N-dimethyl-aminocarbonylmethyl-amino)-anilino)-1-phenyl-methylene]-6-methoxycarbonyl-2-indolinone
(403) 3-Z-[1-(4-(N-dimethyl-aminocarbonylmethyl-N-(2-dimethyl-amino-ethylsulphonyl)-amino)-anilino)-1-phenyl-methylene]-6-methoxycarbonyl-2-indolinone
(404) 3-Z-[I-(4-(N-dimethylaminocarbonylmethyl-N-(3-dimethylamino-propylsulphonyl)-amino)-anilino)-1-phenyl-methylene]-6-methoxycarbonyl-2-indolinon
(405) 3-Z-[I-(4-((2-hydroxy-ethyl)-amino-methyl)-anilino)-1-phenyl-methylene]-6-methoxycarbonyl-2-indolinone
(406) 3-Z—[I-(4-((2-methoxy-ethyl)-amino-methyl)-anilino)-1-phenyl-methylene]-6-methoxycarbonyl-2-indolinone
(407) 3-Z-[1-(4-((2-dimethyl-amino-ethyl)-amino-methyl)-anilino)-1-phenyl-methylene]-6-methoxycarbonyl-2-indolinone
(408) 3-Z-[1-(4-((3-dimethyl-amino-propyl)-amino-methyl)-anilino)-1-phenyl-methylene]-6-methoxycarbonyl-2-indolinone
(409) 3-Z-[1-(4-((N-tert.butoxycarbonyl-2-amino-ethyl)-amino-methyl)-anilino)-1-phenyl-methylene]-6-methoxycarbonyl-2-indolinone
(410) 3-Z-[1-(4-((N-tert-butoxycarbonyl-3-amino-propyl)-amino-methyl)-anilino)-1-phenyl-methylene]-6-methoxycarbonyl-2-indolinone
(411) 3-Z-[1-(4-((2-amino-ethyl)-amino-methyl)-anilino)-1-phenyl-methylene]-6-methoxycarbonyl-2-indolinone
(412) 3-Z-[1-(4-((3-amino-propyl)-amino-methyl)-anilino)-1-phenyl-methylene]-6-methoxycarbonyl-2-indolinone
(413) 3-Z-[1-(4-((2-acetylamino-ethyl)-amino-methyl)-anilino)-1-phenyl-methylene]-6-methoxycarbonyl-2-indolinone
(414) 3-Z-[1-(4-((3-acetylamino-propyl)-amino-methyl)-anilino)-1-phenyl-methylene]-6-methoxycarbonyl-2-indolinone
(415) 3-Z-[1-(4-((2-methylsulphonylamino-ethyl)-amino-methyl)-anilino)-1-phenyl-methylene]-6-methoxycarbonyl-2-indolinone
(416) 3-Z-[1-(4-((3-methylsulphonylamino-propyl)-aminomethyl)-anilino)-1-phenyl-methylene]-6-methoxycarbonyl-2-indolinone
(417) 3-Z-[1-(4-(N—(N-tert.butoxycarbonyl-2-amino-ethyl)-N-methyl-amino-methyl)-anilino)-1-phenyl-methylene]-6-methoxycarbonyl-2-indolinone
(418) 3-Z-[1-(4-(N-(2-amino-ethyl)-N-methyl-amino-methyl)-anilino)-1-phenyl-methylene]-6-methoxycarbonyl-2-indolinone
(419) 3-Z-[1-(4-(N-(2-acetylamino-ethyl)-N-methyl-aminomethyl)-anilino)-1-phenyl-methylene]-6-methoxycarbonyl-2-indolinone
(420) 3-Z-[1-(4-(N-(2-methylsulphonylamino-ethyl)-N-methyl-amino-methyl)-anilino)-1-phenyl-methylene]-6-methoxycarbonyl-2-indolinone (421) 3-Z-[1-(4-(carboxymethyl-amino-methyl)-anilino)-1-phenyl-methylene]-6-methoxycarbonyl-2-indolinone
(422) 3-Z-1 1-(4-(ethoxycarbonylmethyl-amino-methyl)-anilino)-1-phenyl-methylene]-6-methoxycarbonyl-2-indolinone
(423) 3-Z-[1-(4-(carbamoylmethyl-amino-methyl)-anilino)-1-phenyl-methylene]-6-methoxycarbonyl-2-indolinone
(424) 3-Z-[1-(4-(dimethylcarbamoyl-methyl-amino-methyl)-anilino)-1-phenyl-methylene]-6-methoxycarbonyl-2-indolinone
(425) 3-Z-[1-(4-(methylcarbamoyl-methyl-amino-methyl)-anilino)-1-phenyl-methylene]-6-methoxycarbonyl-2-indolinone
(426) 3-Z-[1-(4-(N-dimethyl-aminomethylcarbonyl-N-methyl-amino)-3-amino-anilino)-1-phenyl-methylene]-6-rnethoxycarbonyl-2-indolinone
(427) 3-Z-[1-(4-(N-dimethyl-aminomethylcarbonyl-N-methyl-amino)-3-nitro-anilino)-1-phenyl-methylene]-6-methoxycarbonyl-2-indolinone
(428) 3-Z-[1-(4-(N-dimethyl-aminomethylcarbonyl-N-methyl-amino)-3-acethylamino-anilino)-1-phenyl-methylene]-6-methoxycarbonyl-2-indolinone
(429) 3-Z-[1-(4-(N-dimethyl-aminomethylcarbonyl-N-methyl-amino)-3-methylsulphonyl amino-anilino)-1-phenyl-methylene]-6-methoxycarbonyl-2-indolinone
(430) 3-Z-[1-(4-(N-dimethyl-aminomethylcarbonyl-N-methyl-amino)-3-cyano-anilino)-1-phenyl-methylene]-6-rnethoxycarbonyl-2-indolinone
(431) 3-Z-[1-(4-(N-dimethyl-aminomethylcarbonyl-N-methyl-amino)-3-hydroxy-anilino)-1-phenyl-methylene]-6-methoxycarbonyl-2-indolinone
(432) 3-Z-[1-(4-(N-dimethyl-aminomethylcarbonyl-N-methylamino)-3-methoxy-anilino)-1-phenyl-methylene]-6-methoxycarbonyl-2-indolinone
(433) 3-Z-[1-(4-(N-dimethyl-aminomethylcarbonyl-N-methyl-amino)-3-ethoxycarbonylanilino)-1-phenyl-methylene]-6-methoxycarbonyl-2-indolinone
(434) 3-Z-[1-(4-(N-dimethylaminomethylcarbonyl-methyl-amino)-3-carboxy-anilino)-1-phenyl-methylene]-6-methoxycarbonyl-2-indolinone
(435) 3-Z-[1-(4-(N-dimethylaminomethylcarbonyl-methyl-amino)-3-carbamoyl-anilino)-1-phenylmethylene]-6-methoxycarbonyl-2-indolinone
(436) 3-Z-[1-(4-(N-dimethyl-aminomethylcarbonyl-N-methyl-amino)-3-chloro-anilino)-1-phenyl-methylene]-6-methoxycarbonyl-2-indolinone
(437) 3-Z-[1-(4-(N-dimethyl-aminomethylcarbonyl-N-methyl-amino)-3-fluoro-anilino)-1-phenyl-methylene]-6-methoxycarbonyl-2-indolinone
(438) 3-Z-[1-(4-(N-di methyl-aminomethylcarbonyl-N-methyl-amino)-3-bromo-anilino)-1-phenyl-methylene]-6-methoxycarbonyl-2-indolinone
(439) 3-Z-[1-(4-(N-dimethylaminomethylcarbonyl-N-methyl-amino)-3-methyl-anilino)-1-phenyl-methylene]-6-methoxycarbonyl-2-indolinone
(440) 3-Z-[1-(4-(N-dimethyl-aminomethylcarbonyl-N-methyl-amino)-3-trifluoromethyl-anilino)-1-phenyl-methylene]-6-methoxycarbonyl-2-indolinone
(441) 3-Z-[1-(4-(N-dimethyl-aminomethylcarbonyl-N-methyl-amino)-3,5-dibromo-anilino)-1-phenyl-methylene]-6-methoxycarbonyl-2-indolinone
(442) 3-Z-[1-(4-(N-dimethyl-aminomethylcarbonyl-N-methyl-amino)-3,5-dichloro-anilino)-1-phenyl-methylene]-6-methoxycarbonyl-2-indolinone
(443) 3-Z-[1-(4-(dimethyl-aminomethylI-3-amino-anilino)-1-phenyl-methylene]-6-methoxycarbonyl-2-indolinone
(444) 3-Z-[1-(4-(dimethyl-aminomethyl)-3-nitro-anilino)-1-phenyl-methylene]-6-methoxycarbonyl-2-indolinone
(445) 3-Z-[1-(4-(dimethyl-aminomethyl)-3-acetylamino-anilino)-1-phenyl-methylene]-6-methoxycarbonyl-2-indolinone
(446) 3-Z-[1-(4-(dimethyl-aminomethyl)-3-methylsulphonylaminoanilino)-1-phenyl-methylene]-6-methoxycarbonyl-2-indolinone
(447) 3-Z—C1-(4-(dimethyl-aminomethyl)-3-cyano-anilino)-1-phenyl-methylene]-6-methoxycarbonyl-2-indolinone
(448) 3-Z-[1-(4-(dimethylaminomethyl)-3-hydroxyanilino)-1-phenyl-methylene]-6-lmethoxycarbonyl-2-indolinone
(449) 3-Z-[1-(4-(dimethyl-aminomethyl)-3-methoxy-anilino)-1-phenyl-methylene]-6-methoxy-carbonyl-2-indolinone
(450) 3-Z-[1-(4-(dimethyl-aminomethyl)-3-ethoxycarbonylanilino)-1-phenyl-methylene]-6-metho-1-2-indolinone
(451) 3-Z-[1-(4-(dimethyl-aminomethyl)-3-carboxy-anilino)-1-phenyl-methylene]-6-methoxycarbonyl-2-indolinone
(452) 3-Z—C1-(4-(dimethyl-aminomethyl)-3-carbamoyl-anilino)-1-phenyl-methylene]-6-methoxycarbonyl-2-indolinone
(453) 3-Z-[1-(4-(dimethyl-aminomethyl)-3-chloro-anilino)-1-phenyl-methylene]-6-methoxycarbonyl-2-indolinone
(454) 3-Z-1 1-(4-(dimethyl-aminomethyl)-3-fluoro-anilino)-1-phenyl-methylene]-6-methoxycarbonyl-2-indolinone
(455) 3-Z-[1-(4-(dimethyl-aminomethyl)-3-bromo-anilino)-1-phenyl-methylene]-6-methoxycarbonyl-2-indolinone
(456) 3-Z-[1-(4-(dimethyl-aminomethyl)-3-methyl-anilino)-1-phenyl-methylene]-6-methoxycarbonyl-2-indolinone
(457) 3-Z-[1-(4-(dimethyl-aminomethyl)-3-trifluoromethyl-anilino)-1-phenyl-methylene]-6-methoxycarbonyl-2-indolinone
(458) 3-Z-[1-(4-dimethylaminomethyl-3,5-dibromoanilino)-1-phenyl-methylene]-6-methoxycarbonyl-2-indolinone
(459) 3-Z-[1-(4-(dimethyl-aminomethyl)-3,5-dichloro-anilino)-1-phenyl-methylene]-6-methoxy-carbonyl-2-indolinone
(460) 3-Z-[1-(4-(dimethyl-aminomethyl)-anilino)-1-phenyl-methylene]-6-[(2-hydroxy-ethoxy)-carbonyl-2-indolinone
(461) 3-Z-[1-(4-(dimethyl-aminomethyl)-anilino)-1-phenyl-methylene]-6-[(ethoxycarbonyl-methoxy)-carbonyl-2-indolinone
(462) 3-2-[1-(4-(dimethyl-aminomethyl)-anilino)-1-phenyl-methylene]-6-[(carboxy-methoxy)-carbonyl-2-indolinone
(463) 3-Z-[1-(4-(dimethyl-aminomethyl)-anilino)-1-phenyl-methylene]-6-[(carbamoyl-methoxy)-carbonyl-2-indolinone
(464) 3-Z-[1-(4-(N-dimethyl-aminomethylcarbonyl-N-methyl-amino)-anilino)-1-phenyl-methylene]-6[-(2-hydroxy-ethoxylcarbonyl-2-indolinone
(465) 3-Z-[1-(4-(N-dimethyl-aminomethylcarbonyl-N-methyl-amino)-anilino)-1-phenyl-methylene]-6[-(ethoxycarbonylmethoxy)-carbonyl-2-indolinone
(466) 3-Z-[1-(4-(N-dimethyl-aminomethylcarbonyl-N-methyl-amino)-anilino)-1-phenyl-methylene]-6-[(carboxy-methoxy)-carbonyl-2-indolinone
(467) 3-Z-[1-(4-(N-dimethyl-aminomethylcarbonyl-N-methyl-amino)-anilino)-1-phenyl-methylene]-6-[(carbamoyl-methoxy)-carbonyl-2-indolinone (468) 3-Z-[1-(4-(N-dimethyl-aminomethylcarbonyl-N-methyl-amino)-anilino)-1-phenyl-methylene]-6-[(2-methoxy-ethoxy)-carbonyl-2-indolinone
(469) 3-Z-[1-(4-(N-dimethyl-aminomethylcarbonyl-N-methyl-amino)-anilino)-1-phenyl-methylene]-6[-(2-dimethyl-aminoethoxy)-carbonyl]-2-indolinone
(470) 3-Z-[1-(4-(N-dimethyl-aminomethylcarbonyl-N-methyl-amino)-anilino)-1-phenyl-methylene]-6-[(2-(N-tert-butoxycarbonyl-amino)-ethoxy)-carbonyl]-2-indolinone
(471) 3-Z-[1-(4-(N-dimethyl-aminomethylcarbonyl-N-methyl-amino)-anilino)-1-phenyl-methylene]-6-[(2-amino-ethoxy)-carbonyl]-2-indolinone
(472) 3-Z-[1-(4-(N-di methyl-aminomethylcarbonyl-N-methyl-amino)-anilino)-1-phenyl-methylene]-6-[(2,2,2-trifluoroethoxy)-carbonyl]-2-indolinone
(473) 3-Z-[1-(4-(N-((4-methyl-piperazin-1-yl)-methylcarbonyl)-N-methyl-amino)-anilino)-1-phenyl-methylene]-6-methoxycarbonyl-2-indolinone
(474) 3-Z-[1-(4-(N-(imidazo-1-yl-methyl carbonyl)-N-methyl-amino)-anilino)-1-phenyl-methylene]-6-methoxycarbonyl-2-indolinone
(475) 3-Z-[1-(4-(N-(phthalimido-2-yl-methylcarbonyl)-N-methyl-amino)-anilino)-1-phenyl-methylene]-6-methoxycarbonyl-2-indolinone
(476) 3-Z-[1-(4-(N-aminomethylcarbonyl-N-methyl-amino)-anilino)-1-phenyl-methylene]-6-methoxy carbonyl-2-indolinone
(477) 3-Z-[1-(4-(N-acethylaminomethylcarbonyl-N-methyl-amino)-anilino)-1-phenyl-methylene]-6-methoxycarbonyl-2-indolinone
(478) 3-Z-[1-(4-(N-methyl sulphonylaminomethylcarbonyl-N-methyl-amino)-anilino)-1-phenyl-methylene]-6-methoxycarbonyl-2-indolinone
(479) 3-Z-[1-(4-(N—((N-(2-methoxyethyl)-N-methyl-amino)-methylcarbonyl)-N-methyl-amino)-anilino)-1-phenyl-methylene]-6-methoxycarbonyl-2-indolinone
(480) 3-Z-[1-(4-(N—((N-(2-dimethyl-aminoethyl))-N-methyl-amino)-methylcarbonyl)-N-methyl-amino)-anilino)-1-phenyl-methylene]-6-methoxycarbonyl-2-indolinone
(481) 3-Z-[1-(4-(N-((di-(2-hydroxyethyl)-amino)-methylcarbonyl)-N-methyl-amino)-anilino)-1-phenyl-methylene]-6-methoxycarbonyl-2-indolinone
(483) 3-Z-[1-(4-(N-dimethyl-aminomethylcarbonyl-N-methyl-amino)-anilino)-methylene]-6-methoxycarbonyl-2-indolinone
(484) 3-Z-[1-(4-(N-dimethyl-aminomethylcarbonyl-N-methyl-amino)-anilino)-ethylidene]-6-methoxycarbonyl-2-indolinone
(485) 3-Z-[1-(4-(N-dimethyl-aminomethylcarbonyl-N-methyl-amino)-anilino)-propylidene]-6-methoxycarbonyl-2-indolinone
(486) 3-Z-[1-(4-(N-dimethylaminomethylcarbonyl-N-methyl-amino)-anilino)-butylidene]-6-methoxycarbonyl-2-indolinone
(487) 3-Z-[1-(4-(dimethyl-aminomethyl)-anilino)-methylene]-6-methoxycarbonyl-2-indolinone
(488) 3-Z-[1-(4-(dimethyl-aminomethyl)-anilino)-ethylidene]-6-methoxycarbonyl-2-indolinone
(489) 3-Z-[1-(4-(dimethyl-aminomethyl)-anilino)-propylidene]-6-methoxycarbonyl-2-indolinone
(490) 3-Z-[1-(4-(dimethyl-aminomethyl)-anilino)-butylidene]-6-methoxycarbonyl-2-indolinone
(491) 3-Z-[1-(4-tert-butyloxycarbonyl-anilino)-1-phenylmethylene]-6-methoxycarbonyl-2-indolinone
(492) 3-Z-1 1-(4-(N-(2-dimethyl-amino-ethyl)-N-methyl-amino)-anilino)-1-phenyl-methylene]-6-methoxycarbonyl-2-indolinone
(493) 3-Z-[1-(4-(N-(3-dimethyl-amino-propyl)-N-methyl-amino)-anilino)-1-phenyl-methylene]-6-methoxycarbonyl-2-indolinone
(494) 3-Z-[1-(4-(N-methyl-acetylamino)-anilino)-1-phenyl-methylene]-6-methoxycarbonyl-2-indolinone
(495) 3-Z-[1-(4-(imidazol-4-yl)-anilino)-1-phenylmethylene]-6-methoxycarbonyl-2-indolinone
(496) 3-Z-[1-(4-((N-(dioxolan-2-yl-methyl)-N-methyl-amino)-methyl)-anilino)-1-phenyl-methylene]-6-methoxycarbonyl-2-indolinone
(497) 3-Z-[1-(4-(N-benzyl-N-methyl-amino-methyl)-anilino)-1-methyl-methylene]-6-carbamoyl-2-indolinone
(498) 3-2-[1-(4-(2,3,4,5-tetrahydro-benzo(d)azepin-3-ylmethyl)-anilino)-1-methyl-methylene]-6-carbamoyl-2-indolinone
(499) 3-Z-[1-(4-((benzo(1,3)dioxol-5-yl-methyl)-methyl-amino-methyl)-anilino)-1-methyl-methylene]-6-carbamoyl-2-indolinone
(500) 3-Z-[1-(4-(N-phenethyl-N-methyl-amino-methyl)-anilino)-1-methyl-methylene]-6-carbamoyl-2-indolinone
(501) 3-Z-[1-(4-(N-(3,4-dimethoxy-benzyl)-N-methyl-aminomethyl)-anilino)-1-methyl-methylene1-6-carbamoyl-2-indolinone
(502) 3-Z-[1-(4-(N-(4-Chloro-benzyl)-N-methyl-aminomethyl)-anilino)-1-methyl-methylene]-6-carbamoyl-2-indolinone
(504) 3-Z-[1-(4-(N-(4-fluoro-benzyl)-N-methyl-aminomethyl)-anilino)-1-methyl-methylene]-6-carbamoyl-2-indolinone
(505) 3-Z-[1-(4-(N-(4-bromo-benzyl)-N-methyl-aminomethyl)-anilino)-1-methyl-methylene]-6-carbamoyl-2-indolinone
(506) 3-Z-[1-(4-((N-(2-methoxy-ethyl)-N-methyl-amino)-methyl)-anilino)-1-phenyl-methylene]-6-methoxycarbonyl-2-indolinone
(507) 3-Z-[1-(4-(dimethyl-aminomethyl)-anilino)-1-phenyl-methylene]-6-[(2-amino-ethoxy)-carbonyl]-2-indolinone, wherein the use of 3-Z-[1-(4-(N-((4-methyl-piperazin-1-yl)-methylcarbonyl)-N-methyl-amino)-anilino)-1-phenyl-methylene]-6-methoxycarbonyl-2-indolinone also termed (BIBF1120) in the context of the invention is particularly preferred.

As used herein, "endostatin" refers to naturally occurring mammalian endostatin, preferably naturally occurring human endostatin, including the wild-type form as wells as naturally occurring splice variants, naturally occurring isoforms, and naturally occurring glycosylation variants.

As used herein, "angiostatin" refers to naturally occurring mammalian angiostatin, preferably naturally occurring human angiostatin, including the wild-type form as wells as naturally occurring splice variants, naturally occurring isoforms, and naturally occurring glycosylation variants.

As used herein, "VEGF" refers to naturally occurring mammalian VEGF, preferably naturally occurring human VEGF, including the wild-type form as well as naturally occurring splice variants, naturally occurring isoforms, and naturally occurring glycosylation variants. As used herein, "PDGF" refers to naturally occurring mammalian PDGF, preferably naturally occurring human PDGF, including the wild-type form as well as naturally occurring splice variants, naturally occurring isoforms, and naturally occurring glycosylation variants. As used herein, "FGF2" refers to naturally occurring mammalian FGF2, preferably naturally occurring human FGF2, including the wild-type form as well as naturally occurring splice variants, naturally occurring isoforms, and naturally occurring glycosylation variants.

As used herein, the term "VEGF receptor" comprises without limitation Flt-1 (Fms-related tyrosine kinase 1, also known as vascular endothelial growth factor/vascular permeability factor receptor), Flk/KDR, and Flt-4 (Fms-related tyrosine kinase 4). As used herein, the term "FGF receptor" comprises without limitation FGF receptor 1, FGF receptor 2, FGF receptor 3, and FGF receptor 4. As used herein, the term "PDGF receptor" comprises without limitation PDGF receptor alpha and PDGF receptor beta. The reference to the above mentioned receptors (i.e. VEGF receptor, FGF receptor, PDGF receptor, Flt-1, Flk/KDR, Flt-4, FGF receptor 1, FGF receptor 2, FGF receptor 3, FGF receptor 4, PDGF receptor alpha, and PDGF receptor beta) includes the naturally occurring receptors from any mammalian species and preferably refers to the naturally occurring human receptors, including the respective wild-type form as well as naturally occurring splice variants, naturally occurring isoforms and naturally occurring glycosylation variants.

As used herein, "erythropoietin (EPO)" refers to naturally occurring mammalian erythropoietin, preferably naturally occurring human erythropoietin, including the wild-type form and naturally occurring splice variants and naturally occurring glycosylation variants thereof, as well as any EPO protein variant described in US patent application 2008/0194475 A1. The terms "erythropoietin" or "EPO" as used herein, preferably refer to the human EPO and any variant thereof as described in paragraphs [0003] to [0010] of US 2008/0194475 A1.

In preferred embodiments, the antibodies usable in any aspect of the present invention exhibit an antagonist activity, i.e. by specifically binding to their target protein these antibodies block at least one activity of their target protein. In preferred embodiments, the antibodies usable in the present invention block binding between a signaling protein (e.g. VEGF, FGF2, or PDGF) and its corresponding receptor.

In a first aspect the present invention is directed to a method of treating a patient suffering from a disease or disorder of the nervous system, said method comprising administering an effective amount of neural precursor cells in combination with an effective amount of at least one inhibitor of chemoattraction. The at least one inhibitor of chemoattraction can be administered prior to, simultaneously with or subsequently to the administration of neural precursor cells.

In a preferred embodiment of the first aspect, the patient suffers from loss of neuronal or glial cells caused by traumatic, ischemic, degenerative, genetic, hypoxic, metabolic, infectious, neoplastic, or toxic disorders of the nervous system. In preferred embodiments, the loss of neuronal or glial cells is the result of traumatic lesions of the brain or spinal cord, ischemic infarctions, hemorrhagic infarctions, Parkinson's disease, Huntington's disease, Alzheimer's disease, hereditary atrophic disorders of the cerebellum or brain stem, motoneuron diseases, spinal muscular atrophies, age-related changes, multiple sclerosis, adrenoleukodystrophy, or Pelizaeus-Merzbacher disease.

In a further preferred embodiment of the first aspect, the patient suffers from a hereditary metabolic disorder or neoplastic disorder of the nervous system.

In a second aspect the present invention is directed to a method of enhancing the effectiveness of therapy with neural precursor cells, said method comprising administering an effective amount of an inhibitor of chemoattraction to a patient undergoing said therapy with neural precursor cells.

In a preferred embodiment of the second aspect, the inhibitor of chemoattraction is preferably selected from: endostatin, angiostatin, or variants or derivatives thereof; a VEGF inhibitor, in particular an antibody specifically binding to VEGF; a VEGF receptor inhibitor, in particular an antibody specifically binding to VEGF receptor; a FGF2 inhibitor, in particular an antibody specifically binding to FGF2; a FGF-2 receptor inhibitor, in particular an antibody specifically binding to FGF2 receptor; a PDGF inhibitor, in particular an antibody specifically binding to PDGF; a PDGF receptor inhibitor, in particular an antibody specifically binding to PDGF receptor; or erythropoietin (EPO), or variants or derivatives thereof.

In a preferred embodiment of the second aspect, the patient suffers from loss of neuronal or glial cells caused by traumatic, ischemic, degenerative, genetic, hypoxic, metabolic, infectious, neoplastic, or toxic disorders of the nervous system. In preferred embodiments, the loss of neuronal or glial cells is the result of traumatic lesions of the brain or spinal cord, ischemic infarctions, hemorrhagic infarctions, Parkinson's disease, Huntington's disease, Alzheimer's disease, hereditary atrophic disorders of the cerebellum or brain stem, motoneuron diseases, spinal muscular atrophies, age-related changes, multiple sclerosis, adrenoleukodystrophy, or Pelizaeus-Merzbacher disease.

In a further preferred embodiment of the second aspect, the patient suffers from a hereditary metabolic disorder or neoplastic disorder of the nervous system.

In a third aspect the present invention is directed to at least one inhibitor of chemoattraction in combination with neural precursor cells for use in the treatment or prevention of a disease or disorder of the nervous system.

In a preferred embodiment of the third aspect, the at least one inhibitor of chemoattraction is formulated for an administration prior to, simultaneously with or subsequently to the administration of the neural precursor cells.

In a preferred embodiment of the third aspect, the inhibitor of chemoattraction is preferably selected from: endostatin, angiostatin, or variants or derivatives thereof; a VEGF inhibitor, in particular an antibody specifically binding to VEGF; a VEGF receptor inhibitor, in particular an antibody specifically binding to VEGF receptor; a FGF2 inhibitor, in particular an antibody specifically binding to FGF2; a FGF-2 receptor inhibitor, in particular an antibody specifically binding to FGF2 receptor; a PDGF inhibitor, in particular an antibody specifically binding to PDGF; a PDGF receptor inhibitor, in particular an antibody specifically binding to PDGF receptor; or erythropoietin (EPO), or variants or derivatives thereof.

In a preferred embodiment of the third aspect, the disease or disorder of the nervous system is loss of neuronal or glial cells as result of traumatic, ischemic, degenerative, genetic, hypoxic, metabolic, infectious, neoplastic, or toxic disorders of the nervous system. In preferred embodiments, the loss of neuronal or glial cells is the result of traumatic lesions of the brain or spinal cord, ischemic infarctions, hemorrhagic infarctions, Parkinson's disease, Huntington's disease, Alzheimer's disease, hereditary atrophic disorders of the cerebellum or brain stem, motoneuron diseases, spinal muscular atrophies, age-related changes, multiple sclerosis, adrenoleukodystrophy, or Pelizaeus-Merzbacher disease.

In a further preferred embodiment of the third aspect, the disorder is a hereditary metabolic disorder or neoplastic disorder of the nervous system.

In a fourth aspect the present invention is directed to a use of an inhibitor of chemoattraction for the preparation of a pharmaceutical composition for enhancing the effectiveness of a therapy with neural precursor cells.

In a preferred embodiment of the fourth aspect, the inhibitor of chemoattraction is selected without limitation from: endostatin, angiostatin, or variants or derivatives thereof; a VEGF inhibitor, in particular an antibody specifically binding to VEGF; a VEGF receptor inhibitor, in particular an antibody specifically binding to VEGF receptor; a FGF2 inhibitor, in particular an antibody specifically binding to FGF2; a FGF-2 receptor inhibitor, in particular an antibody specifically binding to FGF2 receptor; a PDGF inhibitor, in particular an antibody specifically binding to PDGF; a PDGF receptor inhibitor, in particular an antibody specifically binding to PDGF receptor; or erythropoietin (EPO), or variants or derivatives thereof.

In a preferred embodiment of the fourth aspect, the therapy with neural precursor cells is for the treatment of loss of neuronal or glial cells as a result of traumatic, ischemic, degenerative, genetic, hypoxic, metabolic, infectious, neoplastic, or toxic disorders of the nervous system. In preferred embodiments, the loss of neuronal or glial cells is the result of traumatic lesions of the brain or spinal cord, ischemic infarctions, hemorrhagic infarctions, Parkinson's disease, Huntington's disease, Alzheimer's disease, hereditary atrophic disorders of the cerebellum or brain stem, motoneuron diseases, spinal muscular atrophies, age-related changes, multiple sclerosis, adrenoleukodystrophy, or Pelizaeus-Merzbacher disease.

In a further preferred embodiment of the fourth aspect, the therapy with neural precursor cells is for the treatment of a hereditary metabolic disorder or neoplastic disorder of the nervous system.

In a fifth aspect the present invention is directed to a pharmaceutical composition comprising neural precursor cells and at least one inhibitor of chemoattraction.

In a preferred embodiment of the fifth aspect, the at least one inhibitor of chemoattraction is formulated for an administration prior to, simultaneously with or subsequently to the administration of the neural precursor cells.

In a preferred embodiment of the fifth aspect, the inhibitor of chemoattraction is selected without limitation from: endostatin, angiostatin, or variants or derivatives thereof; a VEGF inhibitor, in particular an antibody specifically binding to VEGF; a VEGF receptor inhibitor, in particular an antibody specifically binding to VEGF receptor; a FGF2 inhibitor, in particular an antibody specifically binding to FGF2; a FGF-2 receptor inhibitor, in particular an antibody specifically binding to FGF2 receptor; a PDGF inhibitor, in particular an antibody specifically binding to PDGF; a PDGF receptor inhibitor, in particular an antibody specifically binding to PDGF receptor; or erythropoietin (EPO), or variants or derivatives thereof.

In a preferred embodiment of the fifth aspect, the pharmaceutical composition further comprises one or more pharmaceutically acceptable carriers, diluents, excipients, fillers, binders, lubricants, glidants, disintegrants, adsorbents; and/or preservatives.

In the practice of any aspect of the present invention, the neural precursor cells may be administered to a patient by any route established in the art which provides a sufficient level of neural precursor cells. Preferably, the neural precursor cells are directly injected into the brain. This administration route includes, but is not limited to, the intracerebral, intraventricular, intracerebroventricular, intrathecal, intracisternal, intraspinal and/or perispinal routes of administration, which can employ intracranial and intravertebral needles, and catheters with or without pump devices.

In the practice of any aspect of the present invention, a pharmaceutical composition as described above or an inhibitor of chemoattraction may be administered to a patient by any route established in the art which provides a sufficient level of the inhibitor of chemoattraction. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the pharmaceutical composition of the present invention is administered locally it can be injected directly into the organ or tissue to be treated. In cases of treating the nervous system this administration route includes, but is not limited to, the intracerebral, intraventricular, intracerebroventricular, intrathecal, intracisternal, intraspinal and/or peri-spinal routes of administration, which can employ intracranial and intravertebral needles, and catheters with or without pump devices. The inhibitor of chemoattraction can also be provided by administering to the patient an effective amount of an agent that can increase the amount of endogenous inhibitor of chemoattraction (e.g. the amount of endogenous angiostatin, endostatin or EPO).

When the inhibitor of chemoattraction is not directly delivered into the brain, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine-thienylalanine-serine-proline-(4-Me-tyrosine)$\psi(CH_2NH)$-arginine-COOH). Alternatively, the factors can be conjugated to the transferrin receptor antibodies as described in U.S. Pat. Nos. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, an inhibitor of chemoattraction can be delivered in a controlled-release system. For example, the inhibitor may be administered using intravenous infusion, an implantable osmotic pump, a transdermal patch, liposomes, or other modes of administration. In one embodiment, a pump may be used (see Sefton (1987) CRC Crit. Ref. Biomed. Eng. 14: 201; Buchwald et al. (1980) Surgery 88:507; Saudek et al. (1989) N. Eng. J. Med. 321: 574). In another embodiment, the compound can be delivered in a vesicle, in particular a liposome (see Langer (1990) Science 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23: 61; see also Levy et al. (1985) Science 228:190; During et al. (1989) Ann. Neurol. 25: 351; Howard et al. (1989) J. Neurosurg. 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, Science 249: 1527-1533).

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutic composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

Examples

In the following, the invention is explained in more detail by non-limiting examples:

1. Methods

1.1 Transwell Migration Assay

One way to study migration at the cellular level is to use microchemotaxis chambers (Boyden chambers; see FIG. 1A) (Richards & McCullough, 1984). A membrane separates the upper and the lower part of the chamber. Cells are plated on the PO/LN coated membrane that separates the upper and the lower well. Chemoattractants are introduced in the well of the lower compartment e.g., by soaking agarose beads (affi-gel blue gel) with the corresponding chemoattractants. 100 μl of the pre-soaked beads are introduced in the lower well and covered with medium before placing the upper well on top. The chemoattractant will be released over time, thus creating a chemoattractive gradient. If the agent acts as a chemoattractant, the attached cells will migrate through the filter towards the gradient of the attracting factor. Small pore sizes (8 μm) require active migration rather than passive falling of the cells through the filter.

In this study agarose beads were soaked with either 30 ng/ml EGF, BDNF, SDF1, SCF, PDFG-AA, FGF2 or VEGF (FIG. 1B). The chemoattractive effect of NSCs on neurons was studied by plating lt-hESNSC directly in the PO/LN coated lower well before placing the upper well with the attached neurons on top. After a culture period of 20 hours, chambers were fixed with 4% PFA for 10 min. Cells that had not migrated and were still on the upper side of the membrane were scraped off, while the migrated cells on the lower side were DAPI stained and counted.

1.2 Transplantation onto Rat Hippocampal Slice Cultures

Using a vibroslicer, 400 μm horizontal sections were generated from the hippocampus of 9-10 day-old Wistar rats. The slices included the dentate gyrus and the entorhinal and temporal cortex (Scheffler et al., 2003; Opitz et al., 2007). They were transferred onto a polyester membrane and cultivated at 35° C., 5% $CO_2$ and saturated air humidity in an initial culture medium containing 25% normal horse serum, which was gradually replaced after 3-5 days by chemically defined, serum-free culture medium based on DMEM/F12, N2 supplement and B27 supplement. Medium was changed every other day and 5-7 days after explantation a cell suspension of 50 000 cells in a 1 μl volume was spotted onto the entorhinal cortex of the slice using an injection device.

For immunohistochemical analysis of slice cultures (FIG. 4), cultures were fixed in 4% paraformaldehyde for 4 hours and subsequently washed several times with PBS. Slices were permeabilized/blocked with 0.1% Triton X-100+10% FCS for 6 hours at 25° C. Incubation with primary antibody was for 16 hours at room temperature, followed by washing steps with PBS for 5 hours. Incubation with the secondary antibodies was for 2 hours at room temperature.

1.3 RT-PCR

For reverse transcriptase polymerase chain reaction (RT-PCR) triplicate total messenger RNA (mRNA) samples were isolated using an mRNA extraction kit, following the supplier's instructions. 0.5 to 1 μg total mRNA were used for reverse transcription with the iScript cDNA synthesis kit following the manufacturer's protocol. PCR reactions were run in at least triplicates using Taq Polymerase. In order to compare the expression levels of different genes, all data were normalized to GAPDH by performing 15, 20 and 25 cycles. PCR conditions and cycle numbers were then adjusted to each primer pair for specific DNA amplification on commercially available human fetal brain tissue (single donor, female, 19 weeks of gestation). The selected number of cycles varied from 28 to 35 cycles depending on the particular cDNA abundance with denaturation at 94° C. for 1 minute, annealing temperatures of 58° C. to 63° C. for 1 minute according to the primers, and elongation at 72° C. for 2 minutes. Omission of transcriptase during RT or cDNA sample during PCR served as negative controls. All reactions were performed on a T3 Thermocycler.

1.4 Immunocytochemistry

Immunocytochemical analyses of the cells were performed using primary antibodies and appropriate secondary antibodies labelled with Cy3, Cy5 or FITC. Nuclei were visualised by DAPI staining (1:10000 in PBS, 4 minutes incubation). Cells were fixed in 4% paraformaldehyde for 10 minutes. For the staining of intracellular markers cells were permeabilized with 0.1% Triton X-100 in PBS for 20 minutes. Blocking was performed with 10% FCS, in PBS for 1 hour. Samples were incubated with primary antibodies diluted in blocking solution at room temperature for 3 to 4 hours, washed twice in PBS and incubated with secondary antibody diluted in blocking solution for 45 minutes. The cells were washed in PBS, counterstained with DAPI and mounted with vectashield mounting solution.

Figure 6:
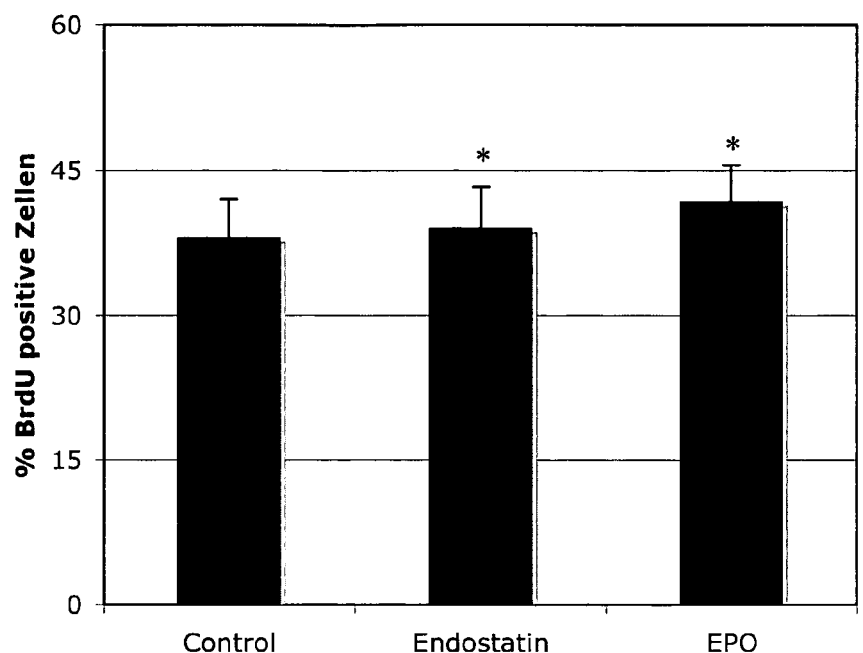
FIG. 6 shows the effect of endostatin and erythropoietin on lt-hESNSC.
Figure 6:
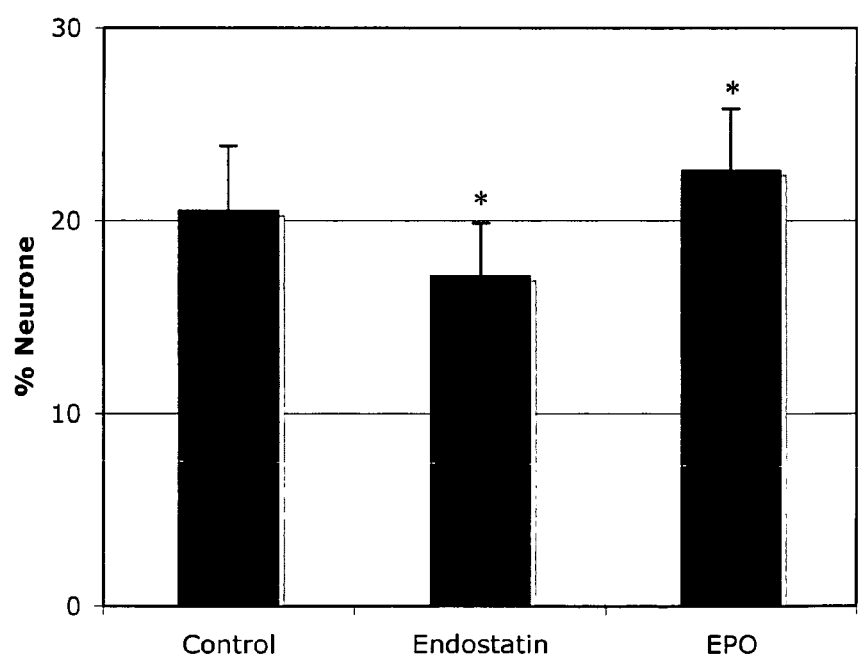

For BrdU staining (FIG. 6A) 0.5% Triton X-100 in PBS was used for permeabilizing the cells. After washing, cells were incubated with 2 M HCl for 10 minutes, washed in PBS, equilibrated using 0.1 M borate buffer, washed again in PBS, followed by an incubation with the primary antibody diluted in blocking solution at room temperature over night. Staining with the secondary antibody was performed as described.

1.5 Migration Assay Using a Dunn Chamber.

Chemotaxis of immature neurons was directly viewed and recorded in stable concentration gradients of FGF2 (200 ng/ml) or VEGF (200 ng/ml), respectively, with or without the addition of BIBF1120 (2 μg) using a Dunn chemotaxis chamber (Allen et al., 1998 1998, Zhang et al., 2003). This device is made from a Helber bacteria counting chamber by grinding a circular well in the central platform to leave a 1 mm-wide annular bridge between the inner and the outer well. Chemoattractants added to the outer well of the chamber will diffuse across the bridge to the inner well and form a linear steady gradient within ~30 min after loading the chamber (Zicha et al., 1991; Webb et al., 1996). To study chemotaxis, the outer well of the Dunn chamber can be filled with medium containing a chemoattractant, whereas the concentric inner well is filled with medium only. Coverslips carrying the cultured cells are inverted and placed onto the chamber. Cell locomotion is recorded through the annular bridge between the concentric inner and outer well. For assessing chemokinesis, the outer and inner wells are filled with equal concentrations of the chemoattractant. A period of 6 h was chosen to assess cell migration.

To determine the efficiency of forward migration during the 6 h recording period, the FMI was calculated as the ratio of forward progress to the total path length (Foxman et al., 1999; Zhang et al.).

1.6 BrdU Cell Proliferation Assay

5'-bromo-T-deoxyuridine (BrdU) is a thymidine analog that incorporates into dividing cells during DNA synthesis. To determine whether BIBF1120 has an influence on the proliferation rate of lt-hESNSC, cells were cultured under neural proliferation medium with or without BIBF1120 (2 μg/ml) for 20 h. BrdU was added to the culture medium for 2.5 h. To enable antibody binding to the incorporated BrdU cells must be fixed, permeabilized and the DNA denatured followed by immunohistochemical staining with anti-BrdU monoclonal antibody.

2. Results

Figure 2:
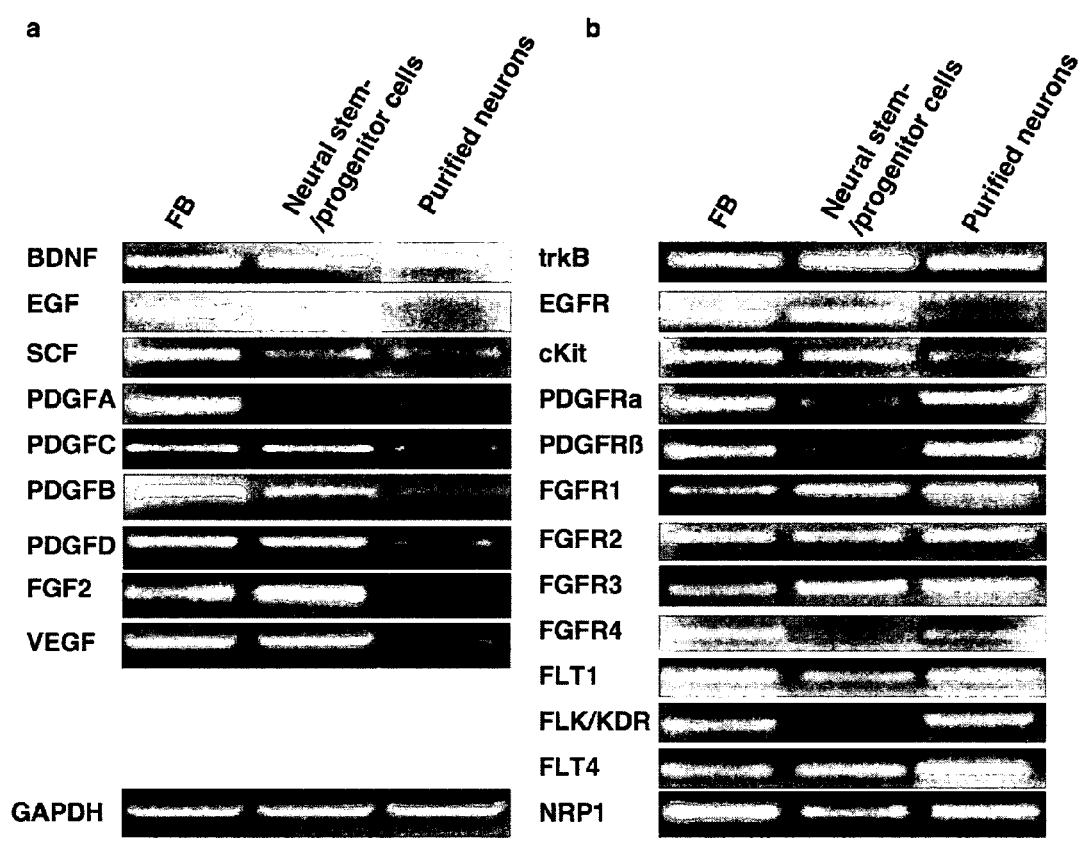
FIG. 2 shows expression profiles of chemoattractants and their respective receptor sets in neural stem/progenitor cells and immature neurons. RT-PCR analysis of the expression of the RNA transcript for (a) chemoattractants and (b) the respective receptor sets in neural stem/progenitor cells and neurons ("purified neurons"). Human fetal brain tissue (19 weeks of gestation) (FB) served as control.

Soluble factors such as SDF1, SCF, PDGF, FGF2 or VEGF have been shown to be neuronal chemoattractants (FIG. 1B). To determine whether the tested chemoattractants and their respective receptors are expressed by neural stem/progenitor cells and/or immature neurons, RT-PCR using RNA isolated from neural stem/progenitor cells and neurons, respectively were performed. The expression profile revealed that neural stem/progenitor cells strongly express transcripts for BDNF, EGF, SCF, PDGF (isoforms B, C and D), FGF2 and VEGF (FIG. 2 a). In contrast, neurons showed weak expression of the transcripts for EGF, SCF, PDGF (isoforms A, B, C and D), FGF2 and VEGF and a strong expression for BDNF. Furthermore, neurons strongly express transcripts for the BDNF receptor trkB, the SCF receptor c-kit, the PDGF receptors α and β, the FGF receptors 1 to 4 and the VEGF receptors Flt1, Flk/KDR and Flt4, as well as the co-receptor NRP1 (FIG. 2B). With exception of PDGF receptor α and β, FGF receptor 4 and the VEGF receptor Flk/KDR, transcripts for the above mentioned receptors were also expressed by the neural stem/progenitor cells (FIG. 2 b). These data show that several soluble chemoattractants are expressed in neural stem/progenitor cells, whereas neurons express the receptors associated to these factors. Considering the significant chemoattractive effect of VEGF, FGF2 and PDGF observed in the chamber migration assay (FIG. 1B), these factors are likely responsible for core formation of progenitor-containing neural grafts.

To assess whether FGF2 and VEGF play a role in preventing migration of immature neurons out of a cell mixture with neural stem/progenitor cells, different agents known to interfere with these signaling pathways were tested such as an anti-human VEGF receptor 2 antibody (VEGF R2-AB), known to neutralize the bioactivity of VEGF receptor Flk/KDR (Ferrara & Davis-Smyth, 1997) or the recombinant human protein endostatin, a cleavage product of collagen XVIII (Marneros & Olsen, 2005), which has been reported to have anti-angiogenesis effects (O'Reilly et al., 1997; Marneros & Olsen, 2001) and which inhibits endothelial cell migration in response to FGF2 and VEGF (Eriksson et al., 2003).

Figure 3:
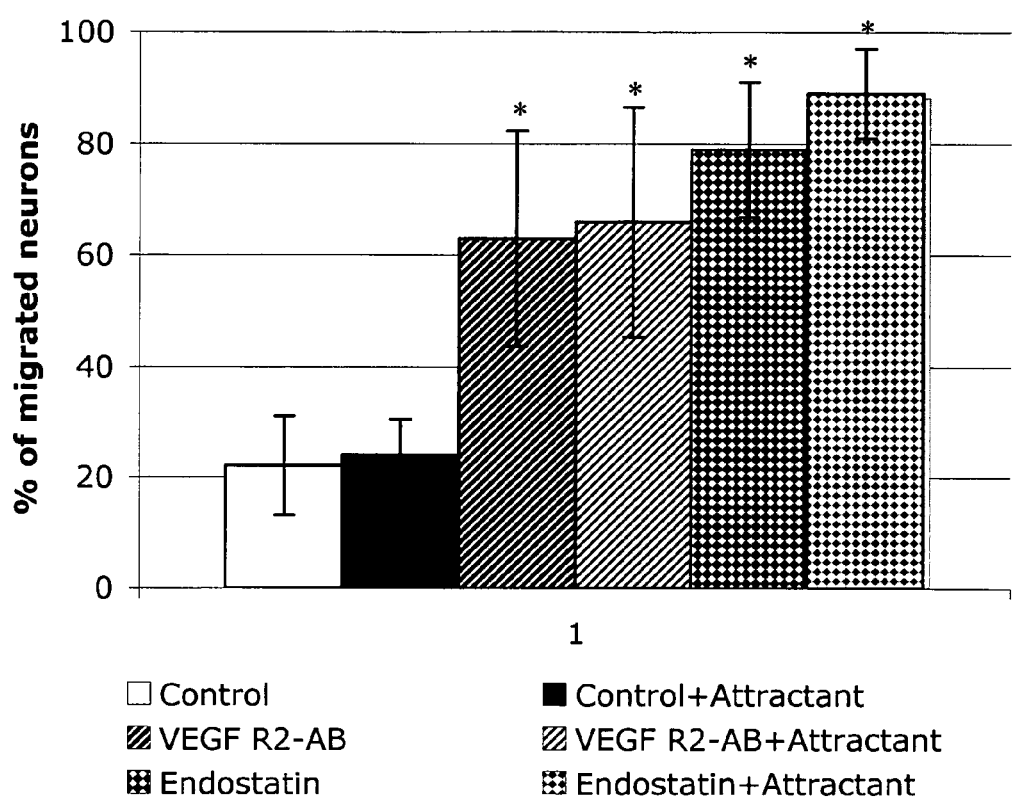
FIG. 3 shows a mini-chamber migration assay of lt-hESNSC (70%) mixed with immature neurons (30%) in the presence of VEGF R2-AB or endostatin. Bars represent the percentage of migrated neurons after 20 hours in culture towards medium or a chemoattractant either with or without VEGF R2-AB or endostatin treatment. Cell numbers were normalised to the number of plated neurons (*P≤0.02; statistical significance was determined in relation to the control).

To study whether any of the two molecules (VEGF R2-AB or endostatin) had an effect on the neuronal migration of immature neurons in the presence of neural stem/progenitor cells, Boyden chamber assays were performed. Human neural stem/progenitor cells and immature neurons mixed in a 70:30 ratio (further named: hES-NSC70+N30), which pre-incubated for 30 minutes in 30 μA Cytocon™ Buffer II with either 10 μl VEGF R2-AB stock solution, 2 μl endostatin stock solution or with the equivalent solvents, were placed in the upper well. The lower wells contained medium and either plain agarose beads or agarose beads soaked with PDGF as attractant. A significantly enhanced migration of immature neurons towards media was observed when pre-incubating the cell mixture with the VEGF R2-AB or endostatin. The chemoattractive gradient, which was caused by the agarose beads releasing PDGF, additionally enhanced the effect of the VEGF-R2-AB and endostatin pre-incubation (FIG. 3). The data of this Boyden chamber assay demonstrates that interfering with chemoattractive factors expressed by neural stem/progenitor cells reduces the auto-attractive effect of a mixed neural/neuronal population.

Figure 4:
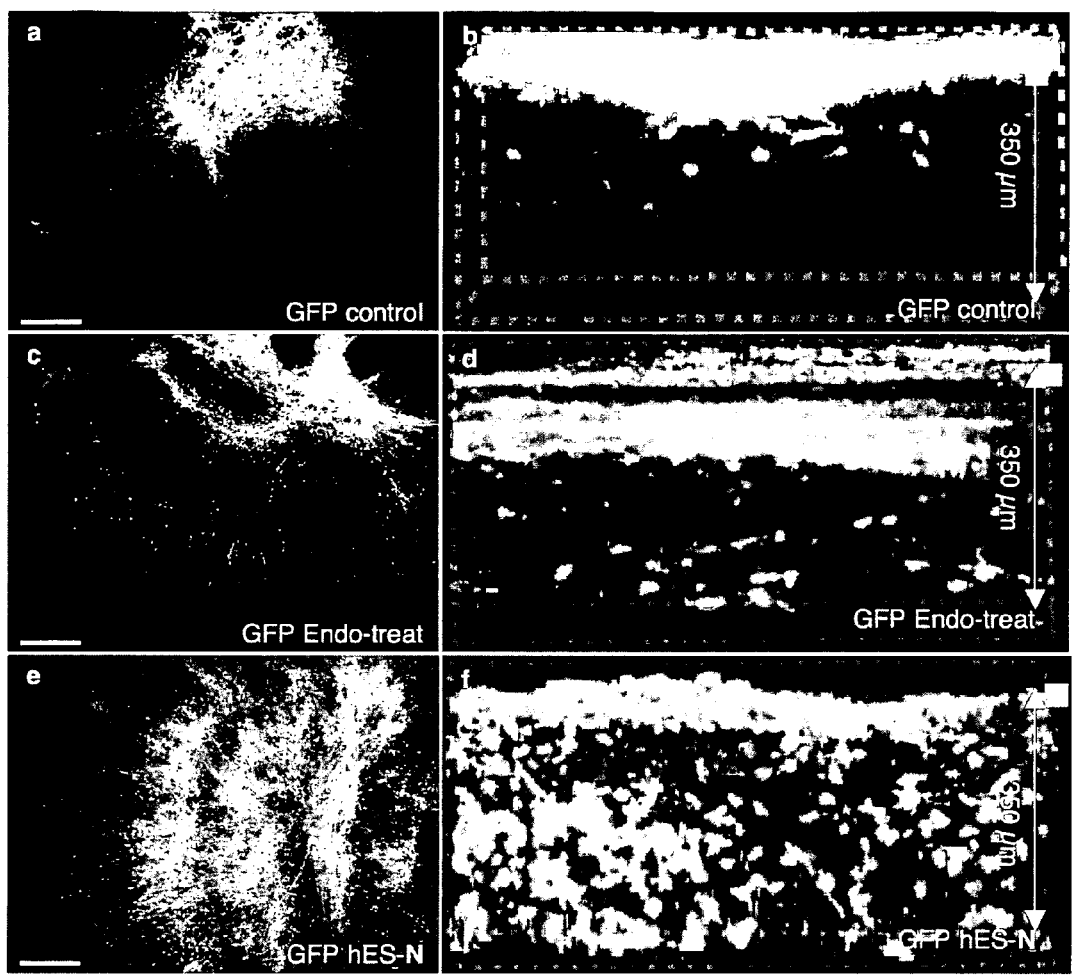
FIG. 4 shows interaction of neural stem cells with chemoattractants expressed by neural stem/progenitor cells on hippocampal rat slice cultures. Neuronal migration of lt-hESNSC (70%) mixed with immature neurons (30%) control population, of lt-hESNSC (70%) mixed with immature neurons (30%) endostatin treated population and of pure neurons (hES-N) on hippocampal rat slice cultures was studied. 18 days after transplantation (c,d) endostatin treated cells showed an enhanced migration and integration capacity as compared to (a,b) control cells both in the xy- as well as the z-axis. Highest migration rates were observed in (e,f) pure neurons. Slices (a,c,e) were DAPI and EGFP stained post fixation. Scale bars: a,c,e 500 µm.
Figure 5:
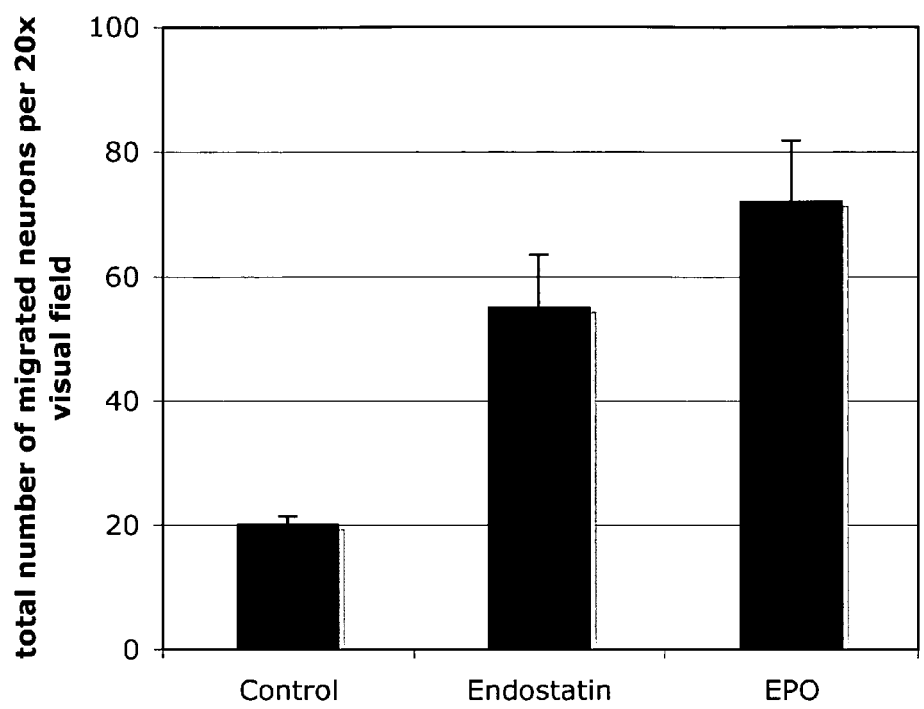
FIG. 5 shows a mini-chamber migration study of pre-differentiated lt-hESNSC (consisting of 50% neural stem/progenitor cells and 50% immature neurons) in the presence of endostatin or erythropoietin. Bars represent the total number of migrated neurons per 20× visual field after 20 hours in culture towards medium either with or without endostatin or erythropoietin treatment.
Figure 7:
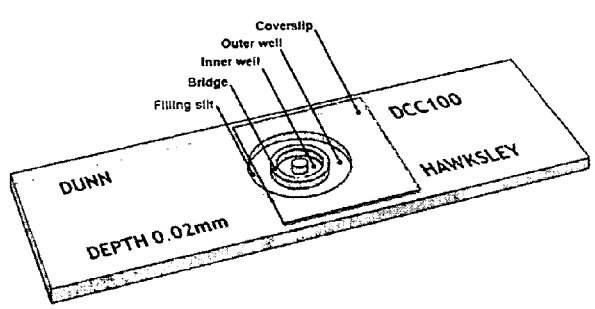
FIG. 7A Dunn chamber migration assay. Schematic representation of a direct-viewing Dunn chemotaxis chamber showing the position of the inner well, the bridge, the outer well and the overlying coverslip (a) (Zicha et al., 1991 1998, Zhang et al., 2003). Adopted from Hawksley. Calculation of the forward migration index (FMI) during a 6 h recording period. FMI values can be either positive or negative, depending on the direction in which the cell is migrating (b).
FIG. 7B Directionality analysis of cell movement using scatter plots of cell displacement (c-i). The diagrams orientate such that the position of the outer well of the chamber are vertical (y direction). Each point represents the final position of a cell at the end of the recording period of 6-h; the starting point of migration is fixed at the intersection of the two axes. As control migration of human neurons was monitored in medium only (c). For assessing chemokinesis, equal amounts of FGF2 (d) or VEGF (e) were added to both the outer and the inner wells of the chamber. Chemotaxis was tested by placing FGF2 (f) or VEGF (g) in the outer well only. Migration of human neurons treated with BFBF1120 was monitored towards a FGF2 (h) and VEGF (i) gradient. It is to be noted that neurons undergo chemotaxis and display a clear directionality of migration towards a FGF2 (f) or VEGF (g) gradient and loose this chemotactic response in the presence of BFBF1120 (h-i).
Figure 7:
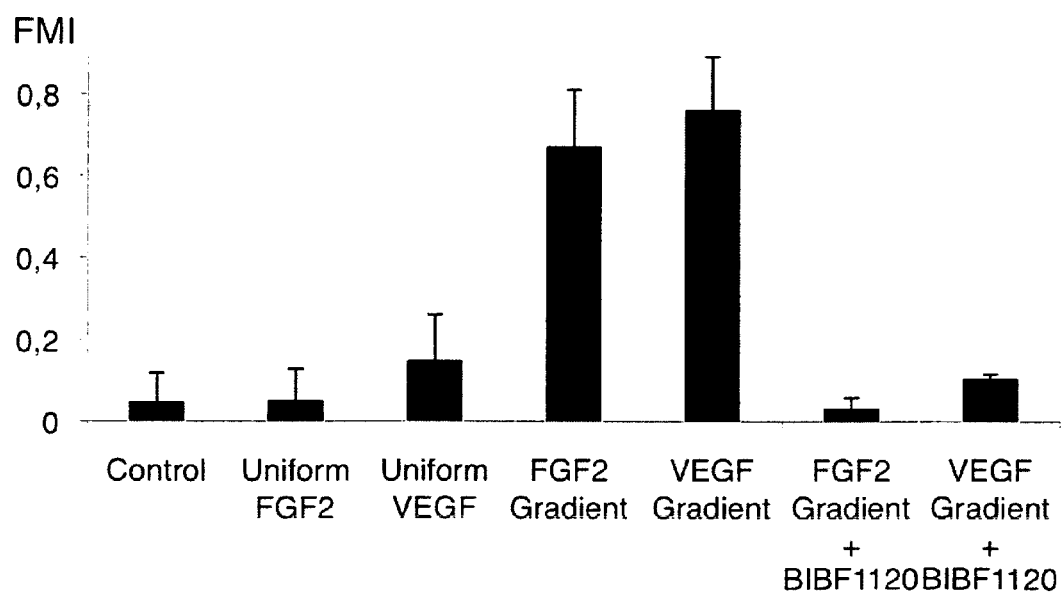
Figure 7:
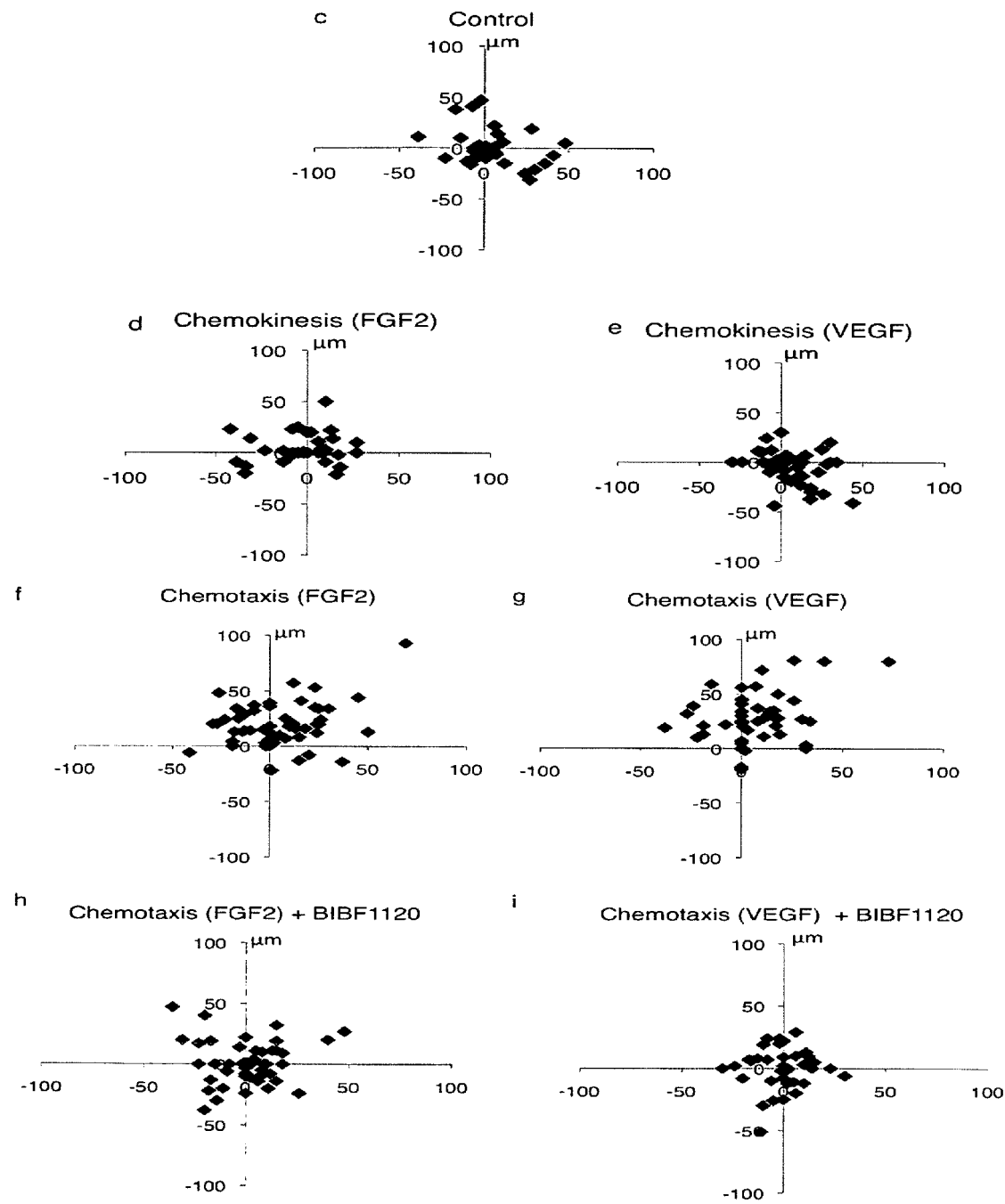

The previous results showed that pre-incubation of hES-NSC70+N30 with endostatin resulted in the most prominent enhancement of migration in a Boyden chamber assay. To further investigate whether endostatin can also interfere with the chemoattractive effect of neural stem/progenitor cells on immature neurons in a context closer to an in vivo situation, hippocampal rat slice culture experiments were performed. HES-NSC70+N30 were pre-incubated for 30 minutes in 30 μl Cytocon™-Buffer II with either 2 μl stock solution endostatin (n=9) or with 2 μl of the solvent of endostatin (citric-phosphate buffer) as control (n=9), and then deposited on the entorhinal cortex of hippocampal slice cultures. Cultures of pure human neurons were transplanted as positive control (n=9). The slices were further cultured for 18 days after deposition of the cells. 1 μl/ml endostatin stock solution was continuously applied every day to the slice media. When analyzing the cultures at day 18, endostatin treated cells showed an enhanced migration horizontally over the slice, compared to the control population. Migration of single human neurons up to 800 μm away from the transplantation core was frequently observed in the endostatin treated transplants, whereas the cells from the untreated control transplants never migrated further than 500 μm from the transplantation core. This enhancement of migration was also present along the z-axis, as the endostatin treated cells frequently reached depths of 350 μm (FIG. 4 d) whereas the non-treated cells never exceeded 200 μm (FIG. 4 b). These data shows that interference with the chemoattraction between neural stem/progenitor cells and immature neurons via applying endostatin strongly enhances the migration and integration capacity of mixed neural grafts. After confirming that VEGF and FGF2 are indeed neuronal chemoattractants (FIG. 7 a-g), the Dunn chamber was used to test the effect of the indolinone derivative BIBF1120, which is known to block VEGF receptor (VEGFR) and FGFR kinase activity (Hilberg et al., 2008), on the chemotactic response of human neurons towards FGF2 and VEGF. Indeed, neurons treated with BIBF1120 lost their chemotactic response to FGF2 and VEGF (FIG. 7 b, h-i).

Figure 8:
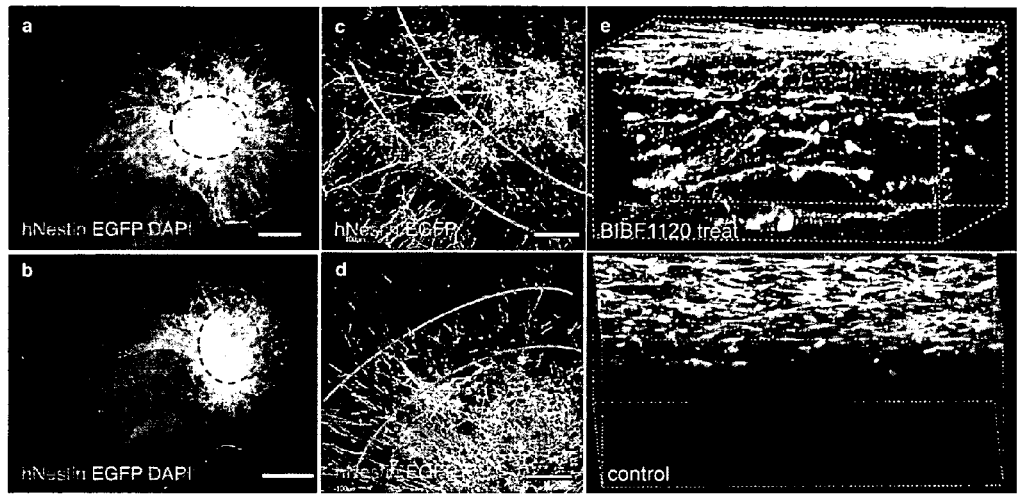
FIG. 8 Interaction of immature neurons with chemoattractants expressed by neural stem/progenitor cells on hippocampal rat slice cultures. Migration 7 days after transplantation of lt-hESNSC mixed with immature neurons (30.000 lt-hESNSC:100.000 immature neurons/up either in the presence of BIBF1120 (a, c, e; BIBF1120 treated) or in medium control (b, d, f). Note BIBF1120 treated cells showed an enhanced migration and integration capacity as compared to control cells in the xy- (a-d, g-h) and z-axis (e-f, i), respectively. Slices were DAPI, EGFP and hNestin stained post fixation (a-f). Confocal mapping and 3D reconstruction of slice cultures after deposition of BIBF-treated (e) and control cells (f). Quantification of the total numbers of neurons found in the xy-axis≥250 µm away from the deposition site (f) revealed a two-fold increase in the BIBF1120-treated group (h). Quantification of the total number of human neurons found within 10 µm optical planes placed through the middle and the bottom of the slice (i). Shown are values for the control-, the BIBF treated- and a pure neuronal reference population (100.000 immature neurons/µl). P<0.005.
Figure 8:
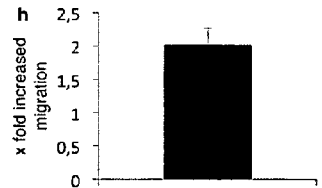
Figure 8:
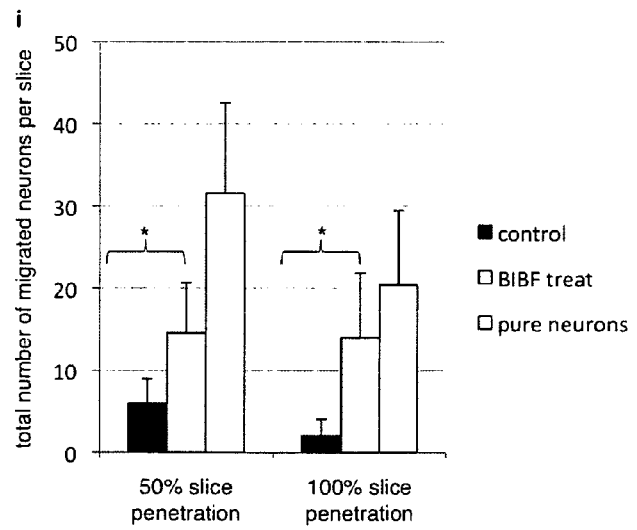

To further investigate whether BIBF1120 can also interfere with the chemoattractive effect of neural stem/progenitor cells on immature neurons, hippocampal rat slice culture experiments were performed. Lt-hESNSC mixed with purified DCX-EGFP positive neurons (30.0000 lt-hESNSC mixed with 100.000 purified neurons per μl) were pre-incubated for 30 min. in Cytocon™-Buffer II with or without 2 μg/ml BIBF1120, respectively, and then deposited on the entorhinal cortex (EC) of hippocampal slice cultures. The slices were further cultured for 7 days after deposition of the cells. 2 μg/ml BIBF1120 was continuously applied every day to the slice media. At day 7, BIBF1120 treated cells showed an enhanced migration horizontally over the slice compared to the control population (FIG. 8 a-d). Quantification of GFP-neurons which had migrated beyond a 250 μm perimeter around the deposition site showed a two-fold increase in the BIBF1120-treated population (FIG. 8 g-h). This enhancement of migration was also present along the z-axis as the BIBF1120 treated cells easily migrated throughout the entire slice tissue (FIG. 8 e), whereas the non-treated cells hardly reached the bottom site of the slice (FIG. 80. The total number of human neurons found within 10 μm thick optical planes placed through the middle and the bottom of the slice were quantified to assess the migration rate of BIBF1120 treated versus untreated control and a pure neuronal reference population. Whereas an average of 6.0±3.0, 14.6±6.1 and 31.6±11.0 of control, BIBF1120 treated and pure neurons where found in the middle of the slice, respectively (FIG. 8 *i*) only 2.08±2.0 neurons of the control population but 14±7.8 of the BIBF1120 treated and 20.4±9.0 of the pure neuronal population reached the bottom site of the slice. (FIG. 8 *i*). These data show that interference with the chemoattraction between neural stem/progenitor cells and immature neurons via applying BIBF1120 strongly enhances the migration and integration capacity of neural grafts.

Figure 9:
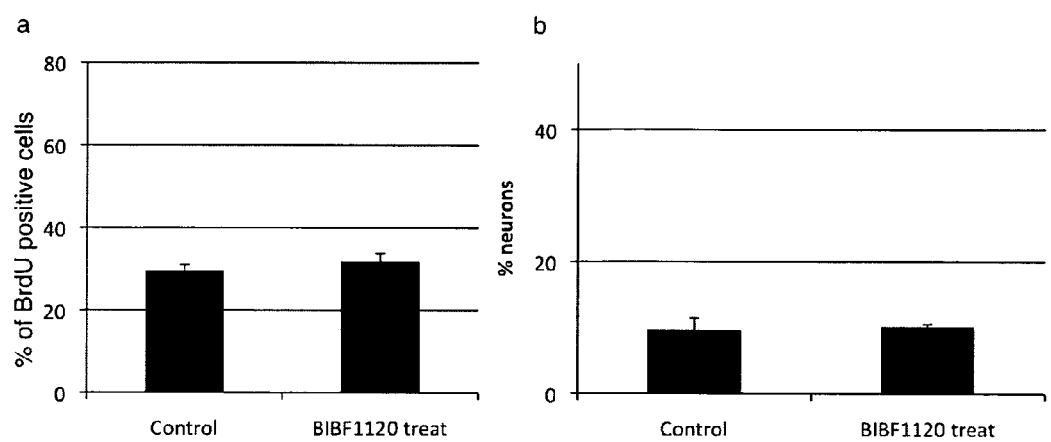
FIG. 9 The effect of BIBF1120 on lt-hESNSC proliferation and differentiation. The proliferative effect was measured in a BrdU proliferation assay of lt-hESNSC, either with or without BIBF1120 (a). Bars represent the percentage of BrdU positive cells, cultured for 20 hours in NSC-medium or in NSC-medium with BIBF1120 (2 µg/ml) and treated for 2.5 h with BrdU. The neurogenic effect of BIBF1120 on lt-hESNSC was studied (b). Bars represent the percentage of βIII tubulin-positive neurons in lt-hESNSC cultured for 10 days in neuronal generation medium or in neuronal generation medium with BIBF1120 (2 µg/ml).

Since differences in cell migration could, in principle, also result from changes in cell proliferation and differentiation, a BrdU proliferation assay was performed as described. This assay revealed no significant difference in the proliferation rate of BIBF1120-treated and untreated control lt-hESNSC (FIG. 9 *a*).

Differentiation was studied by a neurogenesis assay. In this assay lt-hESNSC were cultured for 10 days in neuronal generation medium or in neuronal generation medium with BIBF1120 (2 μg/ml), fixed and stained for μIII tubulin. Quantification of the Bill tubulin-positive neurons revealed that the differentiation of lt-hESNSC is not significantly influenced by BIBF1120 treatment (FIG. 9 *b*).

3. Discussion

Experiments performed in the context of this application provided first evidence that one pivotal mechanism underlying cluster formation and restricted emigration of donor neurons from neural stem/progenitor-containing grafts is chemoattractive interactions between the transplanted neural stem/progenitor cells and immature neurons. In vitro, human neurons showed a pronounced migration towards undifferentiated lt-hESNSC in a transfilter migration assay (see FIG. 1B) indicating that lt-hESNSC express at least one soluble factor having a chemoattractive effect on neurons. In addition, migration assays of cell mixtures composed of neural/neuronal cells in different ratios in rodent CNS tissue revealed that the extent of neuronal migration away from the core is highly dependent on and inversely proportional to the number of neural stem/progenitor cells present in the transplanted population, with a proportion of about 30% neural stem/progenitors being sufficient to almost completely inhibit migration away from the transplantation site. These data demonstrate that interaction between neural stem/progenitors and neurons is one major reason for the observed core formation in neural transplants. One possibility to avoid core formation would thus be to transplant purified immature neurons (hES-N). However, considering that most neural transplants from either ES cells or from fetal tissue contain a considerable amount of neural stem/progenitor cells, and taking into account that establishing a lineage selection system to purify immature neurons might not be feasible for primary cultures, the insight into the mechanisms responsible for this "auto-attraction" phenomenon presented in the present application is of greatest importance for enhancing neuronal migration and integration of transplanted neural populations without the need of lineage selection.

REFERENCES

Aleksandrova M A, Saburina I N, Poltavtseva R A, Revishchin A V, Korochkin L I & Sukhikh G T. (2002). Behavior of human neural progenitor cells transplanted to rat brain. *Brain Res Dev Brain Res* 134, 143-148.

Allen W E, Zicha D, Ridley A J & Jones G E. (1998). A role for Cdc42 in macrophage chemotaxis. *J Cell Biol* 141, 1147-1157.

Amit M, Itskovitz-Eldor J., J. Anat. 2002 March; 200 (Pt 3):225-32. Andrews, P. W., Biochim. Biophys. Acta. 1988; 948, 17-36.

Annett L E, Martel F L, Rogers D C, Ridley R M, Baker H F & Dunnett S B. (1994). Behavioral assessment of the effects of embryonic nigral grafts in marmosets with unilateral 6-OHDA lesions of the nigrostriatal pathway. *Exp Neurol* 125, 228-246.

Aoki H, Onodera H, Yae T, Jian Z & Kogure K. (1993). Neural grafting to ischemic CA1 lesions in the rat hippocampus: an autoradiographic study. Neuroscience 56, 345-354.

Assady et al., Diabetes. 2001 August; 50(8):1691-7.

Ben-Hur T, Einstein O, Mizrachi-Kol R, Ben-Menachem O, Reinhartz E, Karussis D & Abramsky O. (2003). Transplanted multipotential neural precursor cells migrate into the inflamed white matter in response to experimental autoimmune encephalomyelitis. *Glia* 41, 73-80.

Bjorklund A & Lindvall O. (2000). Cell replacement therapies for central nervous system disorders. *Nat Neurosci* 3, 537-544.

Bosnali M E, F. (2008). Generation of transducible versions of transcription factors Oct4 and Sox2. Biol Chem 389, 851-861.

Brittan M., J. Pathol. 2002 July; 197(4):492-509.

Brudno M., Bioinformatics 2003b, 19 Suppl 1:154-162

Brustle O, Choudhary K, Karram K, Huttner A, Murray K, Dubois-Dalcq M & McKay R D. (1998). Chimeric brains generated by intraventricular transplantation of fetal human brain cells into embryonic rats. *Nat Biotechnol* 16, 1040-1044.

Brüstle, O. et al, Science. 1999 Jul. 30; 285(5428):754-6.

Cannon B. et al., Methods Mol. Biol. 2001; 155:213-24

Chaudhary N I, Roth G J, Hilberg F, Muller-Quernheim J, Prasse A, Zissel G, Schnapp A & Park J E. (2007). Inhibition of PDGF, VEGF and FGF signalling attenuates fibrosis. *Eur Respir J* 29, 976-985.

Davies S J, Fitch M T, Memberg S P, Hall A K, Raisman G & Silver J. (1997). Regeneration of adult axons in white matter tracts of the central nervous system. *Nature* 390, 680-683.

du Bois A, Huober J, Stopfer P, Pfisterer J, Wimberger P, Loibl S, Reichardt V L & Harter P. A phase I open-label dose-escalation study of oral BIBF1120 combined with standard paclitaxel and carboplatin in patients with advanced gynecological malignancies. *Ann Oncol* 21, 370-375.

Englund U, Bjorklund A & Wictorin K. (2002a). Migration patterns and phenotypic differentiation of long-term expanded human neural progenitor cells after transplantation into the adult rat brain. *Brain Res Dev Brain Res* 134, 123-141.

Englund U, Fricker-Gates R A, Lundberg C, Bjorklund A & Wictorin K. (2002b). Transplantation of human neural progenitor cells into the neonatal rat brain: extensive migration and differentiation with long-distance axonal projections. Exp Neurol 173, 1-21.

Eriksson K, Magnusson P, Dixelius J, Claesson-Welsh L & Cross M J. (2003). Angiostatin and endostatin inhibit endothelial cell migration in response to FGF and VEGF without interfering with specific intracellular signal transduction pathways. *FEBS Lett* 536, 19-24.

Erlandsson A. (2003). Neural Stem Cell Differentiation and Migration. urn:nbn:se:demo:diva-3546, Göteborg.

Evans M J, Kaufman M H., Nature. 1981 Jul. 9; 292(5819): 154-6.

Ferrara N & Davis-Smyth T. (1997). The biology of vascular endothelial growth factor. *Endocr Rev* 18, 4-25.

Flax J D, Aurora S, Yang C, Simonin C, Wills A M, Billinghurst L L, Jendoubi M, Sidman R L, Wolfe J H, Kim S U & Snyder E Y. (1998). Engraftable human neural stem cells respond to developmental cues, replace neurons, and express foreign genes. *Nat Biotechnol* 16, 1033-1039.

Foxman E F, Kunkel E J & Butcher E C. (1999). Integrating conflicting chemotactic signals. The role of memory in leukocyte navigation. *J Cell Biol* 147, 577-588.

Freed C R, Greene P E, Breeze R E, Tsai W Y, DuMouchel W, Kao R, Dillon S, Winfield H, Culver S, Trojanowski J Q, Eidelberg D & Fahn S. (2001). Transplantation of embryonic dopamine neurons for severe Parkinson's disease. *N Engl J Med* 344, 710-719.

Fricker R A, Carpenter M K, Winkler C, Greco C, Gates M A & Bjorklund A. (1999). Site-specific migration and neuronal differentiation of human neural progenitor cells after transplantation in the adult rat brain. *J Neurosci* 19, 5990-6005.

Friedrich, T. D. et al., Differentiation. 1983; 24, 60-64.

Gepstein L., Circ. Res. 2002 Nov. 15; 91(10):866-76.

Guzman R, Bliss T, De Los Angeles A, Moseley M, Palmer T & Steinberg G. (2008). Neural progenitor cells transplanted into the uninjured brain undergo targeted migration after stroke onset. *J Neurosci Res* 86, 873-882.

Hanna J, Wernig M, Markoulaki S, Sun C W, Meissner A, Cassady J P, Beard C, Brambrink T, Wu L C, Townes T M & Jaenisch R. (2007). Treatment of sickle cell anemia mouse model with iPS cells generated from autologous skin. *Science* 318, 1920-1923.

Herman J P & Abrous N D. (1994). Dopaminergic neural grafts after fifteen years: results and perspectives. *Prog Neurobiol* 44, 1-35.

Hilberg F, Roth G J, Krssak M, Kautschitsch S, Sommergruber W, Tontsch-Grunt U, Garin-Chesa P, Bader G, Zoephel A, Quant J, Heckel A & Rettig W J. (2008). BIBF1120: triple angiokinase inhibitor with sustained receptor blockade and good antitumor efficacy. *Cancer Res* 68, 4774-4782.

Hitoshi S. et al., Genes Dev. 2002 Apr. 1; 16(7):846-58.

Holliger P., Prospero T., Winter G. "Diabodies": small bivalent and bispecific antibody fragments. Proc. Natl. Acad. Sci. U.S.A. 90(14), 6444-6448 (1993)

Honda S, Toda K, Tozuka Y, Yasuzawa S, Iwabuchi K & Tomooka Y. (2007). Migration and differentiation of neural cell lines transplanted into mouse brains. *Neurosci Res* 59, 124-135.

Huangfu D, Maehr R, Guo W, Eijkelenboom A, Snitow M, Chen A E & Melton D A. (2008). Induction of pluripotent stem cells by defined factors is greatly improved by small-molecule compounds. Nat Biotechnol 26, 795-797.

Imitola J, Raddassi K, Park K I, Mueller F J, Nieto M, Teng Y D, Frenkel D, Li J, Sidman R L, Walsh C A, Snyder E Y & Khoury S J. (2004). Directed migration of neural stem cells to sites of CNS injury by the stromal cell-derived factor 1 alpha/CXC chemokine receptor 4 pathway. *Proc Natl Acad Sci USA* 101, 18117-18122.

Jiang Y. et al., Exp Hematol. 2002 August; 30(8):896-904.

Karlin & Altschul (1993) *Proc. Natl. Acad. Sci. USA* 90: 5873-5877

Kaufmann D S., Proc Natl Acad Sci USA. 2001 Sep. 11; 98(19): 10716-21.

Kelly S, Bliss T M, Shah A K, Sun G H, Ma M, Foo W C, Masel J, Yenari M A, Weissman I L, Uchida N, Palmer T & Steinberg G K. (2004). Transplanted human fetal neural stem cells survive, migrate, and differentiate in ischemic rat cerebral cortex. *Proc Natl Acad Sci USA* 101, 11839-11844.

Klug et al. J. Clin. Invest. 1996 July; 98 (1):216-24.

Koch P, Opitz T, Steinbeck J A, Ladewig J & Brustle O. (2009). A rosette-type, self-renewing human ES cell-derived neural stem cell with potential for in vitro instruction and synaptic integration. *Proc Natl Acad Sci USA* 106, 3225-3230.

Kulimova E, Oelmann E, Bisping G, Kienast J, Mesters R M, Schwable J, Hilberg F, Roth G J, Munzert G, Stefanic M, Steffen B, Brandts C, Muller-Tidow C, Kolkmeyer A, Buchner T, Serve H & Berdel W E. (2006). Growth inhibition and induction of apoptosis in acute myeloid leukemia cells by new indolinone derivatives targeting fibroblast growth factor, platelet-derived growth factor, and vascular endothelial growth factor receptors. *Mol Cancer Ther* 5, 3105-3112.

Lee S H, Lumelsky N, Studer L, Auerbach J M & McKay R D. (2000). Efficient generation of midbrain and hindbrain neurons from mouse embryonic stem cells. *Nat Biotechnol* 18, 675-679.

Levenberg S. Proc Natl Acad Sci USA. 2002 Apr. 2; 99(7):4391-6.

Lindvall O. (1999). Engineering neurons for Parkinson's disease. *Nat Biotechnol* 17, 635-636.

Lindvall O & Hagell P. (2001). Cell therapy and transplantation in Parkinson's disease. *Clin Chem Lab Med* 39, 356-361.

Lindvall O, Sawle G, Widner H, Rothwell J C, Bjorklund A, Brooks D, Brundin P, Frackowiak R, Marsden C D, Odin P & et al. (1994). Evidence for long-term survival and function of dopaminergic grafts in progressive Parkinson's disease. *Ann Neurol* 35, 172-180.

Lumelsky M. et al., Science, 2001 May 18; 292(5520):1389-94.

Maherali N, Sridharan R, Xie W, Utikal J, Eminli S, Arnold K, Stadtfeld M, Yachechko R, Tchieu J, Jaenisch R, Plath K & Hochedlinger K. (2007). Directly reprogrammed fibroblasts show global epigenetic remodeling and widespread tissue contribution. Cell Stem Cell 1, 55-70.

Marneros A G & Olsen B R. (2001). The role of collagen-derived proteolytic fragments in angiogenesis. *Matrix Biol* 20, 337-345.

Marneros A G & Olsen B R. (2005). Physiological role of collagen XVIII and endostatin. *FASEB J* 19, 716-728.

Marson A, Foreman R, Chevalier B, Bilodeau S, Kahn M, Young R A & Jaenisch R. (2008). Wnt signaling promotes reprogramming of somatic cells to pluripotency. Cell Stem Cell 3, 132-135.

Means A L., Pancreatology. 2001; 1(6): 587-96.

Mross K B G D, Frost A et al. (2005). A clinical phase I, pharmacokinetic (PK), and pharmacodynamic study of twice daily BIBF1120 in advanced cancer patients. *J Clin Oncol* 23, 3031.

Mummary C. et al., J. Anat. 2002 March; 200 (Pt 3):233-42.

Nakagawa M, Koyanagi M, Tanabe K, Takahashi K, Ichisaka T, Aoi T, Okita K, Mochiduki Y, Takizawa N & Yamanaka S. (2008). Generation of induced pluripotent stem cells without Myc from mouse and human fibroblasts. Nat Biotechnol 26, 101-106.

Nikkhah G, Cunningham M G, Cenci M A, McKay R D & Bjorklund A. (1995). Dopaminergic microtransplants into the substantia nigra of neonatal rats with bilateral 6-OHDA lesions. I. Evidence for anatomical reconstruction of the nigrostriatal pathway. *J Neurosci* 15, 3548-3561.

O'Reilly M S, Boehm T, Shing Y, Fukai N, Vasios G, Lane W S, Flynn E, Birkhead J R, Olsen B R & Folkman J. (1997). Endostatin: an endogenous inhibitor of angiogenesis and tumor growth. *Cell* 88, 277-285.

Okabe S, et al, Mech Dev. 1996 September; 59(1):89-102.

Okano H. J Neurosci Res. 2002 Sep. 15; 69(6):698-707

Okita K, Ichisaka T & Yamanaka S. (2007). Generation of germline-competent induced pluripotent stem cells. *Nature* 448, 313-317.

Okita K, Nakagawa M, Hyenjong H, Ichisaka T & Yamanaka S. (2008). Generation of Mouse Induced Pluripotent Stem Cells Without Viral Vectors. Science.

Olanow C W, Godbold J H & Koller W. (1996). Effect of adding selegeline to levodopa in early, mild Parkinson's disease. Patients taking selegeline may have received more levodopa than necessary. BMJ312, 702-703; author reply 704-705.

Opitz T, Scheffler B, Steinfarz B, Schmandt T & Brustle O. (2007). Electrophysiological evaluation of engrafted stem cell-derived neurons. *Nat Protoc* 2, 1603-1613.

Ostenfeld T & Svendsen C N. (2003). Recent advances in stem cell neurobiology. *Adv Tech Stand Neurosurg* 28, 3-89.

Peng W M, Yu L L, Bao C Y, Liao F, Li X S & Zuo M X. (2002). Transplanted neuronal precursors migrate and differentiate in the developing mouse brain. *Cell Res* 12, 223-228.

Poulsom R. et al., J. Pathol. 2002 July; 197(4):441-56.

Ransohoff R M. (2002). The chemokine system in neuroinflammation: an update. *J Infect Dis* 186 Suppl 2, S152-156.

Reier P J, Perlow M J & Guth L. (1983). Development of embryonic spinal cord transplants in the rat. *Brain Res* 312, 201-219.

Reubinoff B E, Itsykson P, Turetsky T, Pera M F, Reinhartz E, Itzik A & Ben-Hur T. (2001). Neural progenitors from human embryonic stem cells. *Nat Biotechnol* 19, 1134-1140.

Richards K L & McCullough J. (1984). A modified microchamber method for chemotaxis and chemokinesis. *Immunol Commun* 13, 49-62.

Richardson R M, Fillmore H L, Holloway K L & Broaddus W C. (2004). Progress in cerebral transplantation of expanded neuronal stem cells. *J Neurosurg* 100, 659-671.

Roth G J, Heckel A, Colbatzky F, Handschuh S, Kley J, Lehmann-Lintz T, Lotz R, Tontsch-Grunt U, Walter R & Hilberg F. (2009). Design, synthesis, and evaluation of indolinones as triple angiokinase inhibitors and the discovery of a highly specific 6-methoxycarbonyl-substituted indolinone (BIBF1120). *J Med Chem* 52, 4466-4480.

Roy N S, Cleren C, Singh S K, Yang L, Beal M F & Goldman S A. (2006). Functional engraftment of human ES cell-derived dopaminergic neurons enriched by coculture with telomerase-immortalized midbrain astrocytes. *Nat Med* 12, 1259-1268.

Rudge J S & Silver J. (1990). Inhibition of neurite outgrowth on astroglial scars in vitro. *J Neurosci* 10, 3594-3603.

Sanchez-Pernaute R, Studer L, Ferrari D, Perrier A, Lee H, Vinuela A & Isacson O. (2005). Long-term survival of dopamine neurons derived from parthenogenetic primate embryonic stem cells (cyno-1) after transplantation. *Stem Cells* 23, 914-922.

Sanchez-Ramos J R., J Neurosci Res. 2002 Sep. 15; 69(6): 880-93

Schamblott M I., et al., Proc Natl Acad Sci USA. 2001 Jan. 2; 98(1): 113-8

Scheffler B, Schmandt T, Schroder W, Steinfarz B, Husseini L, Wellmer J, Seifert G, Karram K, Beck H, Blumcke I, Wiestler O D, Steinhauser C & Brustle O. (2003). Functional network integration of embryonic stem cell-derived astrocytes in hippocampal slice cultures. *Development* 130, 5533-5541.

Schuldiner M. et al., Brain Res. 2001 Sep. 21; 913(2):201-5.

Schwartz et al., J Clin Invest. 2002 May; 109(10):1291-302.

Smith A G. (2001). Embryo-derived stem cells: of mice and men. *Annu Rev Cell Dev Biol* 17, 435-462.

Soria B. Differentiation. 2001 October; 68(4-5):205-19.

Suzuki A., et al., Cell Transplant. 2001; 10(4-5):393-6

Svendsen C N & Caldwell M A. (2000). Neural stem cells in the developing central nervous system: implications for cell therapy through transplantation. *Prog Brain Res* 127, 13-34.

Tabar V, Panagiotakos G, Greenberg E D, Chan B K, Sadelain M, Gutin P H & Studer L. (2005). Migration and differentiation of neural precursors derived from human embryonic stem cells in the rat brain. *Nat Biotechnol* 23, 601-606.

Takahashi K & Yamanaka S. (2006). Induction of pluripotent stem cells from mouse embryonic and adult fibroblast cultures by defined factors. Cell 126, 663-676.

Thomson J. A., et al., Science. 1998 Nov. 6; 282(5391): 1145-7.

Thompson, J. D., Higgins, D. G. & Gibson, T. J. (1994) *Nucleic Acids Res.* 22, 4673-80

Toma et al., Nat Cell Biol. 2001 September; 3(9): 778-84.

Uchida N, Buck D W, He D, Reitsma M J, Masek M, Phan T V, Tsukamoto A S, Gage F H & Weissman I L. (2000). Direct isolation of human central nervous system stem cells. *Proc Natl Acad Sci USA* 97, 14720-14725.

Von Pawel J K, R.; Eschbach, C.; Stefanic, M.; Love, J.; & Gatzemeier U R, M. (2007). A double-blind phase II study of BIBF1120 in patients suffering from relapsed advanced non-small cell lung cancer (NSCLC). *J Clin Oncol* 25, 7635.

Webb S E, Pollard J W & Jones G E. (1996). Direct observation and quantification of macrophage chemoattraction to the growth factor CSF-1. *J Cell Sci* 109 (Pt 4), 793-803.

Wernig M, Meissner A, Foreman R, Brambrink T, Ku M, Hochedlinger K, Bernstein B E & Jaenisch R. (2007). In vitro reprogramming of fibroblasts into a pluripotent ES-cell-like state. Nature 448, 318-324.

Wilmut I, Schnieke A E, McWhir J, Kind A J & Campbell K H. (1997). Viable offspring derived from fetal and adult mammalian cells. Nature 385, 810-813.

Wobus A M., Mol Aspects Med. 2001 June; 22(3): 149-64.

Xu C. et al., Circ Res. 2002 Sep. 20; 91(6):501-8.

Yan Y, Yang D, Zarnowska E D, Du Z, Werbel B, Valliere C, Pearce R A, Thomson J A & Zhang S C. (2005). Directed differentiation of dopaminergic neuronal subtypes from human embryonic stem cells. *Stem Cells* 23, 781-790.

Yang and Anderson, 1992, *Theriogenology* 38: 315-335.

Yang D, Zhang Z J, Oldenburg M, Ayala M & Zhang S C. (2008). Human embryonic stem cell-derived dopaminergic neurons reverse functional deficit in parkinsonian rats. *Stem Cells* 26, 55-63.

Zhang H, Vutskits L, Pepper M S & Kiss J Z. (2003). VEGF is a chemoattractant for FGF-2-stimulated neural progenitors. *J Cell Biol* 163, 1375-1384.

Zhang S C et al, Nat. Biotechnol. 2001 December; 19(12): 1129-33.

Zicha D, Dunn G A & Brown A F. (1991). A new direct-viewing chemotaxis chamber. *J Cell Sci* 99 (Pt 4), 769-775.

The invention claimed is:

1. A method of promoting migration of immature neurons from a site of transplantation in a patient suffering from a disease or disorder of the nervous system, said method comprising administering to the patient at a transplantation site a neural precursor cell and an inhibitor of chemoattraction selected from the group consisting of endostatin or a variant thereof having at least 90% amino acid sequence identity to human endostatin and having chemoattractant inhibitory activity, angiostatin or a variant thereof having at least 90% amino acid sequence identity to human angiostatin and having chemoattractant inhibitory activity, a VEGF inhibitor, a VEGFR inhibitor, a FGF2 inhibitor, and a FGF2R inhibitor, thereby promoting migration of the immature neurons from the site of transplantation.

2. The method of claim 1, wherein the inhibitor of chemoattraction is administered to the patient prior to, simultaneously with, or subsequently to the administration of neural precursor cells.

3. The method of claim 1, wherein said VEGF inhibitor is an antibody specifically binding to VEGF, said VEGFR inhibitor is an antibody specifically binding to a VEGF receptor, said FGF2 inhibitor is an antibody specifically binding to FGF2, or said FGF2R inhibitor is an antibody specifically binding to a FGF2 receptor.

4. The method of claim 1, wherein the patient suffers from loss of neuronal or glial cells caused by traumatic, ischemic, degenerative, genetic, hypoxic, metabolic, infectious, neoplastic, or toxic disorders of the nervous system.

5. The method of claim 4, wherein the loss of neuronal or glial cells is the result of traumatic lesions of the brain or spinal cord, ischemic infarctions, hemorrhagic infarctions, Parkinson's disease, Huntington's disease, Alzheimer's disease, hereditary atrophic disorders of the cerebellum or brain stem, motoneuron diseases, spinal muscular atrophies, age-related changes, multiple sclerosis, adrenoleukodystrophy, or Pelizaeus-Merzbacher disease.

6. The method of claim 1, wherein the patient suffers from a hereditary metabolic disorder or neoplastic disorder of the nervous system.

7. A method of enhancing the effectiveness of therapy with transplanted neural precursor cells by promoting migration of immature neurons from the transplantation site, said method comprising administering to a patient undergoing said therapy neural precursor cells and an inhibitor of chemoattraction selected from the group consisting of endostatin or a variant thereof having at least 90% amino acid sequence identity to human endostatin and having chemoattractant inhibitory activity, angiostatin or a variant thereof having at least 90% amino acid sequence identity to human angiostatin and having chemoattractant inhibitory activity, a VEGF inhibitor, a VEGFR inhibitor, a FGF2 inhibitor, and a FGF2R inhibitor, thereby enhancing the effectiveness of the therapy with the transplanted neural precursor cells.

8. The method of claim 7, wherein said VEGF inhibitor is an antibody specifically binding to VEGF, said VEGFR inhibitor is an antibody specifically binding to a VEGF receptor, said FGF2 inhibitor is an antibody specifically binding to FGF2, or said FGF2R inhibitor is an antibody specifically binding to a FGF2 receptor.

9. The method of claim 7, wherein the patient suffers from loss of neuronal or glial cells caused by traumatic, ischemic, degenerative, genetic, hypoxic, metabolic, infectious, neoplastic, or toxic disorders of the nervous system.

10. The method of claim 9, wherein the loss of neuronal or glial cells is the result of traumatic lesions of the brain or spinal cord, ischemic infarctions, hemorrhagic infarctions, Parkinson's disease, Huntington's disease, Alzheimer's disease, hereditary atrophic disorders of the cerebellum or brain stem, motoneuron diseases, spinal muscular atrophies, age-related changes, multiple sclerosis, adrenoleukodystrophy, or Pelizaeus-Merzbacher disease.

11. The method of claim 7, wherein the patient suffers from a hereditary metabolic disorder or neoplastic disorder of the nervous system.

12. A method of promoting migration of immature neurons from a site of transplantation into surrounding tissue, said method comprising administering to a patient a neural precursor cell and an inhibitor of chemoattraction that promotes migration of the immature neurons into the surrounding tissue, said inhibitor selected from the group consisting of endostatin or a variant thereof having at least 90% amino acid sequence identity to human endostatin and having chemoattractant inhibitory activity, angiostatin or a variant thereof having at least 90% amino acid sequence identity to human angiostatin and having chemoattractant inhibitory activity, a VEGF inhibitor, a VEGFR inhibitor, a FGF2 inhibitor, and a FGF2R inhibitor.

13. A method of promoting migration of an immature neuron from a site of transplantation, the method comprising contacting transplanted neural precursor cells with an inhibitor of chemoattraction selected from the group consisting of endostatin or a variant thereof having at least 90% amino acid sequence identity to human endostatin and having chemoattractant inhibitory activity, angiostatin or a variant thereof having at least 90% amino acid sequence identity to human angiostatin and having chemoattractant inhibitory activity, a VEGF inhibitor, a VEGFR inhibitor, a FGF2 inhibitor, and a FGF2R inhibitor, wherein the inhibitor of chemoattraction promotes migration of the immature neuron from the transplantation site.

* * * * *